United States Patent
Lodge et al.

(10) Patent No.: US 8,777,917 B2
(45) Date of Patent: Jul. 15, 2014

(54) ABSORBENT ARTICLE HAVING AN ANCHORED CORE ASSEMBLY

(75) Inventors: Richard Worthington Lodge, Colerain Township, OH (US); Fred Naval Desai, Fairfield, OH (US); Donald Carroll Roe, West Chester, OH (US); Bruno Johannes Ehrnsperger, Bad Soden (DE); Frederick Michael Langdon, Blue Ash, OH (US); Luke Robinson Magee, Cincinnati, OH (US); Gary Dean Lavon, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 705 days.

(21) Appl. No.: 11/810,742

(22) Filed: Jun. 7, 2007

(65) Prior Publication Data

US 2008/0004592 A1    Jan. 3, 2008

Related U.S. Application Data

(62) Division of application No. 11/599,862, filed on Nov. 15, 2006, now abandoned.

(60) Provisional application No. 60/811,580, filed on Jun. 7, 2006.

(51) Int. Cl.
*A61F 13/15*      (2006.01)

(52) U.S. Cl.
USPC ................................ 604/385.22; 604/385.27

(58) Field of Classification Search
USPC ................ 604/385.24, 385.27, 397, 400, 402
See application file for complete search history.

(56) References Cited

U.S. PATENT DOCUMENTS

| | | | |
|---|---|---|---|
| 1,917,979 | A | 7/1933 | Kelly |
| 2,652,058 | A | 9/1953 | Carpenter |
| 2,699,171 | A | 1/1955 | McWilliams |
| 3,441,025 | A | 4/1969 | Ralph |
| 3,635,221 | A | 1/1972 | Champaigne |
| 3,658,064 | A | 4/1972 | Pociluyko |
| 3,825,006 | A | 7/1974 | Ralph |
| 3,848,594 | A | 11/1974 | Buell |
| 3,860,003 | A | 1/1975 | Buell |
| 3,929,135 | A | 12/1975 | Thompson |

(Continued)

FOREIGN PATENT DOCUMENTS

| | | |
|---|---|---|
| EP | 0323634 A2 | 12/1989 |
| EP | 0 858 787 | 8/1998 |

(Continued)

OTHER PUBLICATIONS

PCT Search Report, mailed Jul. 6, 2007, 3 pages.

(Continued)

*Primary Examiner* — Melanie Hand
(74) *Attorney, Agent, or Firm* — Kathleen Y. Carter

(57) ABSTRACT

Embodiments of the present disclosure include disposable wearable absorbent articles with anchoring systems. In an embodiment, a disposable wearable absorbent article includes an absorbent core, an outer cover, and an anchoring system configured to anchor the absorbent core to a wearer, wherein the outer cover includes a first portion, in which substantially all of the anchoring system is integral with the outer cover, and a second portion, outside of the first portion.

16 Claims, 35 Drawing Sheets

(56) References Cited

U.S. PATENT DOCUMENTS

| | | |
|---|---|---|
| 4,315,508 A | 2/1982 | Bolick |
| 4,324,246 A | 4/1982 | Mullane et al. |
| 4,342,314 A | 8/1982 | Radel et al. |
| 4,381,781 A | 5/1983 | Sciaraffa et al. |
| 4,463,045 A | 7/1984 | Ahr et al. |
| 4,515,595 A | 5/1985 | Kievit et al. |
| 4,662,875 A | 5/1987 | Hirotsu et al. |
| 4,695,278 A | 9/1987 | Lawson |
| 4,701,174 A | 10/1987 | Johnson |
| 4,770,656 A | 9/1988 | Proxmire et al. |
| 4,795,454 A | 1/1989 | Dragoo |
| 4,834,735 A | 5/1989 | Alemany et al. |
| 4,846,815 A | 7/1989 | Scripps |
| 4,850,992 A | 7/1989 | Amaral et al. |
| 4,857,067 A | 8/1989 | Wood et al. |
| 4,869,724 A | 9/1989 | Scripps |
| 4,888,231 A | 12/1989 | Angstadt |
| 4,892,536 A | 1/1990 | Desmarais et al. |
| 4,894,060 A | 1/1990 | Nestegard |
| 4,909,803 A | 3/1990 | Aziz et al. |
| 4,938,753 A | 7/1990 | Van Gompel et al. |
| 4,940,464 A | 7/1990 | Van Gompel et al. |
| 4,946,527 A | 8/1990 | Battrell |
| 4,962,571 A | 10/1990 | Visser |
| 4,990,147 A | 2/1991 | Freeland |
| 5,006,394 A | 4/1991 | Baird |
| 5,037,416 A | 8/1991 | Allen et al. |
| 5,069,672 A | 12/1991 | Wippler |
| 5,077,868 A | 1/1992 | Visser |
| 5,092,861 A | 3/1992 | Nomura et al. |
| 5,151,092 A | 9/1992 | Buell et al. |
| 5,156,793 A | 10/1992 | Buell et al. |
| 5,167,897 A | 12/1992 | Weber et al. |
| 5,217,447 A | 6/1993 | Gagnon |
| 5,221,274 A | 6/1993 | Buell et al. |
| 5,246,433 A | 9/1993 | Hasse et al. |
| 5,269,775 A | 12/1993 | Freeland et al. |
| 5,304,162 A | 4/1994 | Kuen |
| 5,342,338 A | 8/1994 | Roe |
| 5,358,500 A | 10/1994 | LaVon et al. |
| 5,366,782 A | 11/1994 | Curro et al. |
| 5,374,262 A | 12/1994 | Keuhn et al. |
| 5,386,595 A | 2/1995 | Kuen et al. |
| 5,399,177 A | 3/1995 | Blaney et al. |
| 5,405,682 A | 4/1995 | Shawver et al. |
| 5,411,498 A | 5/1995 | Fahrenkrug et al. |
| 5,423,789 A | 6/1995 | Kuen |
| 5,433,826 A | 7/1995 | Glomb et al. |
| 5,470,639 A | 11/1995 | Gessner et al. |
| 5,518,801 A | 5/1996 | Chappell et al. |
| 5,540,976 A | 7/1996 | Shawver et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,607,416 A | 3/1997 | Yamamoto et al. |
| 5,607,537 A | 3/1997 | Johnson et al. |
| 5,607,760 A | 3/1997 | Roe |
| 5,609,587 A | 3/1997 | Roe |
| 5,620,431 A | 4/1997 | LeMahieu et al. |
| 5,622,589 A | 4/1997 | Johnson et al. |
| 5,625,222 A | 4/1997 | Yoneda et al. |
| 5,634,917 A | 6/1997 | Fujioka et al. |
| 5,635,191 A | 6/1997 | Roe et al. |
| 5,635,290 A | 6/1997 | Stopper et al. |
| 5,643,242 A | 7/1997 | LaVon et al. |
| 5,643,588 A | 7/1997 | Roe et al. |
| 5,662,638 A | 9/1997 | Johnson et al. |
| 5,669,897 A | 9/1997 | LaVon et al. |
| 5,669,901 A | 9/1997 | LaFortune et al. |
| 5,674,216 A | 10/1997 | Buell et al. |
| 5,695,849 A | 12/1997 | Shawver et al. |
| 5,700,256 A | 12/1997 | Yamamoto et al. |
| 5,749,865 A | 5/1998 | Yamamoto et al. |
| 5,772,825 A | 6/1998 | Schmitz |
| 5,776,123 A | 7/1998 | Goerg et al. |
| 5,779,831 A | 7/1998 | Schmitz |
| 5,797,824 A | 8/1998 | Tracy |
| 5,865,823 A | 2/1999 | Curro |
| 5,873,870 A | 2/1999 | Seitz et al. |
| 5,897,545 A | 4/1999 | Kline et al. |
| 5,899,895 A | 5/1999 | Robles et al. |
| 5,916,206 A | 6/1999 | Otsubo et al. |
| 5,916,661 A | 6/1999 | Benson et al. |
| 5,938,648 A | 8/1999 | Lavon et al. |
| 5,941,865 A | 8/1999 | Otsubo et al. |
| 5,944,707 A | 8/1999 | Ronn |
| 5,947,944 A | 9/1999 | Hetzler et al. |
| 5,952,252 A | 9/1999 | Shawver et al. |
| 5,957,908 A | 9/1999 | Kline et al. |
| 5,997,521 A | 12/1999 | Robles et al. |
| 5,997,989 A | 12/1999 | Gessner et al. |
| 6,001,460 A | 12/1999 | Morman et al. |
| 6,004,306 A | 12/1999 | Robles et al. |
| 6,013,589 A | 1/2000 | DeMarais et al. |
| 6,015,764 A | 1/2000 | McCormack et al. |
| 6,042,673 A | 3/2000 | Johnson et al. |
| 6,096,668 A | 8/2000 | Abuto et al. |
| 6,103,647 A | 8/2000 | Shultz et al. |
| 6,107,537 A | 8/2000 | Elder et al. |
| 6,120,487 A | 9/2000 | Ashton |
| 6,120,489 A | 9/2000 | Johnson et al. |
| 6,168,585 B1 | 1/2001 | Cesco-Cancian |
| 6,179,820 B1 | 1/2001 | Fernfors |
| 6,225,243 B1 | 5/2001 | Austin |
| 6,264,641 B1 | 7/2001 | Van Gompel et al. |
| 6,306,121 B1 | 10/2001 | Damaghi et al. |
| 6,313,372 B1 | 11/2001 | Suzuki |
| 6,364,863 B1 | 4/2002 | Yamamoto et al. |
| 6,383,431 B1 | 5/2002 | Dobrin et al. |
| 6,413,249 B1 | 7/2002 | Turi et al. |
| 6,423,043 B1 | 7/2002 | Gustafsson |
| 6,432,098 B1 | 8/2002 | Kline et al. |
| 6,448,467 B1 | 9/2002 | Herrlein et al. |
| 6,465,073 B1 | 10/2002 | Morman et al. |
| 6,479,154 B1 | 11/2002 | Walton et al. |
| 6,482,191 B1 | 11/2002 | Roe et al. |
| 6,503,236 B1 | 1/2003 | Roessler et al. |
| 6,547,774 B2 | 4/2003 | Ono et al. |
| 6,579,274 B1 | 6/2003 | Morman et al. |
| 6,585,713 B1 | 7/2003 | LeMahieu et al. |
| 6,595,975 B2 | 7/2003 | Vogt et al. |
| 6,616,648 B2 | 9/2003 | Hermansson et al. |
| 6,623,468 B2 | 9/2003 | Shimoe |
| 6,623,837 B2 | 9/2003 | Morman et al. |
| 6,627,564 B1 | 9/2003 | Morman et al. |
| 6,632,211 B2 | 10/2003 | Otsubo |
| 6,641,568 B2 | 11/2003 | Ashton et al. |
| 6,677,258 B2 | 1/2004 | Carroll et al. |
| 6,680,265 B1 | 1/2004 | Smith et al. |
| 6,680,422 B2 | 1/2004 | Roe |
| 6,726,792 B1 | 4/2004 | Johnson et al. |
| 6,811,865 B2 | 11/2004 | Morman et al. |
| 6,811,871 B2 | 11/2004 | Sen et al. |
| 6,849,324 B2 | 2/2005 | Meece et al. |
| 6,875,710 B2 | 4/2005 | Eaton et al. |
| 6,896,843 B2 | 5/2005 | Topolkaraev et al. |
| 6,909,028 B1 | 6/2005 | Shawver et al. |
| 6,942,894 B2 | 9/2005 | Alberg et al. |
| 7,013,941 B2 | 3/2006 | Schneider et al. |
| 7,066,921 B2 | 6/2006 | Schmoker et al. |
| 7,087,287 B2 | 8/2006 | Curro et al. |
| 7,094,227 B2 | 8/2006 | Ishiguro et al. |
| 7,122,022 B2 | 10/2006 | Drevik |
| 2001/0023341 A1 | 9/2001 | Karami |
| 2001/0041879 A1 | 11/2001 | Karami et al. |
| 2001/0042584 A1 | 11/2001 | Karami et al. |
| 2002/0007164 A1 | 1/2002 | Boggs et al. |
| 2002/0010455 A1 | 1/2002 | Hermansson et al. |
| 2002/0045879 A1 | 4/2002 | Karami |
| 2002/0111598 A1 | 8/2002 | Vogt et al. |
| 2002/0138065 A1 | 9/2002 | Yeater |
| 2002/0151858 A1 | 10/2002 | Karami et al. |
| 2003/0021951 A1 | 1/2003 | Desai et al. |

(56) References Cited

U.S. PATENT DOCUMENTS

| | | |
|---|---|---|
| 2003/0078558 A1 | 4/2003 | Karami et al. |
| 2003/0084996 A1 | 5/2003 | Alberg et al. |
| 2003/0087059 A1 | 5/2003 | Jackson et al. |
| 2003/0087098 A1 | 5/2003 | Eaton et al. |
| 2003/0088220 A1* | 5/2003 | Molander et al. ............. 604/370 |
| 2003/0088228 A1* | 5/2003 | Desai et al. ............. 604/385.24 |
| 2003/0091807 A1 | 5/2003 | Desai et al. |
| 2003/0109842 A1 | 6/2003 | Louis et al. |
| 2003/0144645 A1 | 7/2003 | Karami |
| 2003/0162458 A1 | 8/2003 | Tsujiyama et al. |
| 2003/0220626 A1 | 11/2003 | Karami |
| 2003/0225382 A1 | 12/2003 | Tombult Meyer et al. |
| 2003/0233082 A1 | 12/2003 | Kline et al. |
| 2004/0006326 A1 | 1/2004 | Nakajima et al. |
| 2004/0082933 A1 | 4/2004 | Karami |
| 2004/0110442 A1 | 6/2004 | Rhim et al. |
| 2004/0121687 A1 | 6/2004 | Morman et al. |
| 2004/0121690 A1 | 6/2004 | Mleziva |
| 2004/0132374 A1 | 7/2004 | Kobayashi |
| 2004/0153043 A1 | 8/2004 | Sugito et al. |
| 2004/0167486 A1 | 8/2004 | Busam et al. |
| 2004/0193133 A1 | 9/2004 | Desai et al. |
| 2004/0193134 A1 | 9/2004 | Mueller et al. |
| 2004/0222553 A1 | 11/2004 | Desai et al. |
| 2005/0096624 A1 | 5/2005 | Hashino et al. |
| 2005/0106980 A1 | 5/2005 | Abed et al. |
| 2005/0124952 A1 | 6/2005 | Zehner et al. |
| 2005/0130544 A1 | 6/2005 | Cheng et al. |
| 2005/0154366 A1 | 7/2005 | Karami et al. |
| 2005/0164586 A1 | 7/2005 | Autran et al. |
| 2005/0165173 A1 | 7/2005 | Autran et al. |
| 2005/0211368 A1 | 9/2005 | McGuire et al. |
| 2005/0214461 A1 | 9/2005 | Desai et al. |
| 2005/0215964 A1 | 9/2005 | Autran et al. |
| 2006/0047260 A1* | 3/2006 | Ashton et al. ................. 604/396 |
| 2006/0141883 A1 | 6/2006 | Nishiguchi et al. |
| 2006/0155253 A1 | 7/2006 | Dziezok et al. |
| 2006/0155254 A1 | 7/2006 | Dziezok et al. |
| 2007/0093769 A1 | 4/2007 | Kline et al. |
| 2007/0202767 A1 | 8/2007 | Anderson et al. |

FOREIGN PATENT DOCUMENTS

| | | |
|---|---|---|
| EP | 1350493 A1 | 10/2003 |
| EP | 1 787 610 | 5/2007 |
| GB | 243 719 | 2/1926 |
| WO | WO 9516746 A1 | 6/1995 |
| WO | WO 98/48750 | 11/1998 |
| WO | WO 2005065680 A1 | 7/2005 |
| WO | WO 2006017518 A2 | 2/2006 |
| WO | WO 2006017674 A1 | 2/2006 |
| WO | WO 2006017518 A3 | 12/2006 |

OTHER PUBLICATIONS

U.S Appl. No. 11/599,829, filed Jun. 7, 2006, Autran, et al.
U.S. Appl. No. 11/599,851, filed Nov. 15, 2006, Lodge, et al.
U.S. Appl. No. 11/599,852, filed Nov. 15, 2006, Roe, et al.
U.S. Appl. No. 11/900,311, filed Sep. 11, 2007, Roe et al.
U.S. Appl. No. 60/811,700, filed Jun. 7, 2006, Roe, et al.
U.S. Appl. No. 11/810,745, filed Jun. 7, 2007, Lodge, et al.
U.S. Appl. No. 11/810,734, filed Jun. 7, 2007, Lodge, et al.
U.S. Appl. No. 11/810,779, filed Jun. 7, 2007, Lodge, et al.
U.S. Appl. No. 11/810,715, filed Jun. 7, 2007, Lodge, et al.
U.S. Appl. No. 11/810,733, filed Jun. 7, 2007, Lodge, et al.
U.S. Appl. No. 11/810,736, filed Jun. 7, 2007, Desai, et al.
U.S. Appl. No. 11/810,777, filed Jun. 7, 2007, Langdon, et al.
U.S. Appl. No. 11/810,741, filed Jun. 7, 2007, Desai, et al.
U.S. Appl. No. 11/810,708, filed Jun. 7, 2007, Roe, et al.
U.S. Appl. No. 11/810,901, filed Jun. 7, 2007, Lodge, et al.
U.S. Appl. No. 11/810,801, Jun. 7, 2007, Autran.
U.S. Appl. No. 11/077,779, filed Mar. 11, 2005, Donald Carroll Roe, et al.

* cited by examiner

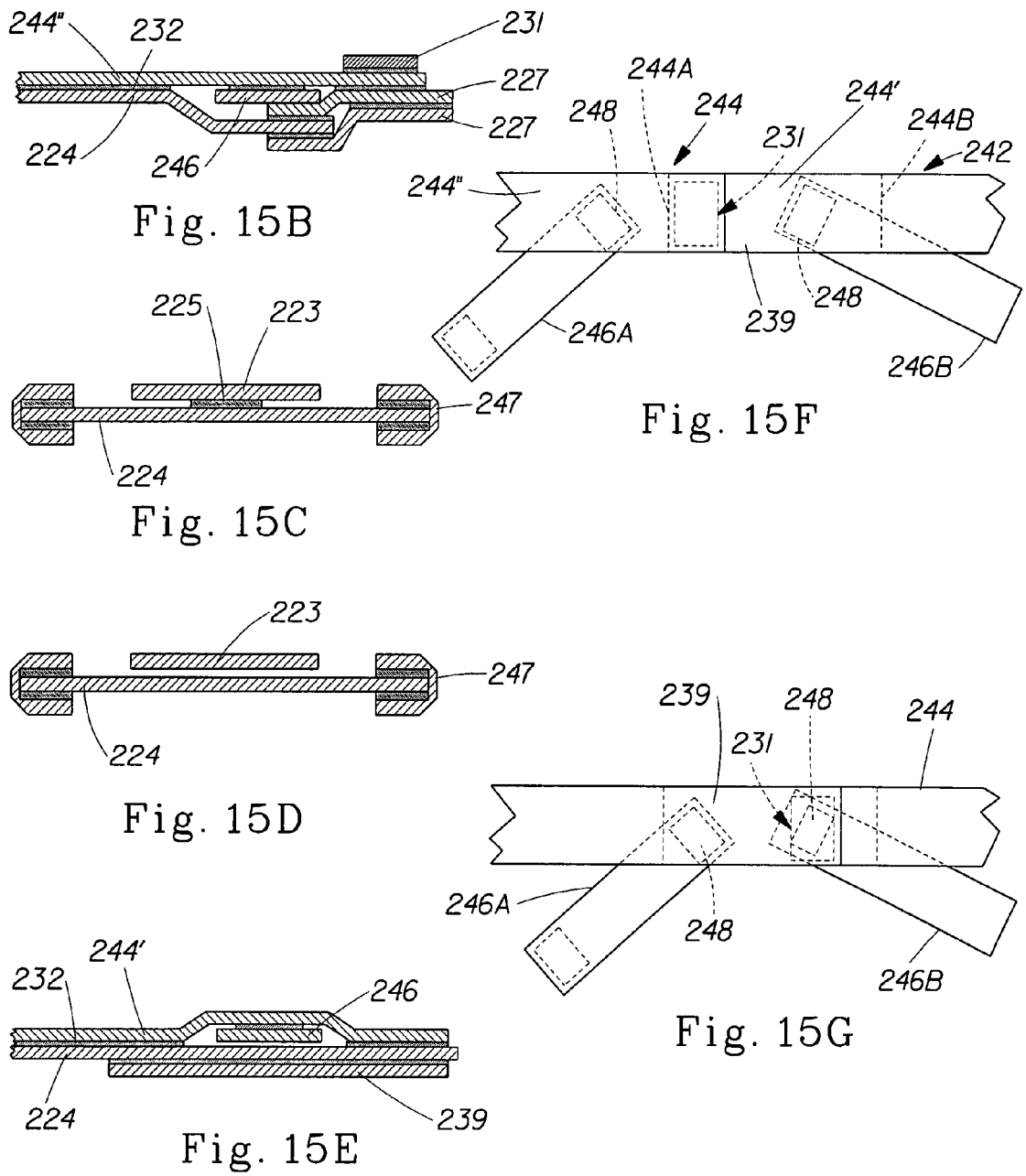

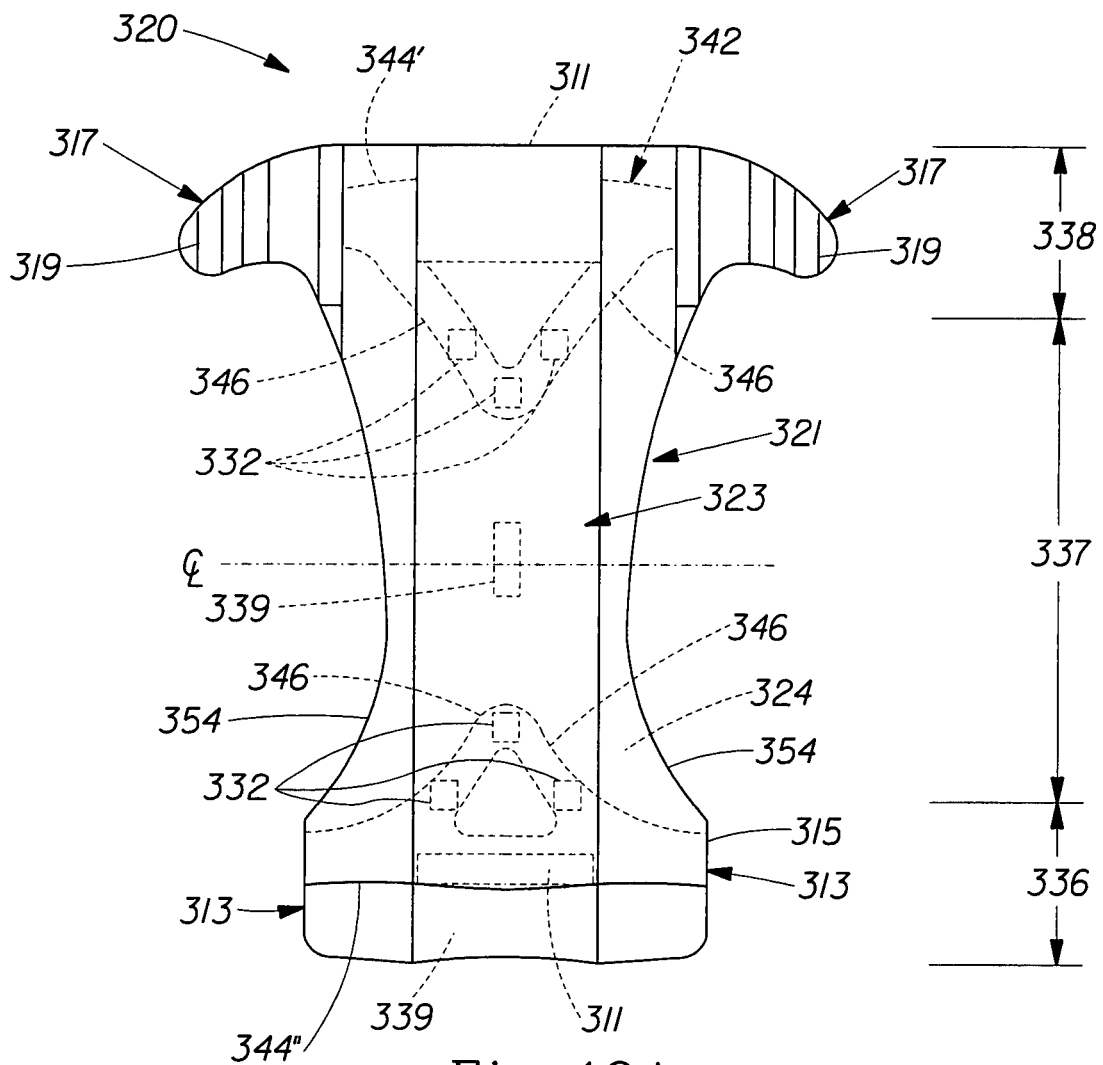
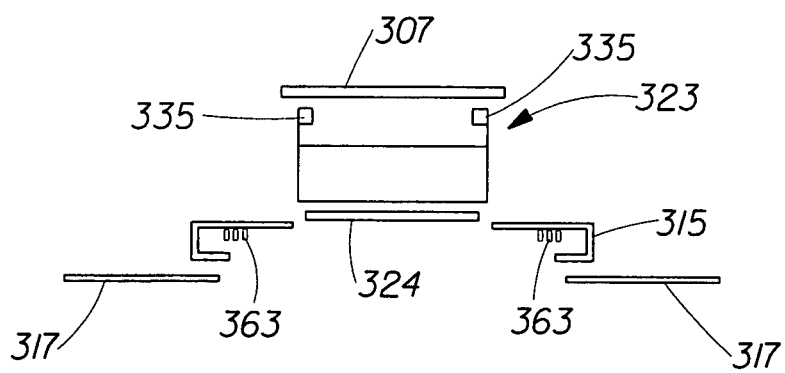
Fig. 19A
Fig. 19B

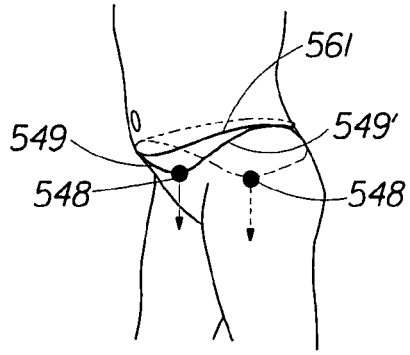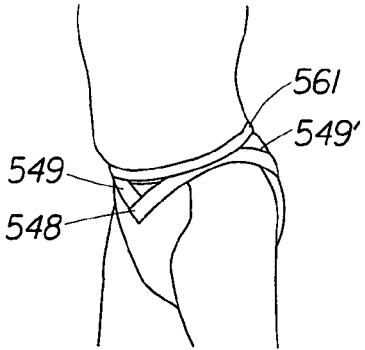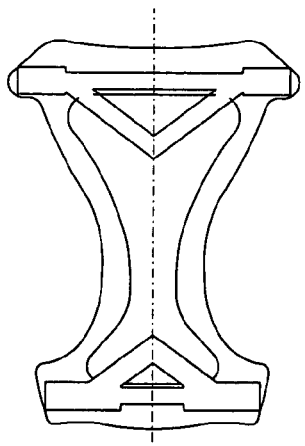
Fig. 29A   Fig. 29B   Fig. 29C
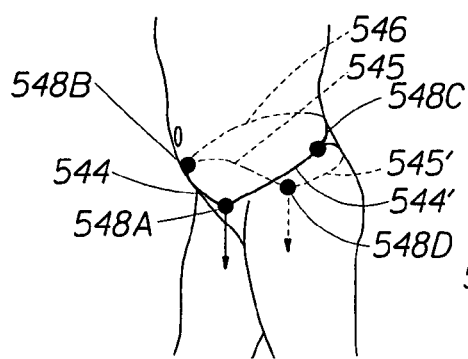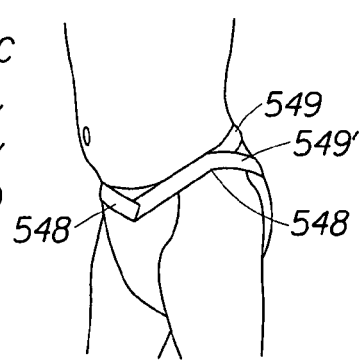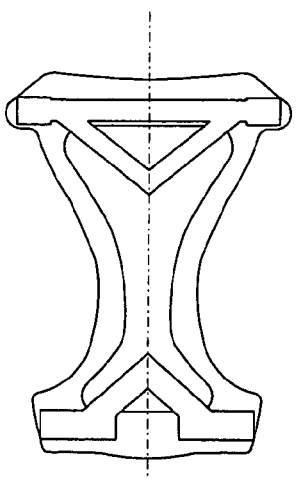
Fig. 30A   Fig. 30B   Fig. 30C

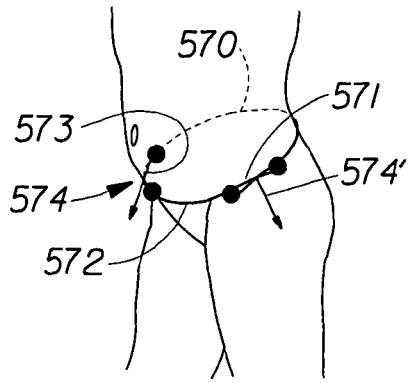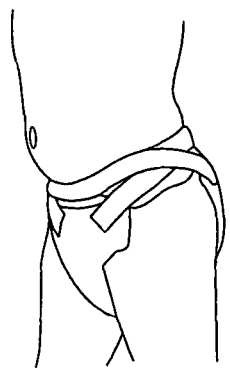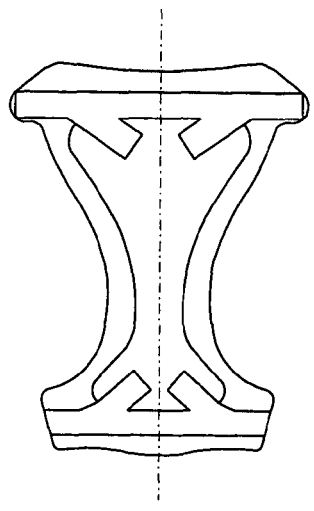
Fig. 33A    Fig. 33B    Fig. 33C
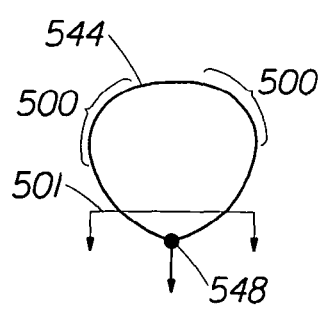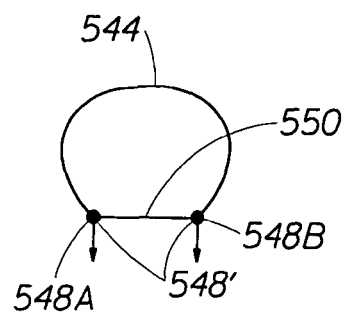
Fig. 34    Fig. 35

US 8,777,917 B2

ABSORBENT ARTICLE HAVING AN ANCHORED CORE ASSEMBLY

CROSS REFERENCE TO RELATED APPLICATIONS

This application is a divisional of U.S. application Ser. No. 11/599,862, filed on Nov. 15, 2006 now abandoned, which claims the benefit of U.S. Provisional Application No. 60/811,580, filed Jun. 7, 2006, both of which are hereby incorporated by reference. This application also claims the benefit of U.S. Provisional Application No. 60/811,580, filed Jun. 7, 2006.

FIELD OF INVENTION

This invention relates to absorbent articles generally, and in particular relates to an absorbent article having an absorbent core and an anchoring system that supports the core assembly of the absorbent article.

BACKGROUND OF THE INVENTION

It has long been known that absorbent articles such as conventional taped diapers, pull-on diapers, training pants, incontinence briefs, and the like, offer the benefit of receiving and containing urine and/or other bodily exudates. Such absorbent articles can include a chassis that defines a waist opening and a pair of leg openings. A pair of barrier leg cuffs can extend from the chassis toward the wearer adjacent the leg openings, thereby forming a seal with the wearer's body to improve containment of liquids and other body exudates. Conventional chassis include a core that is disposed between a topsheet and a garment-facing outer cover (also known as a backsheet).

The outer cover can include a stretchable waistband at one or both of its ends (e.g., proximal opposing laterally extending edges), stretchable leg bands surrounding the leg openings, and stretchable side panels, which can be integral or separate discrete elements attached directly or indirectly to the outer cover. The remainder of the outer cover typically comprises a non-stretchable nonwoven-breathable film laminate. Unfortunately, such diapers do not conform well to the wearer's body during different body movements, e.g. sitting, standing, and walking due to the relative anatomic dimensional changes (which can, in some instances, be up to 50%) in the buttocks region caused by these movements. This problem is further exacerbated by the fact that one diaper typically has to fit all the wearers in a given size range.

The dimensions of the smallest and biggest wearers within a given size range can be markedly different. For instance the waist circumference at the navel can vary by 80 mm within a given size range. Also, the navel-to-back distance, which is the distance from the navel, through the crotch, and to a point on the back of the wearer that is in the same horizontal plane as the navel, can vary by about 80 mm from the smallest to the largest wearers in this same size.

In addition, it has been determined that caregivers and wearers prefer the look and feel of cotton underwear (not provided by conventional disposable diapers) for several reasons. For instance, cotton underwear include elastic waist and leg bands that encircle the waist and leg regions of the wearer and provide forces that keep the underwear on the wearer's body. Furthermore, the cotton outer cover (except in the waist and leg bands) can be stretched along the width and length directions in response to a relatively low force to accommodate the anatomic dimensional differences related to movement and different wearer positions. The stretched portion returns back to substantially its original dimension once the applied force is removed. In other words, the cotton outer cover of the underwear has low-force, recoverable biaxial stretch that provides a conforming fit to a wider array of wearer sizes than conventional diapers.

An effort has therefore begun to develop diapers that simulate the look and feel of traditional cotton underwear. However, diapers, unlike cotton underwear, are designed to receive and retain loads (i.e., bodily exudates) that are received during use while minimizing or eliminating leakage. It has been found that the downward forces resulting from these loads cause biaxially stretchable outer covers from the prior art to sag, droop, or otherwise distend to the detriment of the fit of the diaper on the wearer. Sagging is generally unsightly, and can cause leakage of the bodily exudates due to, for example, displacement of the barrier leg cuffs away from the wearer's body.

What is therefore needed is an absorbent article including an anchoring system which is capable of supporting the core assembly thereby supporting the (downward) force(s) exerted by the core assembly. Additionally, what is needed is an absorbent article capable of including a bi-axially stretchable outer cover while minimizing occurrences of sagging of the outer cover and leakage during use.

BRIEF DESCRIPTION OF THE DRAWINGS

Reference is hereby made to the following figures in which like reference numerals correspond to like elements throughout, and in which:

FIG. 15B illustrates a cross-sectional view of the disposable absorbent article of FIG. 15A, according to the present disclosure.

FIG. 15C illustrates a cross-sectional view of the disposable absorbent article of FIG. 15A, according to the present disclosure.

FIG. 15D illustrates a cross-sectional view of the disposable absorbent article of FIG. 15A, according to the present disclosure.

FIG. 15E illustrates a cross-sectional view of the disposable absorbent article of FIG. 15A, according to the present disclosure.

FIG. 15F illustrates an embodiment of elements of an anchoring system for use in a disposable absorbent article, according to the present disclosure.

FIG. 15G illustrates an embodiment of elements of an anchoring system for use in a disposable absorbent article, according to the present disclosure.

FIG. 19A illustrates a plan view of an embodiment of a disposable absorbent article with an absorbent core and an anchoring system, according to the present disclosure.

FIG. 19B illustrates a cross-sectional view of the disposable absorbent article of FIG. 19A, according to the present disclosure.

FIG. 29A illustrates a perspective view of a human body with force vectors relating to a further particular embodiment of an anchoring system for a disposable absorbent article, according to the present disclosure.

FIG. 29B illustrates a perspective view of the anchoring system for the force vectors of FIG. 29A, according to the present disclosure.

FIG. 29C illustrates a perspective view of the disposable absorbent article for the anchoring system of FIG. 29B, according to the present disclosure.

FIG. 30A illustrates a perspective view of a human body with force vectors relating to a still further particular embodiment of an anchoring system for a disposable absorbent article, according to the present disclosure.

FIG. 30B illustrates a perspective view of the anchoring system for the force vectors of FIG. 30A, according to the present disclosure.

FIG. 30C illustrates a perspective view of the disposable absorbent article for the anchoring system of FIG. 30B, according to the present disclosure.

FIG. 33A illustrates a perspective view of a human body with force vectors relating to another additional particular embodiment of an anchoring system for a disposable absorbent article, according to the present disclosure.

FIG. 33B illustrates a perspective view of the anchoring system for the force vectors of FIG. 33A, according to the present disclosure.

FIG. 33C illustrates a perspective view of the disposable absorbent article for the anchoring system of FIG. 33B, according to the present disclosure.

FIG. 34 illustrates a top view of force vectors relating to an embodiment of an anchoring system for a disposable absorbent article, according to the present disclosure.

FIG. 35 illustrates a top view of force vectors relating to an embodiment of an anchoring system for a disposable absorbent article, according to the present disclosure.

DETAILED DESCRIPTION OF THE INVENTION

Definitions

Figure 1A:
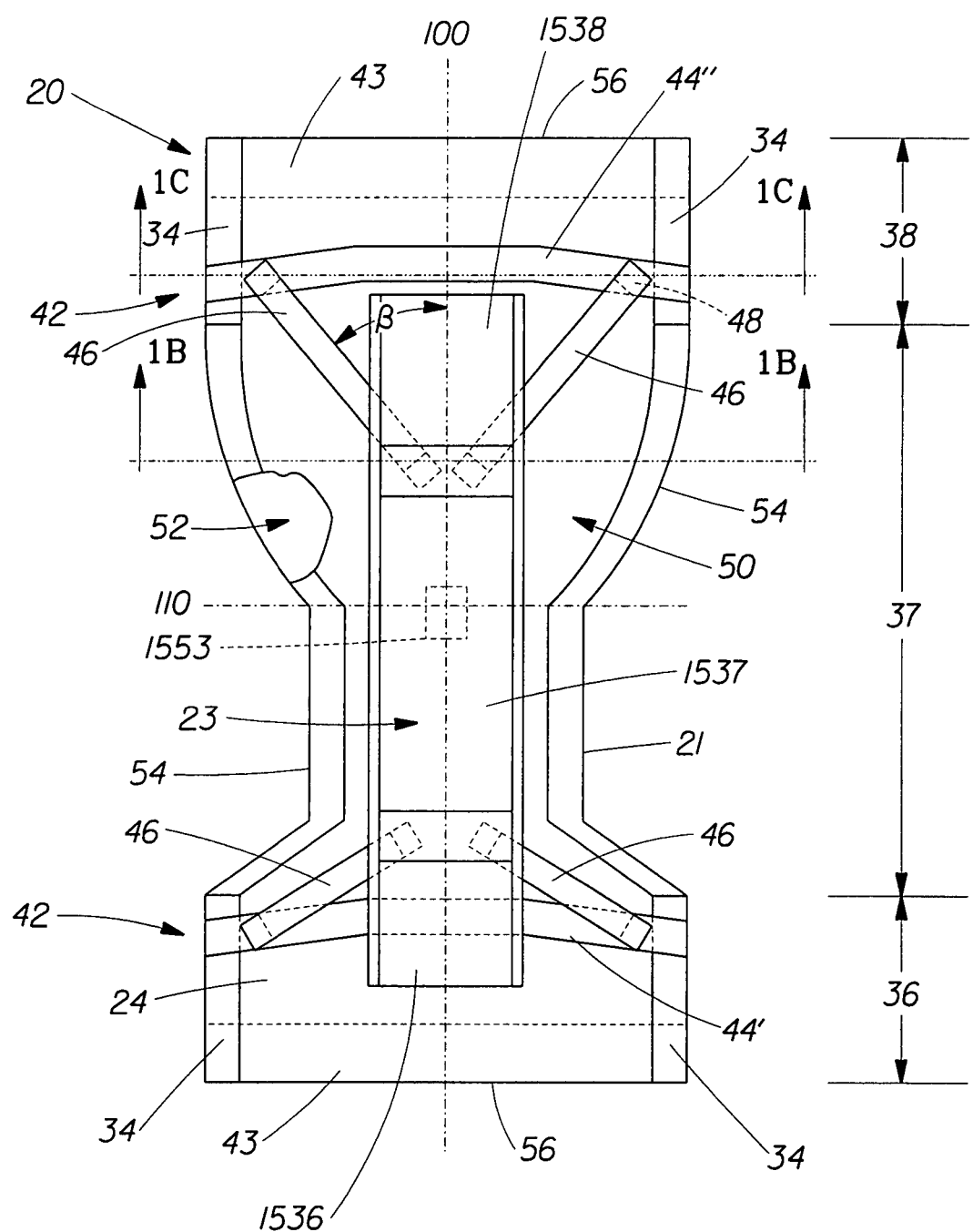
FIG. 1A illustrates a plan view of an embodiment of a disposable absorbent article with an absorbent core and an anchoring system, according to the present disclosure.

As used herein, the following terms shall have the meaning specified thereafter:

The term "disposable," as used herein in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

The term "absorbent article" as used herein refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

The term "diaper" as used herein refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

The terms "proximal" and "distal" as used herein refer respectively to the location of an element relatively near to or far from the center of a structure (e.g., the proximal edge of a longitudinally extending element is located nearer to the longitudinal axis than the distal edge of the same element is located relative to the same longitudinal axis).

The terms "body-facing", "inner-facing", "outer-facing", and "garment-facing" as used herein refer respectively to the relative location of an element or a surface of an element or group of elements. "Body-facing" and "inner-facing" imply the element or surface is nearer to the wearer during wear. "Garment-facing" and "outer-facing" imply the element or surface is more remote from the wearer during wear (i.e., element or surface is nearer to the wearer's garments that can be worn over the disposable absorbent article).

The term "longitudinal" as used herein refers to a direction running substantially perpendicular from a waist edge to an opposing waist edge of the article and generally parallel to the maximum linear dimension of the article. Directions within 45 degrees of the longitudinal direction are considered to be "longitudinal."

The term "lateral" as used herein refers to a direction running from a longitudinal edge to an opposing longitudinal edge of the article and generally at a right angle to the longitudinal direction. Directions within 45 degrees of the lateral direction are considered to be "lateral."

"Longitudinal Centerline" refers to a longitudinal line that can be drawn through the middle of an absorbent article. For most absorbent articles, the longitudinal centerline separates the article into two substantially symmetrical halves that will fall on the left and right halves of a wearer during wear.

"Lateral Centerline" refers to a lateral line drawn through the midpoint of the longitudinal centerline and perpendicular to the longitudinal centerline.

The term "disposed" as used herein refers to an element being attached and positioned in a particular place or position with regard to another element.

"Liquid permeable" and "liquid impermeable" refer to the penetrability of materials in the context of the intended usage of disposable absorbent articles. Specifically, the term "liquid permeable" refers to a layer or a layered structure having pores, openings, and/or interconnected void spaces that permit liquid water to pass through its thickness in the absence of a forcing pressure. Conversely, the term "liquid impermeable" refers to a layer or a layered structure through the thickness of which liquid water cannot pass in the absence of a forcing pressure. Liquid impermeable materials exhibit a hydrohead of at least about 5 mbar as measured according to the Hydrostatic Head (Hydrohead) Pressure Test provided below in the Test Methods. However, it may be desirable that a liquid impermeable material exhibit a hydrohead of at least about 10 mbar or about 15 mbar. A layer or a layered structure that is water-impermeable according to this definition may be permeable to vapor (i.e., may be "vapor permeable"). Such a vapor permeable layer or layered structure is commonly known in the art as "breathable."

As used herein the term "stretchable" refers to materials which can stretch to at least an elongated length of 105% on the upcurve of the hysteresis test at a load of about 400 gm/cm. The term "non-stretchable" refers to materials which cannot stretch to at least 5% on the upcurve of the hysteresis test at a load of about 400 gm/cm.

The terms "elastic" and "elastomeric" as used herein refer to any material that upon application of a biasing force, can stretch to an elongated length of at least about 110%, preferably to 125% of its relaxed, original length (i.e. can stretch to 10 percent, preferably 25% more than its original length), without rupture or breakage, and upon release of the applied force, recovers at least about 40% of its elongation, preferably recovers at least 60% of its elongation, most preferably recovers at least about 80% of its elongation. For example, a material that has an initial length of 100 mm can extend at least to 110 mm, and upon removal of the force would retract to a length of 106 mm (40% recovery). The term "inelastic" refers herein to any material that does not fall within the definition of "elastic" above.

The term "extensible" as used herein refers to any material that upon application of a biasing force, can stretch to an elongated length of at least about 110%, preferably 125% of its relaxed, original length (i.e. can stretch to 10 percent, preferably 25% more than its original length), without rupture or breakage, and upon release of the applied force, shows little recovery, less than about 40%, preferably less than about 20% and more preferably less than about 10% of its elongation.

The terms "outboard" and "inboard" as used herein refer respectively to the location of an element disposed relatively far from or near to the longitudinal centerline of the diaper with respect to a second element. For example, if element A is outboard of element B, then element A is farther from the longitudinal centerline than is element B.

The term "anchoring zone" as used herein refers to an area of contact between the diaper and wearer where at least a portion of the load force is supported by the wearer's body. Multiple anchoring zones can be desirable to increase diaper support. Once their locations are identified, they map to corresponding zones in the diaper.

The term "core assembly" as used herein refers to at least an absorbent core and other optional structures (e.g., barrier cuffs, liquid barrier layer, storage layer, acquisition layer, distribution layer, etc.) to enhance containment of waste and/or structures to enhance structural integrity.

The term "circumference" or "circumferential" as used herein, refers to a closed path on the surface around the torso of the body or around a leg. That path can have a smooth, continuous curvature, or it can have "corners" where the curvature makes an abrupt change, e.g. when the path passes through a connection zone with three or more connecting tension-carrying bands.

The term "circumferential anchoring member", or "CAM", as used herein, refers to one or more anchoring bands, that form a substantially circumferential path (or partial circumferential path) around at least a portion of a wearer that is joined to a core assembly at both ends, for carrying tension that is substantially in a defined path when the diaper is worn.

The term "force-decoupled" as used herein, refers to a configuration of an absorbent article where movement of one element or location in an article will not create a substantial force on a second given element or location. In practice this typically means that any material pathway that connects the two elements or locations has enough slack or force attenuation such that the movement of the first element does not induce substantial movement in the second element. In some cases where more than one pathway exists between the two elements or locations, it may be appropriate to state that all or just particular pathways are force-decoupled.

The terms "pant", "training pant", "pre-closed diaper", "pre-fastened diaper", "pull-on diaper", and "pant-like garment" as used herein, refer to disposable garments having a waist opening and leg openings designed for infant or adult wearers. A pant can be configured such that the pant has closed waist and leg openings prior to being donned on the wearer, or the pant can be configured such that the waist is closed and the leg openings formed while on the wearer. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened, rear waist fastened), or at the crotch. Examples of suitable pants are disclosed in U.S. Pat. No. 5,246,433; U.S. Pat. No. 5,569,234; U.S. Pat. No. 6,120,487; U.S. Pat. No. 6,120,489; U.S. Pat. No. 4,940, 464; U.S. Pat. No. 5,092,861; U.S. Pat. No. 5,897,545; U.S. Pat. No. 5,957,908; and U.S. Patent Publication No. 2003/ 0233082 A1.

The term "pre-closed" refers to an absorbent article that has been formed into a pant-like garment prior to packaging such that the end user receives the article as a pant-like garment that can be directly applied to the wearer. The term "pre-closed" also encompasses an absorbent article that can be closed by the end user and formed into a pant-like garment prior to applying the garment to the wearer.

As used herein, the terms "substantially" when referring to a quantitative value are intended to include +/−20% of the stated quantitative value.

"Joined" refers to configurations whereby an element is directly secured to another element by affixing the element directly to the other element and to configurations whereby an element is indirectly secured to another element by affixing the element to intermediate member(s) which in turn are affixed to the other element.

Description

Absorbent articles of the present invention provide an anchoring system which can support the (downward) forces exerted by a core assembly. Additionally, some embodiments of the present invention provide an absorbent article which includes a stretchable outer cover while reducing the occurrences of sagging of the outer cover and leakage during use.

In embodiments of the present disclosure, an absorbent article having an anchoring system, as described herein, can include a stretchable outer cover. For example, the outer cover can be a uniaxially stretchable outer cover, configured to stretch in one direction. Also as an example, the outer cover can be a biaxially stretchable outer cover, configured to stretch in two directions. In various embodiments, the outer cover can be configured as described in US non-provisional patent application Ser. No. 11/599,829 entitled "Biaxially Stretchable Outer Cover for an Absorbent Article," filed on Nov. 15, 2006 with Express Mail No. EV916939625 and which is hereby incorporated by reference.

In embodiments of the present disclosure, an absorbent article having an anchoring system, as described herein, can be configured with various structures and/or functions as described in US non-provisional patent application Ser. No. 11/599,851 entitled "Disposable Wearable Absorbent Articles With Anchoring Systems," filed on Nov. 15, 2006 with Express Mail No. EV916939648 and which is hereby incorporated by reference. Also, in embodiments of the present disclosure, an absorbent article having an anchoring system, as described herein, can have a wrap and tuck configuration as described in US non-provisional patent application Ser. No. 11/599,852 entitled "Disposable Absorbent Article Having a Wrap and Tuck Configuration," filed on Nov. 15, 2006 with Express Mail No. EV916939617 and which is hereby incorporated by reference.

Referring to FIG. 1A, an absorbent article constructed in accordance with the present invention may comprise, in some embodiments, a diaper 20. The diaper 20 may have a longitudinal centerline 100 and a lateral centerline 110. The diaper 20, which is illustrated in FIG. 1A as a pant-like garment, defines an inner surface 50 and an opposing outer surface 52. The inner surface 50 generally includes that portion of the diaper 20 which is positioned adjacent the wearer's body during use (i.e., wearer-facing), while the outer surface 52 generally comprises that portion of the diaper 20 which is positioned away from the wearer's body (i.e., garment-facing).

The diaper 20, in some embodiments, includes a chassis 21, a core assembly 23, and an anchoring system 42. The chassis 21 includes a first, or front, waist region 36, a second, or back, waist region 38 opposed to the front waist region 36, and a crotch region 37 located between the front waist region 36 and the back waist region 38. The waist regions 36 and 38 generally comprise those portions of the diaper 20 which, when the diaper 20 worn, encircle the waist of the wearer. The waist regions 36 and 38 can include elastic elements such that they gather about the waist of the wearer to provide improved fit and containment. The crotch region 37 is that portion of the diaper 20 which, when the diaper 20 is worn, is generally positioned between the legs of the wearer.

The outer periphery of the chassis 21 is defined by lateral end edges 56 that can be oriented generally parallel to the lateral centerline 110, and by longitudinal side edges 54 that can be oriented generally parallel to the longitudinal centerline 100 or, for better fit, can be curved or angled, as illustrated, to produce an "hourglass" shaped garment when viewed in a plan view. In some embodiments, the longitudinal centerline 100 can bisect the end edges 56 while the lateral centerline 110 can bisect the side edges 54.

In some embodiments, the chassis 21 can comprise an outer cover 24 extending between, and defining, the lateral end edges 56 and the longitudinal end edges 54. The outer cover 24 can advantageously be stretchable in one or more directions, elastic in one or more directions, preferably biaxially stretchable, and preferably still biaxially elastic, thereby enhancing both the comfort of the diaper 20 on the wearer and the conformability to the wearer's anatomy during movement. In some embodiments, the outer cover 24 may be non-stretchable. The outer cover 24 is discussed further hereafter.

The diaper 20 may further comprise the core assembly 23 which can be positioned on a wearer-facing surface of the outer cover 24. The core assembly 23 is the portion of the diaper 20 providing much of the absorptive and containment function. In some embodiments, it may be desirable to attach the core assembly 23 to the outer cover 24 in as few locations as possible; this can make the outer cover 24 look and feel softer. However, in order to make the design more tamper-resistant, it may be useful to attach the core assembly 23 to the outer cover 24 along at least part, if not all, of the core assembly's periphery; or a small distance (about 5-20 mm) inboard of the periphery. For example, the bond area between the core assembly 23 and the outer cover 24 can be less than about 70%, or, as another example, less than about 50%, or, as yet another example, less than about 20% of the area of the core assembly 23.

The core assembly 23 comprises a first portion 1536, a second portion 1538, and a third portion 1537. As shown, the first portion 1536 can be disposed, in part, in the first waist region 36. Similarly, the second portion 1538 and the third portion 1537 can be disposed, in part, in the second waist region 38 and the crotch region 37, respectively.

Embodiments are contemplated where the core assembly 23 is joined to the outer cover in a central region 1553 of the core assembly 23. In some embodiments, the bond area can be between about 1 cm$^2$ and about 20 cm$^2$ or any individual number within the range. In some embodiments, the core assembly 23 may be bonded to the outer cover 24 wherein the bond area resembles a strip extending the substantial length of the core assembly, e.g. being long and narrow.

Figure 1B:
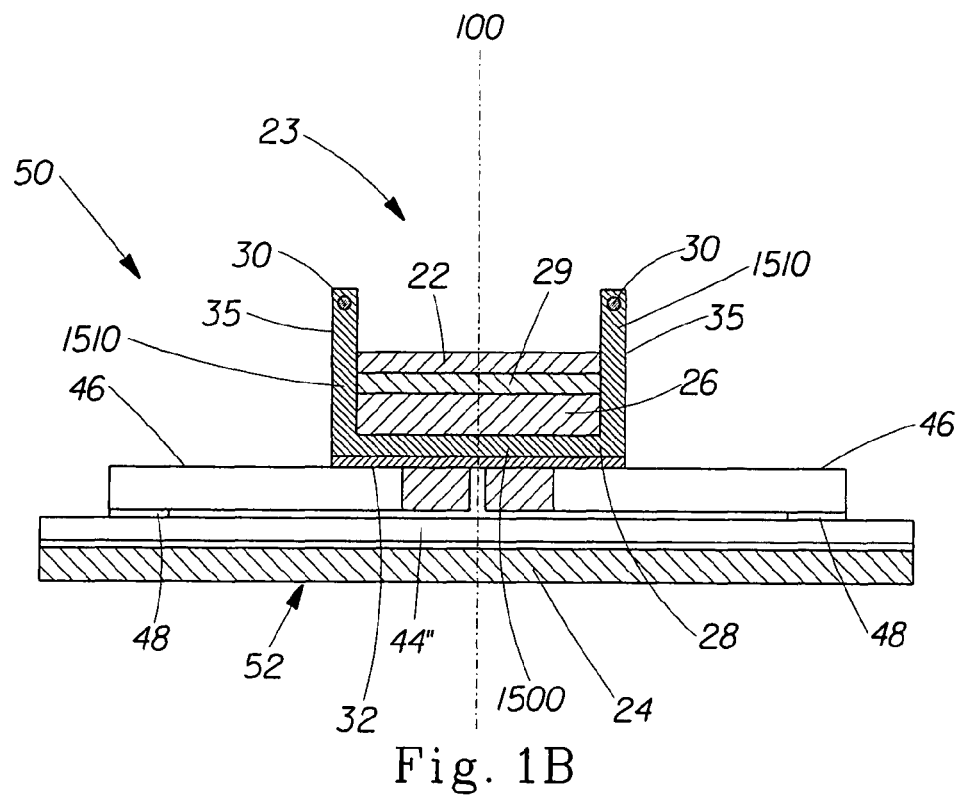
FIG. 1B illustrates a cross-sectional view of the disposable absorbent article of FIG. 1A, according to the present disclosure.

As shown in FIG. 1B, the absorbent core assembly 23 may include an absorbent core 26 that can be disposed symmetrically or asymmetrically with respect to either or both of the longitudinal centerline 100 and/or the lateral centerline 110. Similarly, the core assembly 23 may be disposed symmetrically or asymmetrically with respect to either or both the longitudinal centerline 100 and/or the lateral centerline 110. Referring back to FIG. 1A, the absorbent core 26 and core assembly 23 are shown symmetrical with respect to both the longitudinal centerline 100 and the lateral centerline 110. The core assembly 23 is discussed further hereafter.

As shown in FIG. 1B, in some embodiments, the core assembly 23 may comprise a topsheet 22 which can have a length and a width dimensions that are substantially similar to those of the absorbent core 26, while the outer cover 24 has length and width dimensions generally larger than those of the absorbent core 26. The outer cover 24 thus forms the periphery of the diaper 20.

Referring to FIG. 1A, the present invention recognizes that the core 26 is capable of absorbing substantial loads during use, and that the fit of conventional diapers can be worsened when the increased weight and resultant (downward) forces exerted on the core (and from the core to other diaper components) can cause the diaper 20 to sag or otherwise be distended. Accordingly, the diaper 20 constructed in accordance with the principles of the present invention includes the anchoring system 42 intended to fit to the pelvic region of the wearer's torso region while directly supporting the core assembly 23. As shown, in some embodiments, the anchoring system 42 of the present invention may comprise a plurality of load distribution elements (LDEs) 46 capable of directing the load forces to at least a portion of the wearer's waist region where the forces can be coupled into the wearer's body. As a result, the anchoring system 42 can prevent, or minimize, sagging during wear while the side edges and end edges, 54 and 56, respectively, move with the parts of the body (spine/abdomen and legs, respectively) that can move relative to the pelvis without being too uncomfortable/creating too much pressure for the wearer.

Figure 2A:
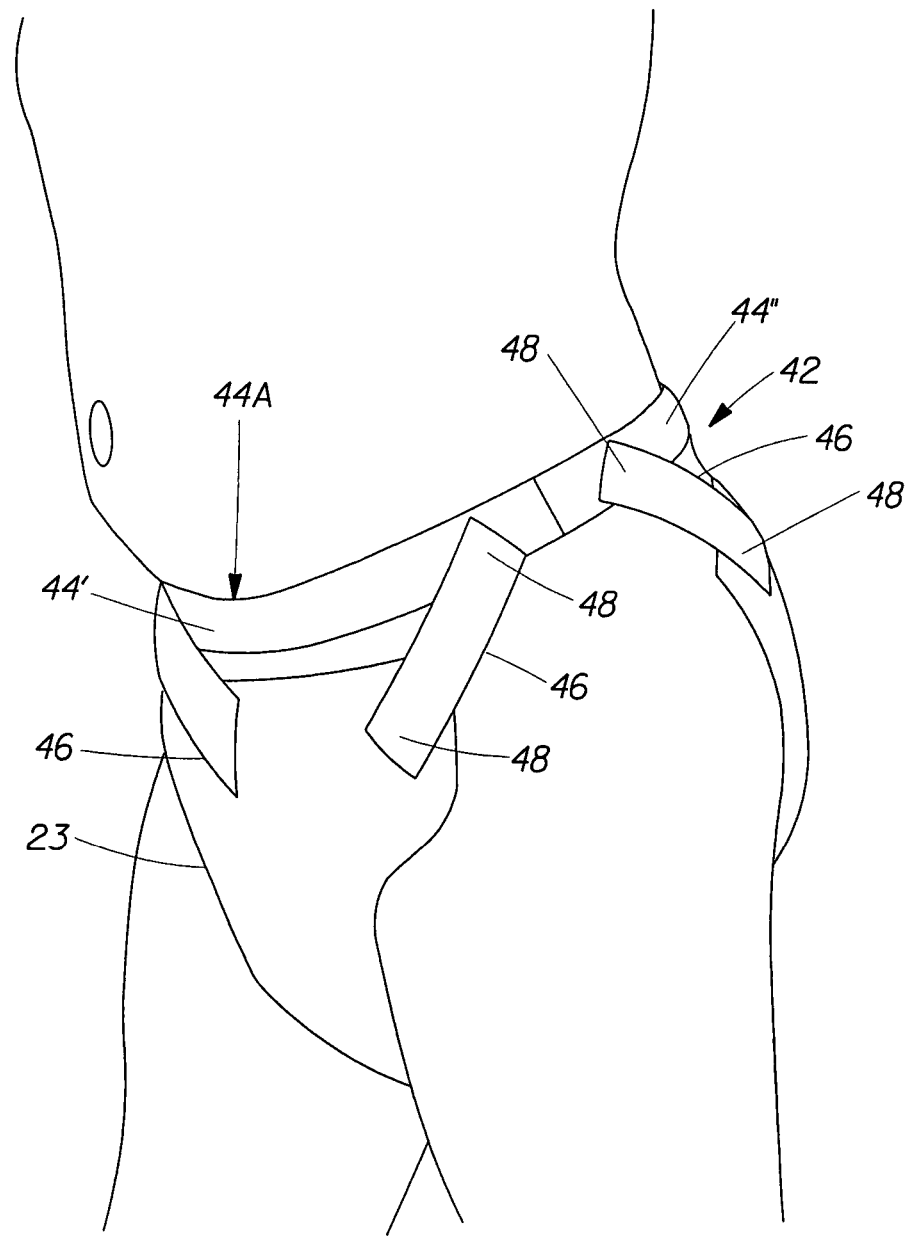
FIG. 2A illustrates a perspective view of an embodiment of an anchoring system joined to an absorbent core, for use in a disposable absorbent article, according to the present disclosure.
Figure 2B:
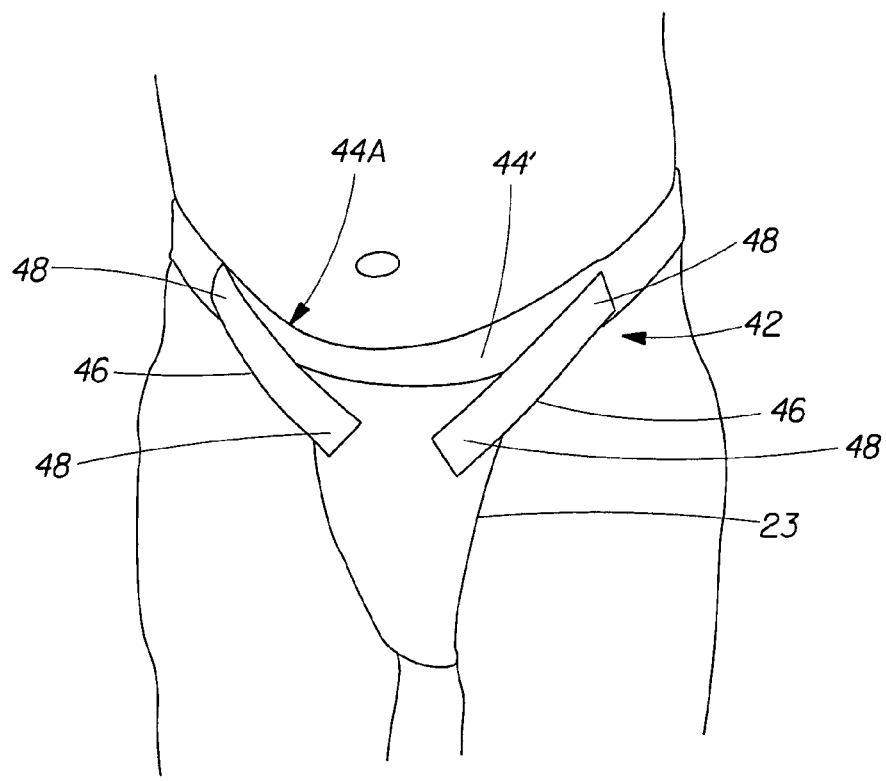
FIG. 2B illustrates a front view of the anchoring system and absorbent core of FIG. 2A, according to the present disclosure.
Figure 2C:
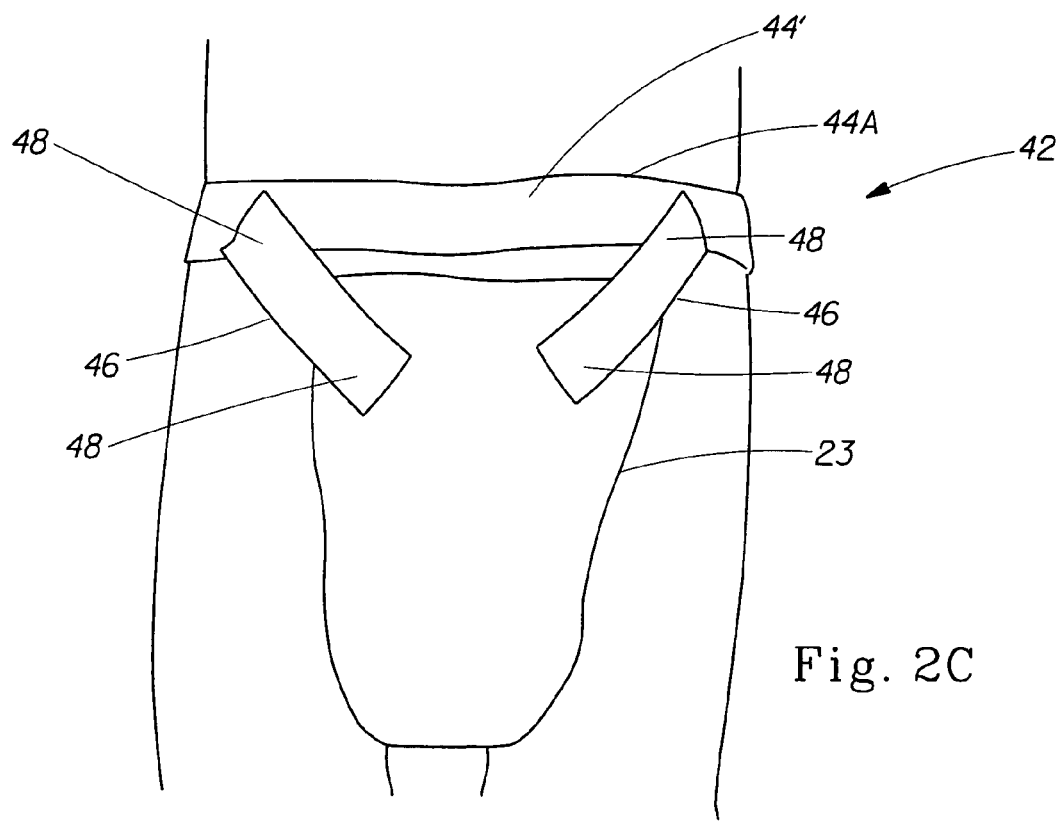
FIG. 2C illustrates a back view of the anchoring system and absorbent core of FIG. 2A, according to the present disclosure.

In some embodiments, the anchoring system 42 may include a pair of anchoring bands that, as used herein, refer to structural elements of the anchoring system of sufficient strength to carry the forces involved in anchoring. Anchoring bands 44' and 44" form a first circumferential anchoring member (CAM) 44A (see FIGS. 2A-2C) when the front and back of the diaper are joined at the sides to form a fastened diaper 20. FIGS. 2A-2C illustrate side, front, and back, views of the anchoring system 42 that forms inside the diaper 20 and independently supports the core assembly 23 (shown in FIG. 1A) when the diaper 20 is worn. Referring back to FIG. 1A, the anchoring bands 44' and 44" are capable of joining to surround the wearer's body at the lower torso region. As shown, in some embodiments, the anchoring bands 44' and 44" can be disposed longitudinally inboard of an elastic waistband 43 of the diaper 20.

The CAM 44 includes a first anchoring band 44' extending between opposing side edges 54 in the front waist region 36, and a second anchoring band 44" extending between opposing side edges 54 in the back waist region 38. The anchoring bands 44' and 44" are disposed at a location proximal the corresponding end edges 56. In the illustrated embodiment, the first anchoring band 44' converges from the side edges 54 to a midpoint (aligned with the longitudinal centerline 100) that is disposed further from the end edge 56 in the front waist region 36 than the anchoring band 44' at the side edges 54.

The second anchoring band 44" can be slightly curved such that the anchoring band 44" presents a convex surface edge with respect to the end edge 56 at the back waist region 38. As illustrated, the first and second anchoring bands 44' and 44" may be symmetrical with respect to the longitudinal centerline 100. One skilled in the art will appreciate that anchoring bands 44' and 44" can either be straight (e.g., extending substantially parallel to lateral centerline 110 or extending straight but along a direction that intersects the lateral centerline 110), can include more than one straight section extending along a direction that intersects a neighboring straight section, can include a curved section, or can include a combination of curved and straight sections. Furthermore, the anchoring bands 44' and 44" can have portions that are convex and/or concave with respect to the corresponding end edges 56.

Figure 1C:
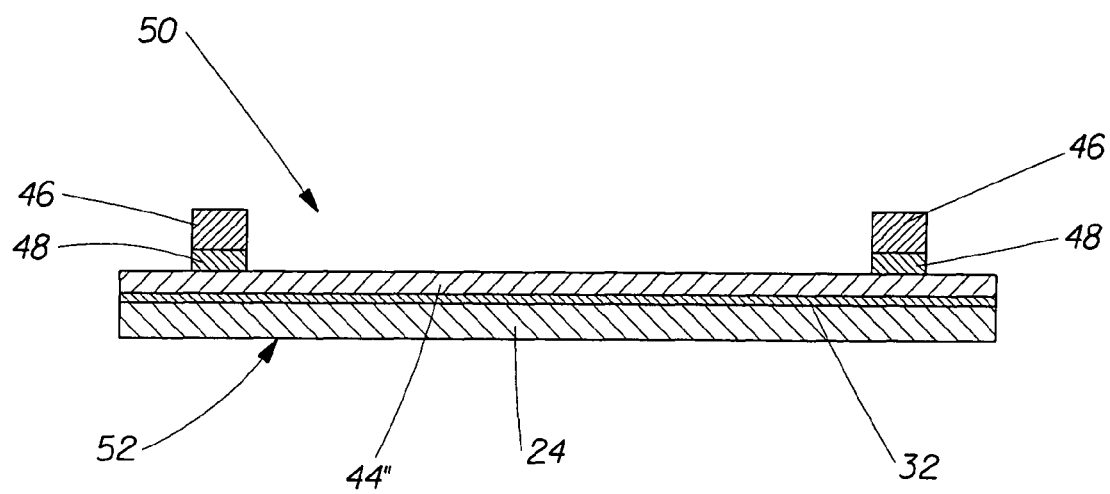
FIG. 1C illustrates a cross-sectional view of the disposable absorbent article of FIG. 1A, according to the present disclosure.

As shown in FIGS. 1B-1C, in some embodiments, the CAM 44 can be attached to the wearer-facing surface of the outer cover 24 via any suitable adhesive or cohesive or any suitable means known in the art. When the diaper 20 is preformed into a pant, the anchoring bands 44' and 44" can be operatively connected via side seams 34 or closure members to form the continuous circumferential anchoring member 44 that circumscribes the wearer's lower torso region.

The anchoring system 42, in some embodiments, may further comprise one or more load distribution element(s) 46 (LDE(s)). For example, as shown in FIG. 1A, a plurality of load distribution elements (LDEs) 46 can be connected to the core assembly 23 and the anchoring bands 44' and 44". The LDEs 46 can be joined to the anchoring bands 44' and 44" and the core assembly 23 at connection zones 48. The anchoring bands 44' and 44" include one or more connection zones 48 that are joined to the LDEs 46. As illustrated, in some embodiments, the connection zones 48 are the points where the LDEs 46 are joined to the CAM 44. As shown, in some embodiments, the CAM 44 may comprise an even number of connection zones 48 in the first waist region 36 and in the second waist region 38, e.g. two in the first waist region and two in the second waist region.

In one embodiment illustrated in FIG. 1A, four LDEs 46 may be connected to the four corresponding corners of the core assembly 23. In the embodiment illustrated in FIGS. 1A-1C and 2A-2C, the LDEs 46 may be connected to the garment-facing surface of the core assembly 23 via any suitable adhesive, cohesive, thermal bonds, RF bonds, pressure bonds, ultrasonic bonds, welds, stitches, or the like. Alternatively, the LDEs 46 can be connected to the inner (wearer-facing) surface of the core assembly 23, or to any of the individual components of the core assembly 23. In some embodiments, the LDEs 46 may extend laterally outward from the core assembly 23 and toward the corresponding end edge 56 and terminate at opposing ends that are joined to the inner (i.e., body-facing) surface of the CAM 44 at the connection zones 48 (see FIG. 1C). In some embodiments, the LDEs 46 may be joined to the outer-facing surface of the CAM 44. The LDEs 46 may be joined to the CAM 44 and to the core assembly 23 by any suitable means known in the art. Some suitable examples include adhesive, cohesive, or the like.

Additionally, in some embodiments, the LDEs 46 can either be attached discretely to the outer cover 24 or may be integral with the outer cover 24. For example, as shown, in some embodiments, the LDEs 46 may be joined to the CAM 44 at one end and to the core assembly 23 at the other, with the region in between being unbonded and free to stretch. Alternately, the LDEs 46 may have a relatively high force/modulus elastic that is either fully attached to or embedded in the outer cover 24. An example of a suitable approach to achieving the latter can be to print an elastomeric composition on the outer cover 24 via standard elastomeric printing techniques like gravure, offset gravure, flexographic, letterpress, screen, and inkjet printing, and via other elastomer deposition techniques like spraying and slot coating. Another example of a suitable approach can be to print thermoplastic non-stretchable materials on the outer cover 24 via standard thermoplastic printing techniques. The formation of CAMs, LDEs and/or anchoring bands integral with the outer cover 24 is discussed hereafter. Alternatively to attaching the LDEs to the CAM, the LDE(s) and the CAM(s) can also be made as a unitary structure, e.g. be made from the same material. Likewise, part of the core (e.g. the NWDL or the BLC) can be unitary with the LDE(s) and/or the CAM.

Referring to FIGS. 2A-2C, during use, when the core assembly 23 absorbs an excremental load, this incremental load gives rise to additional gravitational as well as inertial forces. For example, a gravitational load force is applied to the core assembly 23 which tends to push the absorbent assembly 23 downward. The absorbent assembly 23 transmits the gravitational load force to the LDEs 46 which in turn distribute the load force to the CAM 44A. The CAM 44A in turn, transfers the gravitational load force to the wearer's body (e.g., at the lower torso region). Part of the weight of the core assembly 23 (one quarter if the core and urine loading are symmetrical with respect to the longitudinal centerline and lateral centerline) can be transmitted through each LDE 46 to the CAM 44A.

For any given urine load, the tension in the LDEs 46 increases as the angle of the LDEs 46 with respect to the longitudinal centerline 100 (see beta shown in FIG. 1A,). Hence, the larger the angle that a given LDE 46 makes with respect to the vertical when the diaper 20 is donned on the wearer, the higher the tensile force that the LDE 46 will apply to the CAM 44A. If the CAM 44A stretches substantially under this tensile load, particularly between a connection zone 48 in the first waist region 36 and an adjacent connection zone 48 in the second waist region 38, the circumference of the CAM 44A may increase thereby causing the CAM 44A to lose some tension. Loss of tension by the CAM 44A may cause the CAM 44A to move down until the CAM 44A finds a new equilibrium location on the wearer's body. Accordingly, in certain aspects of the present invention, the portion of the CAM 44A between a connection zone 48 in the first waist region 36 and an adjacent connection zone 48 in the second waist region 38 may be elastic, extensile, or non-stretchable. In some embodiments, the portion of the CAM 44A between adjacent connection zones 48, i.e. connection zone in the first waist region and a connection zone in the second waist region, can be elongated by less than about 50 mm. In other embodiments, the connection zones 48 may have the same stretch properties as the rest of the stretchable portions of the CAM 44A.

The LDEs 46, in some embodiments, can be joined to the CAM 44A such that an angle beta (shown in FIG. 1A) defined between a given LDE 46 and the longitudinal centerline 100, can be between about 10 and 80 degrees or any individual number within the range. It should be appreciated, as is described in more detail below, that numerous alternatives to the embodiment illustrated in FIGS. 1A-1C are contemplated.

Because the generally downward forces applied to the core assembly 23 during use are transferred to the CAM 44A via the LDEs 46, the core assembly 23 can, in various embodiments, be supported without any additional core-supporting structure. Further, the performance of the anchoring system 42 can be enhanced if all other potential pathways between the core assembly 23 and all parts of the anchoring system 42 and the chassis are force-decoupled. With this arrangement forces generated at the core 26 may follow a pathway provided by the anchoring system 42 that bypasses the outer cover 24 at the crotch region 37 and at a portion of the front and back waist regions 36 and 38.

As will be described in more detail below, the anchoring system 42 may define a geodesic network when the diaper 20 is worn by the wearer in accordance with certain aspects of the invention. It should be appreciated that the LDEs 46 can be arranged in any desired manner such that they provide for the transmission of the weight (gravitational and inertial forces) of the core assembly 23 and any of its contents (e.g. the elastic forces of the BLC being part of the core assembly) to the anchoring system 42 thus permitting the outer cover 24 to be rendered biaxially stretchable or uniaxially stretchable without risk of substantial sagging and/or distension due to the loads received by the core 26 during use, especially if the core assembly is not stretchable or only stretchable to a lesser degree than the outer cover 24 The biaxial stretchability allows the outer cover 24 to conform to the wearer's body in an underwear-like manner.

In embodiments comprising the stretchable outer cover 24, the outer cover 24 can force-decouple a potential pathway between the core assembly 23 and the anchoring system 42 ensuring that the anchoring system 42 receives loads from the core assembly 23 only by the LDEs 46 as opposed to receiving loads from the core assembly 23 by both the LDEs 46 and the outer cover 24. In some embodiments, substantially all of the load from the core assembly 23 may be transferred to the CAM 44A via the LDEs 46. In order to achieve the force decoupling it may be desirable to minimize the coefficient of friction between (a) the outer cover and the core, and (b) the outer cover and the CAM and LDE.

Figure 3B:
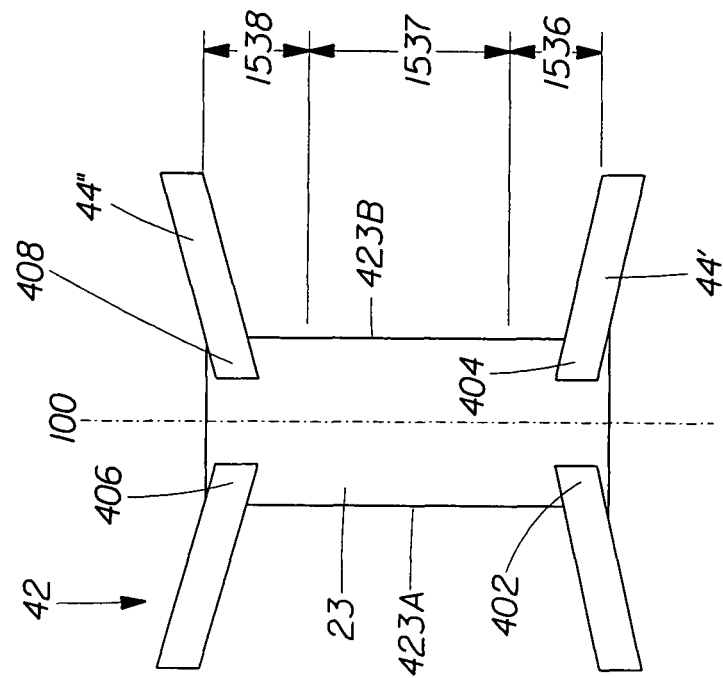
FIG. 3B illustrates a plan view of an embodiment of anchoring bands attached to an absorbent core, according to the present disclosure.
Figure 3A:
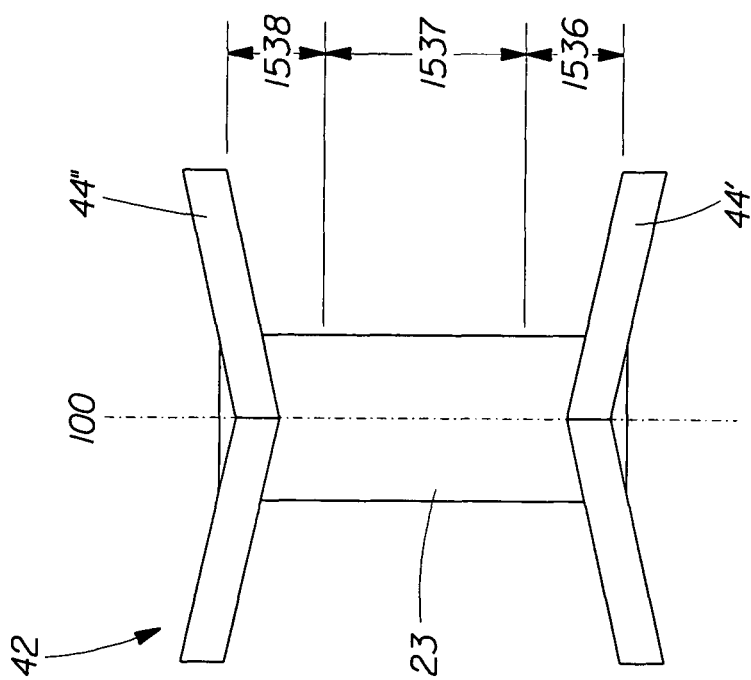
FIG. 3A illustrates a plan view of an embodiment of anchoring bands attached to an absorbent core, according to the present disclosure.

As shown in FIGS. 3A and 3B, in some embodiments, the anchoring system 42 may comprise anchoring bands 44' and 44" which are connected directly to the core assembly 23 without the use of LDEs. For example, the anchoring band 44' can be connected to the core assembly 23 in the first portion 1536 while the anchoring band 44" can be connected to the core assembly 23 in the second portion 1538. For embodiments comprising the anchoring system 42 of FIG. 3A, the assembled diaper 20 (shown in FIG. 1A) includes a continuous CAM 44A (shown in FIGS. 2A-2C). Specifically, for the anchoring system 42 of FIG. 3A, the CAM 44A (shown in FIGS. 2A-2C) is a closed loop and does not utilize a portion of the core assembly 23 to close the loop about the waist of the wearer.

In contrast, embodiments comprising the anchoring system 42 of FIG. 3B include a discontinuous CAM 44A. Specifically, for the anchoring system 42 of FIG. 3B, the CAM 44A is not a closed loop and utilizes a portion of the core assembly 23 as an anchoring system element to close the loop about the waist of the wearer. As shown, in some embodiments, the anchoring band 44' can be connected to the core assembly 23 in a first location 402 and a second location 404. The first location 402 can be laterally spaced from the second location 404. As shown, the first location 402 and the second location 404 can be disposed in the first portion 1536 proximate to a first longitudinal edge 423A and a second longitudinal edge 423B of the core assembly 23.

In some embodiments, the anchoring band 44" can be configured as shown in FIG. 3A or as shown in FIG. 3B. As shown in FIG. 3B, in some embodiments, the anchoring band 44" can be connected to the core assembly 23 at a third location 406 and a fourth location 408. The third location 406 can be laterally spaced from the fourth location 408. Similar to the first location 402 and the second location 404, the third location 406 and the fourth location 408 may be disposed in the second portion 1538 proximate to the first longitudinal edge 423A and second longitudinal edge 423B.

Figures 4A, 4B:
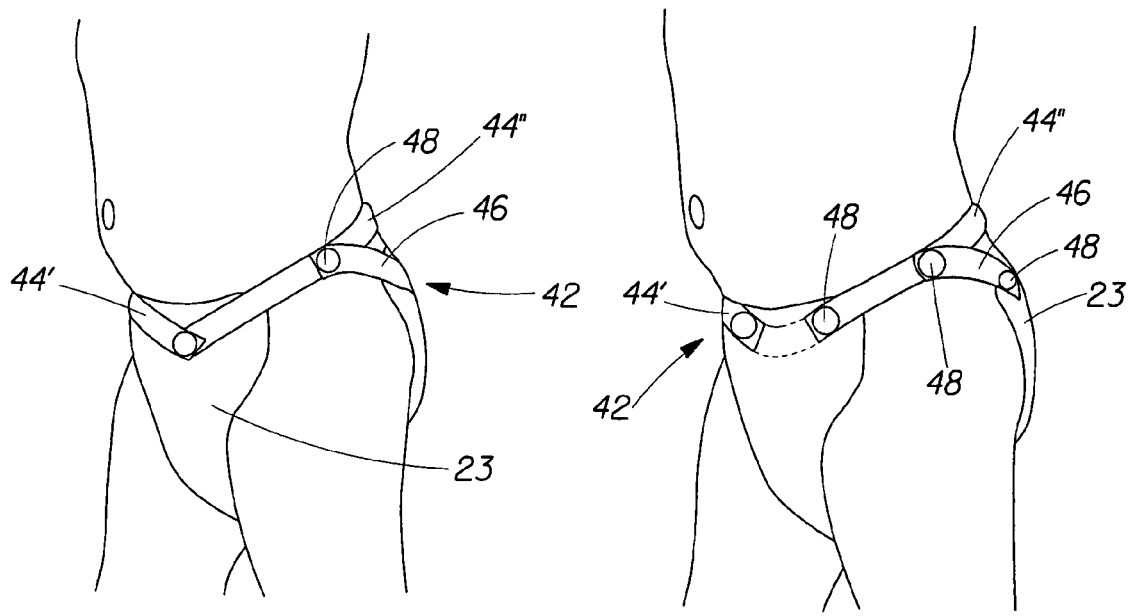
FIG. 4A illustrates a perspective view of an embodiment of an anchoring system joined to an absorbent core, for use in a disposable absorbent article, according to the present disclosure.
FIG. 4B illustrates a perspective view of an embodiment of an anchoring system joined to an absorbent core, for use in a disposable absorbent article, according to the present disclosure.
Figure 4C:
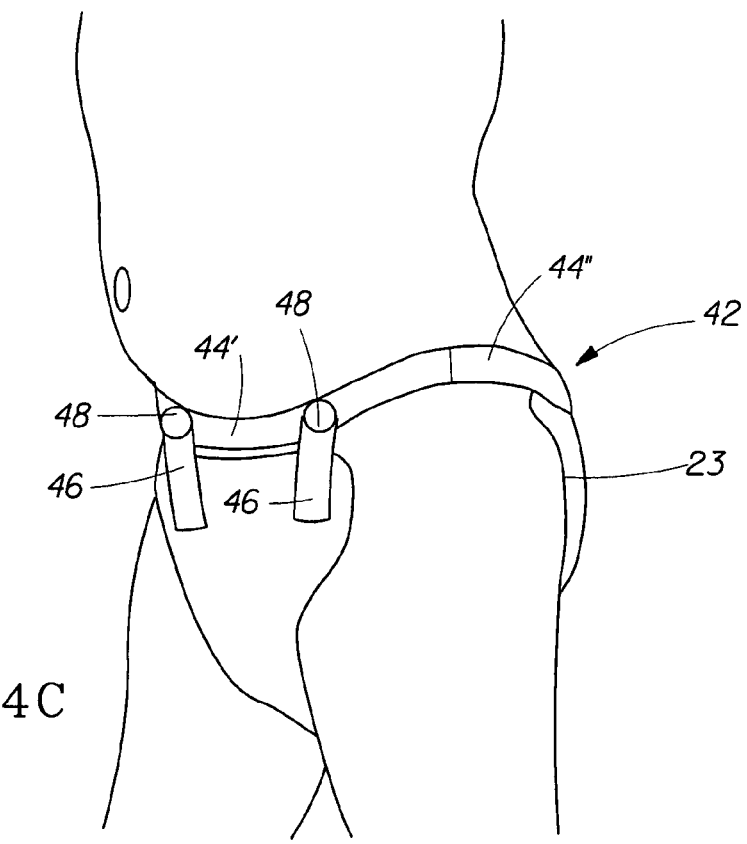
FIG. 4C illustrates a perspective view of an embodiment of an anchoring system joined to an absorbent core, for use in a disposable absorbent article, according to the present disclosure.

As shown in FIGS. 4A through 4C, embodiments are contemplated wherein the anchoring member 44' is connected directly to the core assembly 23 while the anchoring member 44" is joined to the core assembly 23 via LDEs 46 and vice versa. Connections directly to the core assembly 23 include those discussed with regard to FIGS. 3A and 3B. Similarly, embodiments are contemplated where the anchoring band 44' is configured as described in FIG. 3A while the anchoring band 44" is configured as described in FIG. 3B, or vice versa.

Figure 5A:
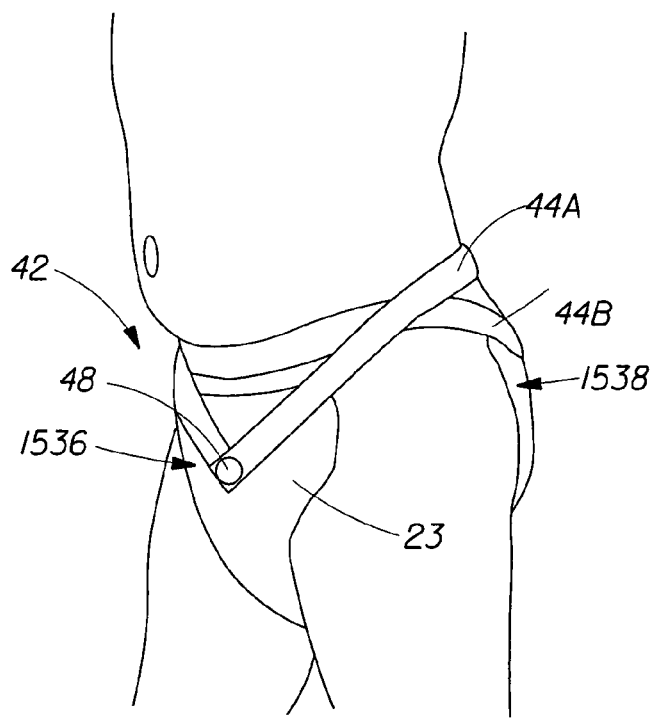
FIG. 5A illustrates a perspective view of an embodiment of an anchoring system joined to an absorbent core, for use in a disposable absorbent article, according to the present disclosure.
Figure 5B:
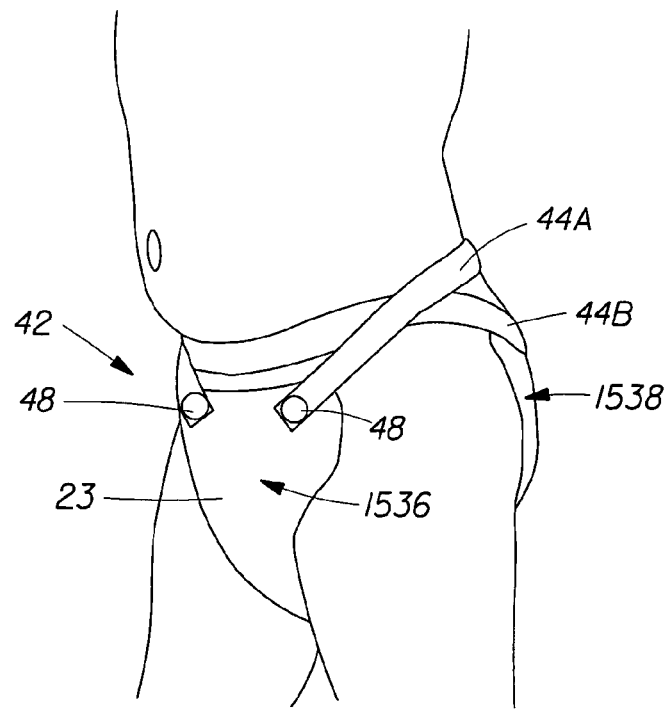
FIG. 5B illustrates a perspective view of an embodiment of an anchoring system joined to an absorbent core, for use in a disposable absorbent article, according to the present disclosure.

Embodiments are contemplated where the anchoring system 42 comprises more than one CAM. For example, as shown in FIGS. 5A and 5B, the anchoring system 42 may comprise a first CAM 44A and a second CAM 44B. The first CAM 44A can be connected to first portion 1536 of the core assembly 23 while the second CAM 44B is connected to the second portion 1538 of the core assembly 23. As shown in FIG. 4A, in some embodiments, a CAM can be continuous. In contrast, as shown in FIG. 4B, in some embodiments, the core assembly 23 can form an implied anchoring band to close the loop of a CAM. For the embodiment shown in FIG. 4B, a CAM can be connected to the core assembly as described with regard to FIG. 3B and the first location 402, second location 404, third location 406, and the fourth location 408. In some embodiments, the anchoring system may be configured as described with regard to FIG. 5A. However, instead of being connected to the core assembly 23, a CAM can be joined to the core assembly 23 via a plurality of LDEs.

With regard to FIGS. 5A and 5B, in some embodiments, the first CAM 44A can be joined to the second CAM 44B proximal to a point of intersection between the first CAM 44A and the second CAM 44B. By joining the first CAM 44A and the second CAM 44B to one another, each of the CAMs can provide lateral stabilization to the other CAM. The lateral stabilization can reduce the likelihood that the first CAM 44A and/or the second CAM 44B will move relative to the wearer during dynamic movement.

Figure 6:
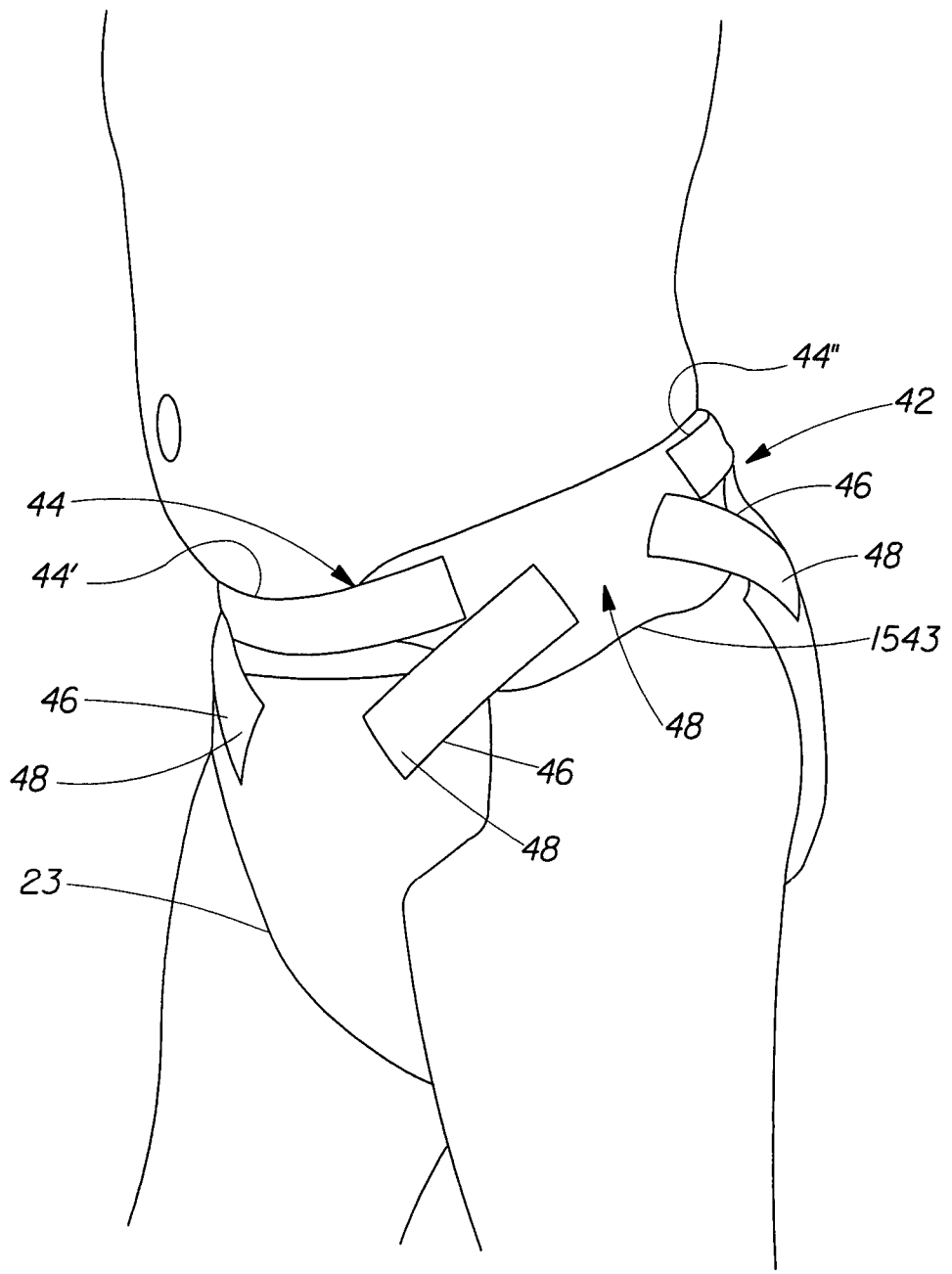
FIG. 6 illustrates a perspective view of an embodiment of an anchoring system joined to an absorbent core, for use in a disposable absorbent article, according to the present disclosure.

While the LDEs 46 may be directly connected to the CAM 44 as described above with reference to FIG. 1A, it should be appreciated that the present invention alternatively contemplates the CAM 44 connected to the LDEs 46 via an intermediate load element 1543 which may act as a connection zone 48, as illustrated in FIG. 6. As shown in FIG. 6, in some embodiments, the LDEs 46 may comprise elongated bands that are attached at one end to the core assembly 23 on either side of the longitudinal centerline 100 (and proximal thereto), and are connected at their other ends to the intermediate load element 1543. In turn, the intermediate load element 1543 may act as the connection zone 48 which joins the LDEs 46 to the corresponding anchoring band 44' or 44". The properties of the intermediate load element 1543 can be similar to the properties of the CAM 44, anchoring bands 44' and 44", and LDEs 46, discussed hereafter.

Figure 7B:
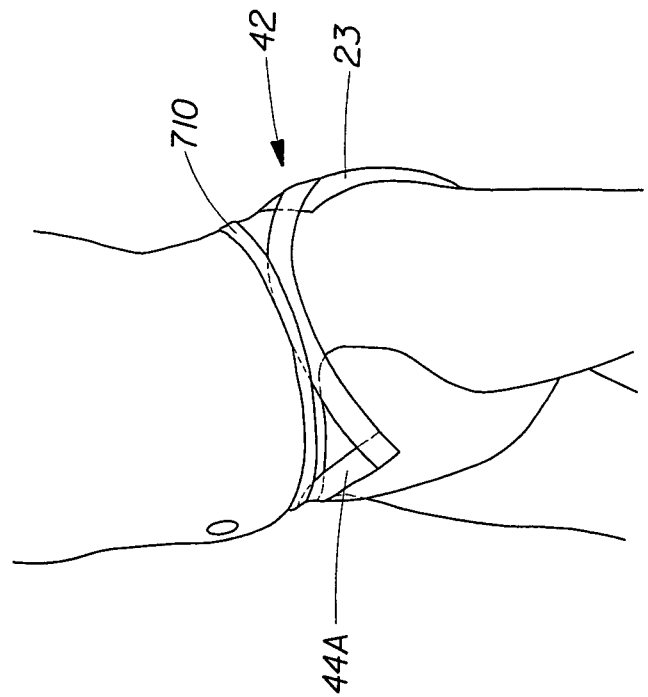
FIG. 7B illustrates a perspective view of an embodiment of an anchoring system joined to an absorbent core, for use in a disposable absorbent article, according to the present disclosure.
Figure 7A:
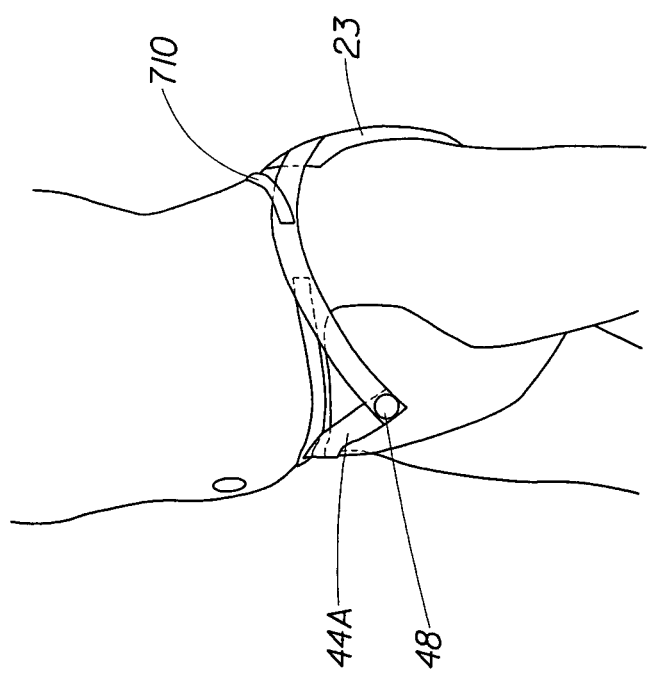
FIG. 7A illustrates a perspective view of an embodiment of an anchoring system joined to an absorbent core, for use in a disposable absorbent article, according to the present disclosure.

Other embodiments of the present invention include a stabilization band. For example, as shown in FIGS. 7A and 7B, the anchoring system 42 may comprise a stabilization band 710 which is joined to the first CAM 44A. As shown, in FIG. 7A, the stabilization band 710 may be discontinuous. Specifically, as shown, the stabilization band 710 may not be a closed loop independently from the first CAM 44A. Alternatively, in some embodiments, as shown in FIG. 7B, the stabilization band 710 may be continuous, i.e. a closed loop independently from the first CAM 44.

Regardless of whether the stabilization band 710 is continuous or discontinuous, the stabilization band can be joined to the first CAM 44A thereby providing lateral support to the first CAM 44A. For example, the stabilization band 710 can reduce the likelihood that a portion of the first CAM 44A will slide down the hip of the wearer during dynamic movement. In various embodiments, a stabilization band can be non-stretch or elastic.

Additionally, the first CAM 44A can be joined to the core assembly 23 as discussed heretofore. For example, the first CAM 44A may be directly connected to the core assembly 23 in the front portion 1536 (shown in FIG. 1A) and directly connected to the core assembly 23 in the back portion 1538 (shown in FIG. 1A). As another example, the first CAM 44A can be joined to core assembly 23 in the front portion 1536 (shown in FIG. 1A) and/or the second portion 1538 (shown in FIG. 1A) via LDEs 46 (shown in FIG. 1A). As yet another example, the first CAM 44A can be directly connected to the core assembly 23 in the front portion 1536 (shown in FIG. 1A) and/or the back portion 1538 (shown in FIG. 1A) as described heretofore with regard to FIGS. 3A and 3B, 4A and 4C, and 5A and 5B.

The CAMs of the present invention can be made from any suitable material known in the art. For example, the CAM can be an elastomeric material in any form, e.g. extruded film, elastic non-woven, scrim, slot-coated film, sprayed or melt-blown fibers, printed elastics, or any other suitable process known in the art for manufacturing elastomeric material. In embodiments comprising an outer cover (as described heretofore with regard to FIG. 1A), the CAM may be attached to the outer cover either on line during the diaper manufacturing process, or it may be incorporated into the outer cover during the outer cover manufacturing process. An example of the latter is elastomer printing, wherein, in a specific embodiment, the print pattern on the printing roll is such that the higher caliper region forms the higher-force CAM, while the lower caliper region forms the rest of the outer cover. Anchoring systems formed as a portion of the outer cover are discussed hereafter.

In some embodiments, the CAM may have a first cycle force greater than about 50 grams at about 15% strain. In some embodiments, the CAM may have a first cycle force of between about 75 grams and about 1000 grams or any individual number within the range. In some embodiments, the CAM may have a first cycle load of between about 100 grams and about 500 grams. In some embodiments, the CAM may have a first cycle load of between about 150 grams and about 300 grams. It should be noted that this force is measured at the actual width of the CAM.

The CAM may be of any suitable width known in the art. For example, in some embodiments, the CAM may vary in width from about 5 mm to about 75 mm or any individual number within the range. In some embodiments, the CAM may vary in width from about 10 mm to about 50 mm. In some embodiments, the CAM may vary in width from about 15 mm to about 35 mm.

It should be appreciated that the CAM can have a variable width and/or thickness along its length, either of which would produce discrete regions on the CAM having different stretch properties (e.g., that stretch to different extents). The variable width and/or thickness could be achieved, for example, using an elastomeric printing process appreciated by one having ordinary skill in the art.

The CAM has higher modulus (slope of the stress-strain curve) than the modulus of the outer cover to prevent excessive sagging with each increment of load. The CAM, in some embodiments, can have certain portions that are elastic and other portions that are either extensible or non-stretchable (i.e. elastic over one or more portions of its length and inelastic or non-stretchable over the remaining portions). For example, a section of the CAM that is connected to a non-stretchable core assembly need not be stretchable, since this core assembly would prevent the CAM from stretching.

The CAM stretches predominantly in the lateral direction. A key part of the invention is that CAM has a higher tensile force compared to the remainder of the outer cover. At 15% strain (first cycle), the ratio of lateral CAM force per unit width to the remainder of the outer cover or topsheet force per unit width is greater than 1.5, more preferably greater than 2, even more preferably greater than 5, and most preferably greater than 10.

In embodiments where the diaper is a pant, the CAM can be elastic in order to allow the diaper to stretch in the lateral direction during application, given that the initial diaper circumference can be preset. This desirability can be increased when a single size diaper is intended to fit a range of wearers in a given size. In embodiments where the diaper is a taped diaper, the size adjustability can be at least partially achieved by the fastener placement on a landing zone or other fastener receiving surface and, as a result, while the CAM can be elastic, a non-stretchable, or extensible, CAM is similarly feasible.

The LDEs 46, in some embodiments, may be non-stretchable so as to transfer the load forces at the core 26 to the connection zone 48 of the CAM 44. The LDEs of the present invention may comprise, in some embodiments an elastic material, an extensible material, and/or a non-stretchable material. The LDEs 46 may be formed utilizing any suitable material known in the art. For example, the LDEs 46 can be formed from nonwovens, films, elastomeric structures, and the like.

It should be appreciated that the LDEs 46 can alternatively be extensible or stretchable, in which case they preferably have a low strain force limit. For example, the LDEs 46 may be able to stretch to some low level of strain, e.g. 50%. Beyond the strain of 50%, for example, the slope of the stress strain curve can increase compared to the slope of the stress strain curve from 0% to 50% strain. Such materials may be beneficial in reducing wet core drooping due to wearer movements like walking and running. The low strain force limit can be achieved, for example, with stretch bonding, whereby an elastomeric film, filaments or nonwoven is stretched in the machine direction, bonded to a substrate web, such as a nonwoven, and allowed to retract and gather; or, as another example, via incremental stretching to a relatively small level of strain. For example, a nonwoven that comprises a mix of elastomeric and non-elastomeric fibers/filaments is not elastic. However, upon incremental stretching, the web may become elastic.

In general, incremental stretching can be used to release the stretch properties of a composite that comprises elastic and inelastic components, e.g. an elastic web laminated to an inelastic web. In accordance with certain aspects of the present invention, the low level of strain can be less than about 50%, alternatively less than about 40%, alternatively still less than about 30%, alternatively still less than about 25%, and alternatively still less than about 20% for a linkage that is between about 50 and about 150 mm long or any individual number within the range. The extensibility/stretchability of the LDEs permits the diaper 20 to expand in the longitudinal and lateral directions, thereby providing a conforming fit for a wider range of wearers that is improved with respect to conventional absorbent articles. Furthermore, extensible or elastic LDEs 46 can accommodate wearer movement during use, and further accommodate core swelling as loads are deposited in the core 26.

In some embodiments, the load of the LDE at 15% strain (first cycle) in the Hysteresis test is at least about 40 gm, preferably more than about 75 gm and most preferably greater than about 100 gm. In some embodiments, the LDEs 46 can have a width ranging from about 5 mm to about 50 mm. It should be noted that the sample width in the Hysteresis test should be the same as the width of the LDE. Also, the length direction of the LDE is the direction in which it is pulled in use. In some embodiments, the LDEs 46 and/or the CAM 44 may alternatively comprise a multiplicity of subcomponents, such as strands or filaments, having individual widths of less than 5 mm. In accordance with certain aspects of the present invention, in some embodiments, the LDEs 46 are less extensible (e.g., have a higher elastic modulus) than the outer cover 24 to reduce the ability for wearer movement to cause the core assembly 23 to bias the outer cover 24, e.g. cause the waist and/or leg perimeters to move with respect to the wearer.

Figure 8:
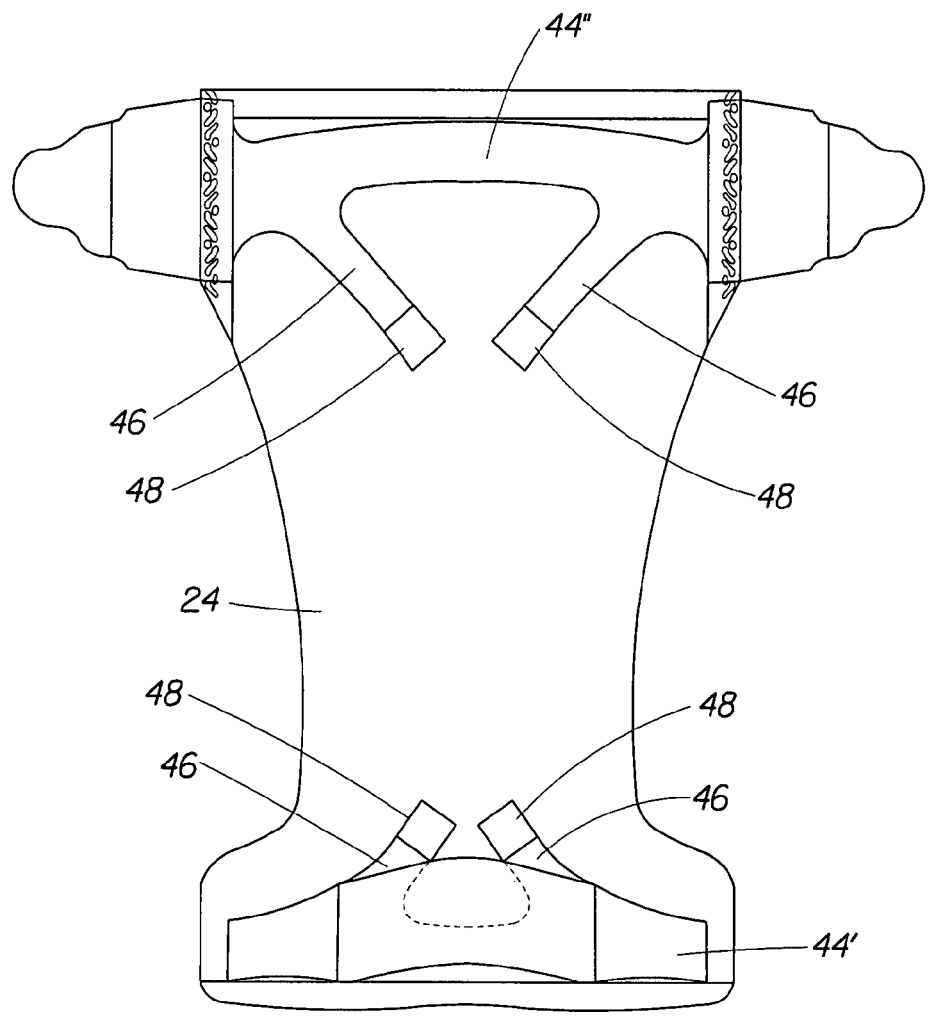
FIG. 8 illustrates a plan view of an embodiment of an anchoring system integrally formed into to an outer cover, for use in a disposable absorbent article, according to the present disclosure.

The integral formation of anchoring bands, CAMs, and/or LDEs as part of the outer cover is contemplated in some embodiments. For example, as shown in FIG. 8, in some embodiments, the LDEs 46 and/or the CAM 44 may be integrally formed in the outer cover 24 by differential incremental stretching of the outer cover 24. The core assembly has been omitted in FIG. 8 to show details of the integral anchoring system. As shown, in some embodiments, portions of the outer cover 24 that correspond to the LDEs 46, the anchoring band 44' and/or the anchoring band 44", are either not incrementally stretched or are stretched to a lesser extent compared to the rest of the outer cover 24. In some embodiments, a first portion of the CAM may be a discrete band or other separate element that is attached to the chassis 21, while a second portion of circumferential anchoring member is integral with the outer cover 24 to which the discrete band or other separate element is attached.

As shown in FIG. 8, in some embodiments, the outer cover 24 may be joined to the LDEs 46 at their respective connection zones 48. Additionally, in some embodiments, the LDEs 46 may be integral with the anchoring bands 44' and/or 44". For example, in some embodiments, the LDEs 46, the anchoring band 44', and the anchoring bands 44", may comprise a contiguous portion of underactivated or nonactivated area. As shown, in some embodiments, where the LDEs 46 are integral with the outer cover 24, the outer cover 24 can be joined to the core assembly 23 at the connection zones 48.

In accordance with one aspect of the present invention, if the LDEs 46 are formed from the outer cover 24, the LDEs 46 can be rendered extensible, non-stretchable, or elastic, such that the forces exerted on the core 26 are transferred to the CAM 44 while preventing the core 26 from substantially sagging. In embodiments, where the LDEs 46 and/or the CAM 44 are integral with the outer cover, the LDEs 46 and CAM 44 should have a higher modulus of elasticity than the modulus of elasticity of other portions of the outer cover 24 which do not comprise the LDEs 46 and/or the CAM 44.

The anchoring system of the present invention may have a higher modulus compared to the rest of the outer cover. This higher modulus can be achieved by using a higher caliper and/or higher performance elastomer, via differential incremental stretching, or over-bonding. Differential incremental stretching refers to incremental stretching of different regions of a substrate to different strain levels as described heretofore.

As described above, the circumferential anchoring member and/or LDEs can either be integral with the biaxially stretchable outer cover or be discretely attached to the biaxially stretchable outer cover. In some embodiments, an integral anchoring system may be created by differential incremental stretching of a biaxially stretchable outer cover precursor. The term "biaxially stretchable outer cover precursor" refers to a biaxially stretchable outer cover prior to incremental stretching. The term "biaxially stretchable" as used herein refers to the ability to stretch along two orthogonal axes that extend coplanar with the outer cover. The regions on the biaxially stretchable outer cover that correspond to the anchoring system either are not incrementally stretched or are stretched to a lesser extent compared to the rest of the biaxially stretchable outer cover.

In some embodiments, an integral anchoring system includes printing of an elastomeric composition in the areas where the circumferential anchoring member and/or LDEs are located on the biaxially stretchable outer cover precursor, followed by differential incremental stretching wherein the anchoring system components (i.e., LDEs and/or circumferential anchoring member) can be stretched to a lesser extent compared to the rest of the biaxially stretchable outer cover. The printing of the biaxially stretchable outer cover elastomer and the anchoring system elastomer onto the nonwoven substrate can be done in one step if they are the same chemistry, or in multiple steps if they are different chemistries. In some embodiments, non-stretch polymers can be printed and/or deposited to make integral anchoring system elements with non-stretch portions.

In some embodiments, the circumferential anchoring member and/or LDEs can also be attached to the biaxially stretchable outer cover discretely. An example is an on-line cut and slip process in which these elements are cut from an elastomeric film or a film-nonwoven laminate and attached to the biaxially stretchable outer cover.

In accordance with the methods described herein, an elastomer may be combined with a nonwoven web. The elastomer can be in the form of a film, a nonwoven, a crosshatch pattern, stripes in the lateral and/or longitudinal directions, stripes in any direction, or any other shape, and is laminated to a nonwoven.

In some embodiments, the elastomer may be printed onto the nonwoven web as described heretofore. The main advantage of printing is that it has the capability of delivering a very small amount of elastomer on the nonwoven, thus producing a low force member. For example, a pattern that has 1 mm wide stripes that are 4 mm apart will have about one fifth the force of a solid film. Another advantage of printing is that a small quantity of a high performance elastomer can be used to deliver the desired force and recovery properties, thus keeping manufacturing costs down. Regardless of the method by which the elastomer and nonwoven web are combined, the resultant web may be subjected to selective incremental stretching in the areas of the web which are intended to extend or stretch in use, i.e., during wearer movements. Any areas of the web intended to form a portion of the anchoring system (i.e., the CAM or LDEs) may be incrementally stretched to a lesser degree than the surrounding portions of the web. The above described can be applied to an absorbent article 120 of the embodiment of FIG. 13A and to the absorbent article 20 discussed heretofore.

The incorporation of anchoring systems into the articles of the present invention enables the articles to fit higher on the body initially (i.e., they do not "snap back" as much once application tension is released), fit a broader range of wearer "rises" (i.e., especially when biaxial outer cover stretch is employed such that the product can adjust in the longitudinal direction) and have a better sustained fit. It has been found that these effects enable the reduction in the as-manufactured longitudinal dimension (or "pitch") of the articles of the present invention. This provides these articles a more underwear-like appearance in their bi-folded state (i.e., when folded at their lateral centerline only) since they have an aspect ratio (folded height to width) similar to underwear. The articles of the present invention may have an aspect ratio of from between about 1.2 and about 0.7.

Outer Cover

As discussed previously, the outer cover may be stretchable in one or more directions, elastic in one or more directions, or non-stretchable. The side edges 54 of the outer cover 24 create perimeters about the legs of a wearer, and similarly, the end edges 56 of the outer cover 24 create a waist perimeter about the wearer. These perimeters can move relative to the anchoring system 42, thereby changing the distances between the perimeters and the anchoring system 42. For example, from a neutral standing position, these distances increase particularly in the back region when the knees are raised or the wearer bends forward at the waist.

In some embodiments, the waist and/or leg perimeters can be force-decoupled from the anchoring system 42 by a biaxially stretchable outer cover 24, or "BSOC", that is designed to minimize forces that arise between the waist or leg perimeters and the anchoring system 42 from movement of the legs and spine relative to the pelvis. In contrast, if the outer cover 24 were non-stretchable, such movements may encumber the wearer, or such movements may cause the perimeters to move relative to the waist and leg regions of the wearer. It will be thus appreciated that the anchoring system 42 and BSOC enables the diaper 20 to achieve an enhanced, more comfortable and underwear-like fit relative to conventional diapers. Embodiments are contemplated where the outer cover 24 is stretchable along one direction (e.g. the lateral, the transverse direction, or any other direction). In these embodiments, the waist and/or leg perimeters can similarly be force-decoupled from the anchoring system 42.

The outer cover, in some embodiments, can be impervious to liquids (e.g., urine) and manufactured from a thin plastic film or a nonwoven web, although other flexible liquid impervious materials which are compliant and will readily conform to the general shape and contours of the human body can also be used. Additionally, in some embodiments, the outer cover 24 may comprise a laminated structure.

The outer cover may be generally positioned such that it can be at least a portion of the garment-facing surface of the diaper. The outer cover can prevent the exudates absorbed and contained within the diaper from soiling articles that can contact the diaper, such as bed sheets and undergarments, in some embodiments. Suitable outer cover materials include films such as those manufactured by Tredegar Industries Inc. of Terre Haute, Ind. and sold under the trade names X15306, X10962, and X10964. In various embodiments, the outer cover can include an inelastic nonwoven. The outer cover can be a thermoplastic film having a thickness of from about 0.012 mm (0.5 mil) to about 0.051 mm (2.0 mils). Another example of a suitable film which can be utilized in the outer cover 24 includes a 0.5-1.0 mil (0.0005-0.001") thick Vistamaxx (elastomeric polypropylene from ExxonMobil). In some embodiments, elastomeric polypropylene based compositions are disclosed in WO 2005/052052 to ExxonMobil and in WO 2005/097031 to Procter & Gamble. The elastomeric composition may also include fillers like titanium dioxide for improving opacity and calcium carbonate for breathability. The elastomeric polypropylenes may also be blended with styrenic block copolymers, semicrystalline polyolefins or sub-micron inorganic particles.

In some embodiments, the outer cover 24 may comprise an elastic nonwoven. In some embodiments, the outer cover 24 may comprise a laminate including an elastic nonwoven and a plastic film, for example, polyethylene film. In some embodiments, the outer cover 24 may comprise a laminate including an elastic film and a non-elastic nonwoven. In some embodiments, the outer cover 24 may comprise a laminate including printed elastics. In some embodiments, the outer cover 24 may comprise a laminate including an elastic in the form of a scrim-like structure or a crosshatch pattern that is joined between two layers of a nonwoven or between a nonwoven and a breathable film (e.g. polyethylene film), etc.

The elastomeric film examples provided above can be laminated to at least one layer of non-elastomeric or extensible nonwoven using spiral glue. Additionally, this laminate can be incrementally stretched in a machine direction and then in a cross machine direction thereby forming a biaxially stretchable elastic laminate. A suitable example of a nonwoven which can be utilized in the outer cover 24 includes DAPP. A suitable DAPP nonwoven is sold under the designation Softspan 200 available from BBA Fiberweb, Brentwood Tenn. In some embodiments the DAPP can be joined to an elastic element, e.g. elastomeric scrim and joined to a polyethylene film. In some embodiments, the DAPP can be joined to an elastic element, e.g. elastomeric scrim and joined to another DAPP nonwoven.

Outer cover laminates, such as those described above, wherein the elastomeric component is combined with another web in a relaxed, unstretched state, are referred to in the art as "zero-strain laminates". While in some embodiments, the zero-strain laminate may be inherently stretchable in a virgin state, the stretch properties of these materials are usually released or improved by mechanical activation, or incremental stretching, such as ring rolling or SELFing. Alternatively, pre-stretched laminate materials may also be employed as outer cover materials in the present invention. Pre-stretched elastomeric outer covers are formed by applying an elastomeric material, e.g., strands or films, to a substrate while the elastomeric material is in a prestrained state, and subsequently allowing the laminate to relax and contract. Pre-stretched biaxially stretchable outer cover materials may be formed by applying pre-tensioned elastomeric elements in at least two different directions, preferably, but not necessarily, aligned with the longitudinal and lateral axes of the article. In certain embodiments, outer covers of the present invention may include both zero-strain and pre-stretched elastomers. For example, a pre-tensioned elastomeric element may be affixed to a zero-strain elastomeric laminate either parallel to the zero strain laminate's primary direction of stretch or at an angle thereto.

In some embodiments, the outer cover 24 may comprise an elastomeric layer which includes an elastomeric adhesive, e.g. a hot melt pressure sensitive adhesive. In these embodiments, additional adhesive may not be needed to bond the layers of the laminate together. However, if the elastomeric material does not have good adhesive properties, additional adhesive may be utilized.

In some embodiments, the outer cover 24 may have a low force at a specific elongation as measured by the Hysteresis Test (50% Maximum Strain). Since the outer cover can have different stretch properties in different directions, stretch properties in the Hysteresis Test are measured in the longitudinal direction (machine direction), lateral direction (cross machine direction) and in a direction that is parallel to the length direction of the anchoring band. In some embodiments, the outer cover 24 may have a first cycle force less than about 20 gm/cm at 15% strain. In some embodiments, the outer cover 24 may have a first cycle force less than about 15 gm/cm at 15% strain. In some embodiments, the outer cover 24 may have a first cycle force less than about 10 gm/cm at 15% strain.

Additionally, in some embodiments, the outer cover 24 may also have a percentage set (as measured by the Hysteresis Test) which is less than about 40% after about a 50% load Hysteresis Test. In some embodiments, the outer cover 24 may have a percentage set which is less than about 30% or in some embodiments, less than about 15%.

In some embodiments, the outer cover 24 may be sufficiently breathable. For example, in some embodiments, the outer cover 24 can be constructed to be permeable to at least water vapor and can have a moisture vapor transmission rate (MVTR) of at least 1000 $g/m^2/24$ hr., preferably at least 1500 $g/m/24$ hr., more preferably at least 2000 $g/m^2/24$ hr., and even more preferably at least 3000 $g/m^2/24$ hr. In other embodiments, the outer cover has an MVTR of at least about 7000 $g/m^2/24$ hr. In some embodiments, the outer cover 24 may have a moisture vapor transmission rate of from about 1000 to about 8000 $g/m^2/24$ hr. or any individual number within the range. Some breathable backsheet materials are described in greater detail in PCT Application No. WO 95/16746; U.S. Pat. No. 5,938,648; U.S. Pat. No. 5,865,823; and U.S. Pat. No. 5,571,096. Other suitable exemplary materials and a suitable test method for measuring the MVTR is described in U.S. Pat. No. 6,448,467. Additionally, in some embodiments, the outer cover 24 may comprise underwear-like texture/aesthetics. One aspect of underwear like aesthetics is gloss (as measured according to ASTM D2457-97) to give a pleasing mate look (not plastic like). A gloss value of 7 gloss units or less has been found desirable. Embossing and/or matte finishing improves the outer covers gloss.

The outer cover 24, in some embodiments, may have sufficient opacity such that exudates discharged into a core assembly 23 cannot be readily perceived from a vantage point external to the diaper 20. Also, the outer cover may have sufficient opacity to prevent the skin from being seen in the non-core areas of the diaper. In order to increase the opacity of biaxially stretchable outer cover elastic nonwovens, in some embodiments, at least one meltblown may be incorporated into the spunbond web. The meltblown layer may consist of nano-fibers. The meltblown layer may have a basis weight of between about 1 gsm and about 20 gsm or any individual number within the range. In some embodiments the meltblown layer may have a basis weight of between about 4 gsm and about 15 gsm and may comprise various combinations of elastomeric and plastic polymeric resins. Higher elastomeric content may be preferred when higher depths of activation (incremental stretching) are required and/or when lower permanent set values in the outer cover are desired. Elastomeric and plastic polyolefin combinations may utilized in some embodiments to optimize the cost/performance balance. In some embodiments, the elastomeric component may comprise a very low crystallinity polypropylene grade such as those commercialized by ExxonMobil under the tradename Vistamaxx. Additionally, the elastic nonwoven structure may also include another spunbond layer that does not provide significant elastic recovery, yet possesses sufficient extensibility to survive the activation process. Some suitable examples of such extensible spunbond nonwoven layers are disclosed in WO 2005/073308 and WO 2005/073309.

Other exemplary breathable materials can include materials such as woven webs, nonwoven webs, polymeric films such as thermoplastic films of polyethylene or polypropylene, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. An exemplary, suitable outer cover is disclosed in U.S. Pat. No. 6,107,537.

All or a portion of the outer cover can be ring-rolled and thus rendered highly extensible as described in U.S. Pat. No. 5,366,782 (issued Nov. 22, 1994 to Curro, et al). Specifically, a ring-rolling apparatus includes opposing rolls having intermeshing teeth that incrementally stretch and thereby plastically deform the material forming outer cover (or a portion thereof) thereby rendering the outer cover extensible in the ring-rolled regions. In some embodiments, the outer cover can be ring-rolled in a portion of at least one of the front or back waist regions while other regions may comprise a structured elastic-like formed web material or virgin or unactivated regions. Similarly, the chassis can be ring-rolled across the entire width in one or both of the waist regions or alternatively can be ring-rolled over only a portion of the chassis width. Ring rolling can be performed in one or multiple directions. For example, to make a biaxial stretchable outer cover, the nonwoven-elastic laminate can be first activated in, say, the lateral direction, and then in the longitudinal direction. Alternatively, the nonwoven-elastic laminate may be activated in any two directions aligned with, or at angles to, the longitudinal and/or lateral axes of the article. For example, the laminate may be activated plus and minus 45 degrees from the longitudinal axis. Alternatively, the laminate may be activated at plus 60 and minus 30 degrees from the longitudinal axis.

Figure 13A:
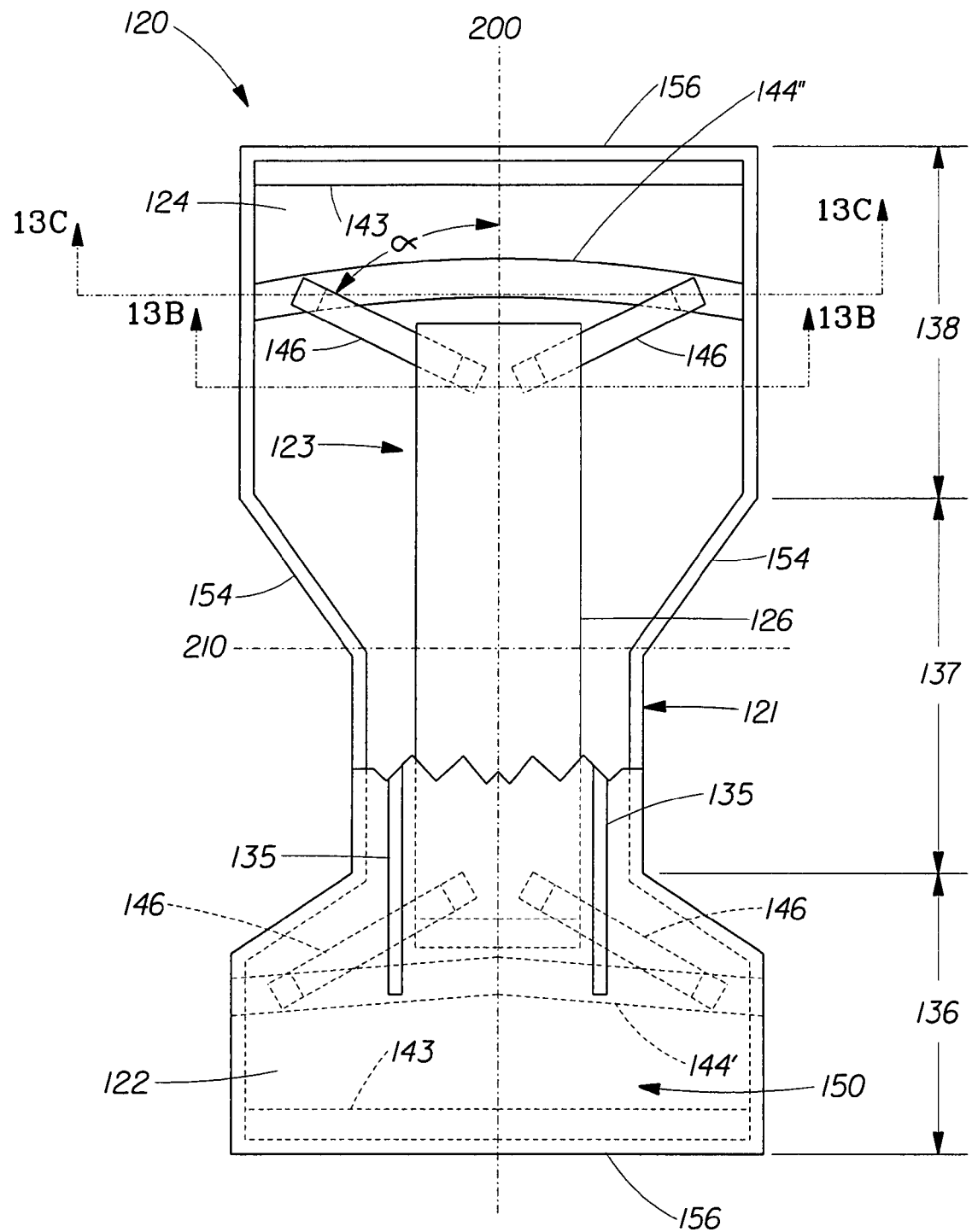
FIG. 13A illustrates a plan view of an embodiment of disposable absorbent article with an absorbent core and an anchoring system, according to the present disclosure.

Alternatively, the outer cover can comprise a structural elastic-like film (SELF) web that is stretchable along one or more of the longitudinal and lateral axes 200 and 210 (in FIG. 13A). SELF webs suitable for the present invention are more completely described in the commonly assigned U.S. Pat. No. 5,518,801 entitled "Web Materials Exhibiting Elastic-Like Behavior" issued to Chappell et al. on May 21, 1996.

Other suitable materials and/or manufacturing techniques can be used to provide a suitable outer cover including, but not limited to, surface treatments, particular film selections and processing, particular filament selections and processing, etc. The outer cover can be embossed and/or matte finished to provide a more clothlike appearance.

As described above, the biaxial stretchable outer cover, in some embodiments, has a low force, recoverable stretch (for instance, less than about 15 g/cm at a strain of 50%), similar to a cotton underwear. Such an outer cover can be made in several ways (e.g. via elastomeric nonwovens, printed elastics, spraying, and lamination). Nonwovens that predominantly have elastomeric fibers or filaments have a rubbery feel and are generally not desired by consumers. Since the stretchability of the outer cover occurs at low forces, it is possible to use a blend of elastomeric, e.g., very low crystallinity elastomeric polypropylene, and plastic, e.g., polypropylene, filaments. Exemplary structures are discussed in WO 2005/065680; WO 2005/052052; and WO 2005/097031. Advantages to using such a blend include the fact that the thermoplastic fibers help improve the feel of the outer cover 124 to the wearer/user. Additionally such a blend provides a force limit, as the nonwoven is incrementally stretched in order to release the stretch properties. An alternative method for fabricating the biaxially stretchable outer cover is to provide an elastomeric nonwoven structure that comprises bicomponent fibers having an elastomeric core and a thermoplastic sheath. Exemplary structures are discussed in U.S. Pat. No. 6,225,243; U.S. Pat. No. 5,470,639; and U.S. Pat. No. 5,997,989. This nonwoven may also have improved feel.

In both the above methods, the elastomeric nonwoven can be incrementally stretched to release the stretch. The nonwoven biaxial stretchable outer cover can be carded, spunbond, SMS (sponbond-meltblown-spunbond), or otherwise fabricated. The fine fibers of the meltblown layer in the SMS structure provide enhanced opacity, a desirable feature in outer covers. Replacing the meltblown layer with nano fibers may further increase the opacity of the outer cover.

The biaxially stretchable outer cover can also be made by elastomer printing, spraying, slot coating, meltblown or film lamination. Printing includes gravure, flexographic, letterpress, screen, digital, or the like. Some suitable examples of printing are described in U.S. Application Publication No. 2003/0088220A1; U.S. Application Publication No. US 2003/0088228A1; U.S. Application Publication No. 2003/0091807A1; U.S. Application Publication No. 2004/0193133A1; U.S. Application Publication No. 2004/0222553A1; U.S. Application Publication No. 2005/0214461A1; U.S. Application Publication No. 2003/0084996A1; U.S. Application Publication No. 2003/0084996A1; U.S. Application Publication No. 2003/0087059A1; U.S. Application Publication No. 2003/0087098A1; U.S. Pat. No. 6,875,710; and U.S. Pat. No. 6,942,894.

Spraying includes standard techniques for hot melt adhesive spraying, e.g. spiral, zig-zag pattern, ITW/s Omega pattern, meltblown, etc. An elastomeric film can be bonded to a nonwoven by extrusion or adhesive lamination. Preferably, the elastomeric film is breathable.

In accordance with certain aspects of the invention, various materials can be used to provide a biaxially stretchable outer cover in accordance with various embodiments of the present invention. When constructing the biaxially stretchable outer cover, various desirable features include the following:

Mechanical properties (as expressed in terms as measured in a Hysteresis test) during multiple medium-strain stretch-recovery cycles; As well as the ability to survive high-strain-rate medium depth of engagement Mechanical Activation in both machine direction and cross direction without pinhole);

Durability (low Fuzz, high Ultimate Strength);

Visuals (white color, high opacity, cotton-ribbon-like texture, printable, gloss);

Liquid Barrier properties in some embodiments (absence of pinholes or any other signs that could signal the possibility of outer cover leakage); and Low cost.

Variations in specific targets may be found depending upon whether the design is for a pant or a taped diaper. For instance, as is described in more detail below, one embodiment of a taped diaper design has an integrated anchoring system built into the biaxially stretchable outer cover which is created by differential activation (an area of the biaxially stretchable outer cover is intentionally left un-activated). Therefore, the development of the outer cover material takes into account performance targets for both pre- and post-activation states. The pant design may have more stringent upper limits for the CD stretch load of the biaxially stretchable outer cover in order to maintain easy diaper application.

The biaxially stretchable outer cover preferably has mechanical and/or elastic properties as described herein, as well as the ability to survive high-strain-rate mechanical activation (i.e., incremental stretching) in both the longitudinal and lateral directions without pinhole formation. Laminates which exhibit reduced pinholes from activation are described in U.S. application Ser. No. 11/361,918, entitled, "Method of Making Laminate Structures for Mechanical Activation", filed on Feb. 24, 2006, on behalf of Anderson et al. Additionally, the outer covers of the present invention preferably have a low tendency to fuzz, have high opacity, and are printable via printing processes common to the art.

The biaxially stretchable outer cover may be formed from any elastic or extensible web material or composite as known in the art. The biaxially stretchable outer cover may comprise an elastic nonwoven, an elastic nonwoven laminated with an extensible and/or elastic film or scrim, an extensible nonwoven laminated with an elastic film or scrim, a web comprising an elastomer pattern printed on an elastic and/or extensible nonwoven, variants of any of the preceding materials at least a portion of which is mechanically pre-strained, or any other elastic or extensible materials as known in the art.

In some embodiments of the present invention, the biaxially stretchable outer cover comprises only an elastic nonwoven. In these embodiments the total basis weight of the outer cover may be less than about 50 gsm, preferably less than about 40 gsm, and more preferably less than about 35 gsm. The outer cover material may comprise a spunbond fabric and be produced under conditions that promote optimal bond strength in order to provide sufficient strength and durability to the outer cover. Elastic nonwoven outer covers include at least one elastomeric material in a sufficient amount to provide a minimal desirable amount of recovery. Examples of suitable spunbond nonwovens are described in U.S. Pat. Nos. 5,470,639 and 5,997,989. In some embodiments of the present invention, the elastic nonwoven comprises elastic/plastic bicomponent fibers, examples of which are described in U.S. Pat. No. 6,225,243 and WO2006/017674, to provide the outer cover material with better hand/feel properties and improved spinnability. The outer cover material may also comprise webs, i.e., as disclosed in WO 2005/065680, formed of mixed elastic fibers (e.g., thermoplastic polyurethane elastomer) and plastic (e.g., polyolefins such as polypropylene) fibers, said nonwovens having good elastic recovery and tactile properties after being subjected to mechanical activation, such as Vistamax™ available from Exxon Another suitable elastic component is very low crystallinity elastomeric polypropylene. Other suitable examples of spunbond elastic nonwovens are disclosed in WO 2005/052052 and WO 2005/097031. In embodiments wherein the elastic nonwoven outer cover comprises mixtures or composites of both elastic and plastic materials, the ratio of the elastic to plastic components can be tailored to provide a desirable balance of both stretch/recovery characteristics and strength/toughness requirements. High toughness is desirable to maximize the ability of the web to survive mechanical activation in both the longitudinal and lateral directions.

Other exemplary materials suitable for the outer cover are disclosed in U.S. Pat. No. 6,896,843; U.S. Pat. No. 6,225,243; U.S. Pat. No. 5,997,989; U.S. Pat. No. 5,952,252; U.S. Pat. No. 5,695,849; U.S. Pat. No. 5,470,639; U.S. Pat. No. 5,405,682; WO 2005/052052; WO 2004/065680; WO 2006/017674; US 2004/0132374; US 2004/0110442; US 2003/0162458; U.S. Pat. No. 6,811,871; U.S. Pat. No. 6,103,647; U.S. Pat. No. 5,635,290; and U.S. Pat. No. 5,540,976.

In some embodiments of the present invention, the biaxially stretchable outer cover may comprise a laminate of elastic nonwovens, such as those described in the preceding section, and an extensible film. In this embodiment, a thin extensible polyolefin film layer is laminated onto the elastic nonwoven described above. Although higher basis weights are contemplated in certain embodiments, the basis weight of the film may be no more than about 22 gsm, preferably no more than about 20 gsm, and more preferably no more than about 18 gsm in order to minimize the cost of the laminate. The film may be combined with the elastomeric nonwoven via adhesive lamination, extrusion lamination, or any other suitable means of combining webs as known in the art. The film may preferably be extensible in both longitudinal and lateral directions and able to survive a mechanical activation (i.e., incremental stretching) process without pinhole formation over the relevant range of activation strains. The film may preferably be breathable, as discussed previously, whether the breathability originates from activation-induced microporosity or virtually invisible pinholes. The film may be either extensible, i.e. plastic, or it may be plastoelastic and exhibit partial recovery, hence participating in the elastic recovery process. Examples of "plastic" films include films comprising standard filled polyethylene resins, e.g. those disclosed in WO 2006/017518. Examples of the use of plastoelastic film formulations are disclosed in WO 2005/097031. The presence of the film laminated onto the stretch NW contributes to create highly desirable visuals such as high opacity and high texture without the need for incorporating the type of meltblown layer described above. Alternatively, the film may comprise high-performance elastomers such as Kraton-based elastomers. Further examples of elastic nonwoven/extensible film laminates suitable for the present invention are disclosed in WO 2005/017518; US 2005/0124952; U.S. Pat. No. 6,811,865; U.S. Pat. No. 6,623,837; and U.S. Pat. No. 6,096,668.

In some embodiments, the film can be the component that exhibits at least partial recovery upon stretching. The nonwoven may be an extensible spunbond or a necked/gathered spunbond of the types described above. As described above, in some embodiments, the basis weight of the film may be no more than about 22 gsm, preferably no more than about than 20 gsm, more preferably no more than about 18 gsm in order to minimize the cost of the laminate as well as minimize the force required to stretch the BSOC up to 50% strain. The film may be combined with the nonwoven either via adhesive lamination or via extrusion lamination. The film should be selected as described above such as to survive an incremental stretching process without pinhole formation over the relevant range of activation strains. The film may be breathable as described herein. An example of a filled elastic polyethylene blend film is disclosed in U.S. Pat. No. 6,909,028. Preferred elastomeric polypropylene-based compositions are disclosed in WO 2005/052052 and in WO 2005/097031. Blends of elastomeric polypropylenes with either styrenic block-copolymers, semicrystalline polyolefins or sub-micron inorganic particles can be used to enhance the stress-strain and hysteresis properties of the laminate. For example, decreasing the force required to extend the BSOC and improving elastic recovery is achievable by adding styrenic block copolymers into a Vistamaxx polymer. Micro-porous breathable elastic films based on calcium carbonate-filled elastomeric polypropylene-based compositions are also contemplated. The film may additionally increase the opacity of the BSOC and potentially eliminate or reduce the need for the presence of a meltblown layer in the nonwoven.

Exemplary BSOC materials related to these embodiments are disclosed in U.S. Pat. No. 6,909,028; U.S. Pat. No. 6,680,265; U.S. Pat. No. 6,680,265; U.S. Pat. No. 6,015,764; U.S. Pat. No. 5,947,944; WO 2004/060669; U.S. Pat. No. 6,627,564; U.S. Pat. No. 6,479,154; U.S. Pat. No. 6,465,073; U.S. Pat. No. 6,313,372; U.S. Pat. No. 6,001,460; WO 2004/060652; and U.S. Pat. No. 6,849,324.

In some embodiments of the present invention, an elastomer may be printed onto a nonwoven, film, or laminate, including those described above, to form a BSOC. The elastomer may be printed as a film or in a pattern. If printed as a pattern, the pattern may be relatively homogeneous over the area of the outer cover, i.e., in a net-like or dot pattern, or may comprise regions of relatively higher or lower basis weight wherein the elastomeric component is been applied onto at least one region of an extensible fibrous substrate to provide stretch properties to a targeted region of the substrate (i.e., after selective incremental stretching). The elastomer may be transferred onto the fibrous substrate through a process such as gravure printing which provides a great deal of flexibility relative to the amount of elastomer deposited as well as the type of patterns that can be achieved. Details on these embodiments, and further examples of suitable materials and patterns, are disclosed in US 2005/0214461, WO 2005/097358, and WO 2005/097512. Polyolefins blends and polyolefins/styrenic block copolymers such as those disclosed above and tailored to possess the desired rheological characteristics for adequate deposition via gravure printing represent preferred compositions for the present invention. Other exemplary materials and processes are disclosed in US 2005/0106980; U.S. Pat. No. 6,579,274; U.S. Pat. No. 6,503,236; and U.S. Pat. No. 6,264,641.

Regardless of the composition of the biaxially stretchable outer cover, the outer cover material can be mechanically activated in both the longitudinal and lateral directions via any of the processes described herein in order to increase the strain range over which the web exhibits stretch/recovery properties, impart the desirable tactile/aesthetic properties to the material (e.g., a cotton-like texture), and in some embodiments create the higher modulus components of the anchoring system, such as linkages or anchoring bands. Mechanical activation processes include ring-rolling, SELFing, and other means of incrementally stretching webs as known in the art. In some embodiments it may be desirable to (selectively) over-bond (parts of) the outer cover (at areas not activated) to further increase the mechanical strength of (parts of) the outer cover.

The outer covers of the present invention may additionally comprise graphics printed on the outside or inside surface of one of the outer cover or waist/leg band components or printed on an underlying component of the article. The graphics may be decorative, educational, entertaining, or instructional. Multiple topically related or unrelated graphics may be employed. The graphics may be formed such that they are most clear or legible when the printed substrate is in a relaxed condition or when the printed substrate is in an extended condition. Alternatively, some of the graphics may be most clear or legible when the printed substrate is in a relaxed condition, while others are most clear/legible when the printed substrate is in an extended condition. In certain embodiments, the graphics comprise active graphics, i.e., graphics which change based on environmental conditions such as elapsed time, humidity, temperature, wetness, etc. Active graphics may be topically related to each other so as to portray and event or action (e.g., a fish appears or disappears from a character's fishing line).

Core Assembly and Other Components

Referring back to FIG. 1B, in some embodiments, the core assembly 23 may include a topsheet 22, a containment member 28, and an absorbent core 26 disposed between the topsheet 22 and the containment member 28. As shown, the core assembly 23, in some embodiments, may form a bucket shape. The term "bucket-shaped" derives from the appearance of a lateral cross section of the core assembly 23 when the article is configured as it would be when applied to a wearer. The bucket-shaped core assembly 23 represents a substantially self-contained core assembly 23 as it may comprise the topsheet 22, absorbent core elements, a containment member 28, and leg cuffs 35, e.g. inner cuff or barrier leg cuffs. As will be appreciated from the description below, it can be said that the core assembly 23 is self-contained.

The core assemblies suitable for use in the absorbent articles of the present invention are not limited to the "bucket shaped" assemblies. For example, embodiments are contemplated where the core assembly comprises an absorbent core, optionally a core wrap, and optionally an acquisition/distribution system (see FIGS. 13A, 14A, 15A, 16, 17, 18, and 19A). One skilled in the art would appreciate that the core assemblies described herein can be utilized with any suitable anchoring system described herein. In the non-bucket embodiments the core is sandwiched between the topsheet and the outer cover. Preferably the core is (partially) force decoupled from the topsheet and the outer cover, i.e. the core can float.

As shown in FIG. 1B, in some embodiments, the containment member 28 covers a garment-facing surface of the core 26, at least in part, and extends laterally beyond the core 26. As shown, in some embodiments, the laterally distal ends of containment member 28 can be connected to a spacing member 30, such as an elastic, that biases a portion of the containment member 28 that is disposed laterally outboard of the core 26 vertically away from the body-facing surface of the chassis 21. In some embodiments, the spacing members 30 may bias the laterally distal ends vertically outwardly or vertically inwardly from longitudinal side edges of the core 26.

Some examples of suitable spacing members 30 include elastomeric films, elastomeric foams such as polyurethane foams or cross-linked natural rubber foams; formed elastic scrim; elastomeric films such as heat shrinkable elastic materials; elastomeric film laminates such as a laminate of a heat-shrinkable elastomeric film and a resilient member; and elastic strands made from rubber, synthetic rubber, elastomeric polyurethane, or other materials.

The laterally distal ends of the containment member 28 can define a pair of opposing and longitudinally extending leg cuffs 35 that extend out from the inner-facing surface 50 of the diaper 20 to provide a seal against the wearer's body and improve containment of liquids and other body exudates. Additionally, the containment member 28 may comprise a central zone 1500 and a pair of barrier zones 1510. The central zone 1500 is a portion of the containment member 28 disposed adjacent (but not necessarily in face-to-face contact) to the garment-facing surface of the absorbent core 26. In some embodiments, longitudinal boundary of the central zone 1500 is coterminous with the longitudinal edges of the absorbent core 26. However, in other embodiments, the longitudinal boundary of the central zone 1500 may be inboard or outboard of the longitudinal edges of the absorbent core 26. The barrier zones 1510 are portions of the containment member 28 disposed between the central zone 1500 and the distal ends of the containment member 28. The barrier zones 1510 serve as barrier leg cuffs 35 for the absorbent assembly 23. In other words, by extending away from the body-facing surface of the chassis 21, the barrier zones 1510 can provide a physical barrier to the free flow of exudates and provides a structure to contain the exudates within the absorbent assembly 23.

In some embodiments, the containment member 28 may additionally provide a forming layer on which liquid absorbent material can be deposited during manufacture of the core assembly 23 and is generally an air permeable material. The containment member 28 can be a hydrophobic material and can be rendered liquid impermeable, e.g., in the central zone 1500 and/or barrier zone 1510 of the containment member 28, by coating at least the garment-facing or the wearer-facing side, or both, of the central zone 1500 and/or the barrier zones 1510 of the containment member 28 with an impermeable material. The impermeable material may comprise a breathable or non-breathable film or may comprise an in-situ formed barrier layer such as a hydrophobic coating. The hydrophobic coating may comprise any suitable hydrophobic material known in the art. For example, the hydrophobic coating may comprise a wax composition, a hydrophobic skin care composition, or materials with similar properties, which is applied to the containment member 28 in a molten form and subsequently cooled to form a continuous coating. If at least the central zone 1500 of the containment member 28 is liquid impermeable, the outer cover 24 can be constructed as a liquid permeable member.

If the containment member 28 acts both as a forming substrate for at least a portion of the absorbent core 26 and as a leg cuff material, its properties can be properly balanced. For example, in some embodiments, the containment member 28 can be air permeable in a portion of the central zone 1500 and/or the barrier zones 1510 which may allow sufficient control over the process of absorbent material deposition thereon, Subsequent to the deposition of the absorbent material, the air permeability of the central zone 1500 may be decreased if desired. Additionally, the containment member 28 may be sufficiently impermeable to liquids in barrier zones 1510 to serve as a barrier cuff. Accordingly, in certain embodiments, the central zone 1500 may exhibit an air permeability of about 100 to 300 m$^3$/m$^2$/min at a pressure drop of 125 Pa, preferably around 120 to 200 m$^3$/m$^2$/min, as measured according to the Air Permeability Test provided below. Conversely, it is desirable that the barrier zone 1510 be liquid impermeable; however, it is believed that the degree of air permeability required in the central zone would harm liquid impermeability. Therefore, the barrier zone 1510 may exhibit an air permeability less than that of the central zone 1500. In certain embodiments, the barrier zone 1510 exhibits an air permeability that is about 10%, about 20%, about 50%, about 75%, or about 100% less than the air permeability of the central zone 1500.

The barrier zone 1510 may exhibit liquid impermeability for barrier protection while maintaining air and vapor permeability for wearer comfort. In certain embodiments, the barrier zone 1510 exhibits a hydrohead, as measured according to the Hydrostatic Head (Hydrohead) Pressure Test provided below, of greater than about 10 mbar, 20 mbar, and 40 mbar.

In some embodiments, the constraints on the properties of the base material of the containment member 28 may be relaxed by treating a portion of the containment member material to enhance its ability to perform either the core material deposition function (i.e., increase air permeability) or the barrier cuff liquid containment function (i.e., decrease liquid permeability). For example, the central zone 1500 may be treated such that its air permeability is increased, enabling it to better act as a core material deposition substrate. Alternatively, the barrier zones 1510 may be treated to make them more liquid impermeable to enhance their liquid barrier functionality as barrier cuffs.

Any suitable treatment known in the art can be utilized to increase air permeability and/or decrease liquid permeability. Examples of some suitable treatments include chemical, mechanical, thermal, and other surface energy modifying treatments, such as plasma treatment (e.g., via corona discharge, etc.). In one example, the treatment may reduce liquid permeability by decreasing the surface energy of the material, reducing the pore size distribution in the web, or occluding the web with a liquid impermeable layer. In another example, the treatment may increase air permeability by increasing the porosity of the web by mechanically inducing hole formation and/or enlargement via aperturing (e.g., pin aperturing, laser aperturing, etc.) or stretching the web (e.g., via tentering, or incremental stretching, e.g. activation, ring-rolling, SELFing). In some embodiments, both the central and barrier zones can be treated as described above. In another example the central cone 1500 initially has high air permeability, the absorbent material is deposited onto it (requiring the high air permeability), and afterwards the central zone 1500, and potentially zone 1510 are treated to make it less liquid permeable.

Some examples of suitable chemical treatments include application of hydrophobic compositions such as hydrophobic skin care compositions., silicones, or any other low surface energy composition as is known in the art. Some examples of suitable mechanical treatments include tentering, spreading (i.e., in the lateral direction via a spreading bar), incrementally stretching, e.g. ringrolling and SELFing, abrading, over-stretching (i.e., in the longitudinal direction), aperturing (i.e., via mechanical means such as pins or dies, lasers, water jets, air jets, and the like), puncturing, hole punching, slitting, microSELFing, and other mechanical treatments as known in the art. Some examples of suitable thermal treatments include heated smooth roll calendaring and other thermal means, such as hot air treatments, lasers, radiofrequency heating, and ultrasonics, to at least partially melt portions of the material structure (e.g., fibers) to reduce average pore size. In some embodiments, thermal treatments may be enhanced in embodiments wherein the barrier layer comprises a multi-component material, such as a nonwoven comprising bicomponent fibers wherein one of the components has a lower melting point than the other. Other suitable treatments for the central zone 1500, the barrier zones 1510 and suitable materials and configurations for the containment member 28 are discussed in a co-pending patent application 60/811,700 entitled "Absorbent Article Having a Multifunctional Containment Member", filed on behalf of Roe et al. on Jun. 7, 2006.

In some embodiments, the containment member 28 can be a single continuous material in its lateral dimension. In some embodiments, however, the containment member 28 can comprise two or more separate materials that overlap and/or abut along their lateral edges and are combined or bonded to form a composite web. For example, a web of a first material may form the central zone 1500 of the containment member 28, while a web of a second material may form each of the barrier zones 1510 of the containment member 28. Or, a web of a second material may form zone 1500 (e.g. a film), while a web of a first material (e.g. a nonwoven) may form zones 1500 and 1510. While the first and second materials may be identical or have similar properties, it may be preferable that they have properties specific to their intended functions. For example, per the above description, the first material may comprise a highly air permeable material while the second material may comprise a highly liquid impermeable material. The webs may be bonded via any know method as known in the art as long as the functionality of the central and barrier zones is minimally impacted. The webs may be bonded together along their entire lengths.

The containment member 28 may comprise a woven web, a nonwoven web, an apertured film, and a composite or laminate of any of the aforementioned materials. The containment member 28 may comprise a nonwoven, fibrous web that comprises synthetic and/or natural fibers. In certain embodiments, the containment member 28 is an air permeable nonwoven web such as described in U.S. Pat. No. 4,888,231.

As shown in FIG. 1B, in some embodiments, a core cover 29 can be disposed on a wearer-facing surface of the core 26 and may help immobilize the liquid absorbent material of the absorbent core 26. The core cover 29 may generally be a liquid pervious material, such as a nonwoven or tissue. In some embodiments, the core assembly 23 may further comprise the topsheet 22 which can be disposed adjacent a body-facing surface of the core cover 29.

The absorbent core 26 may comprise a wide variety of liquid-absorbent materials commonly used in disposable diapers and other absorbent articles. The absorbent core can comprise any absorbent material that is generally compressible, conformable, non-irritating to the wearer's skin, and capable of absorbing and retaining liquids such as urine and other certain body exudates. Examples of suitable absorbent materials include comminuted wood pulp (e.g., air felt creped cellulose wadding, fluff); melt blown polymers including co-form; chemically stiffened, modified or cross-linked cellulosic fibers; wraps and tissue, including wraps and tissue laminates; absorbent foams; absorbent sponges; superabsorbent polymers (such as superabsorbent fibers), absorbent gelling materials, mineral microfibers, and Parez™ bonded wet laid fibers, or any other known absorbent material or combinations of materials. Examples of some combinations of suitable absorbent materials are fluff with absorbent gelling materials and/or superabsorbent polymers, and absorbent gelling materials and superabsorbent fibers etc. The absorbent core can further comprise minor amounts (typically less than 20% or less than about 10%) of non-liquid absorbent materials, such as adhesives, waxes, oils, and combinations thereof.

Examples of other suitable absorbent core constructions are described in U.S. Publication No. 2004/0167486 to Busam et al. The absorbent core of the aforementioned publication uses no or minimal amounts of absorbent fibrous material within the core. Generally, the absorbent core may include no more than about 20% weight percent of absorbent fibrous material (i.e., [weight of fibrous material/total weight of the absorbent core]×100).

In certain embodiments the absorbent core may comprise an insert that may be removable from the article and replaceable with a fresh, unused insert. The insert may be applied to the wearer facing surface of the article and held in place via friction, overlapping portions of the article, or by a fastener element such as adhesive or a hook/loop fastening element. Alternatively, the insert may be inserted through an opening in the outer surface of the article or at the waist region such that the absorbent capacity of the article may be replenished without removing the article from the wearer. The article may also comprise addition absorbent core elements which may or may not be replaceable.

Regardless of its construction and composition, the absorbent core preferably contributes to an underwear-like appearance of the article. Since most underwear have no absorbent core, in certain embodiments, the cores of the present invention may be very thin. In these non-limiting embodiments the absorbent core may have a thickness when dry of no more than about 2 mm, preferably no more than about 1 mm, and generally within the range of 0.5 and 1.5 mm. It should be noted that the calliper of the core may vary across its area. At least a portion of the core should have the thinness described above; preferably at least about 25% of the total area of the core, more preferably at least about 50% of the total area of the core, and most preferably at least about 75% of the total area of the core.

Since underwear-likeness is a key aspect of discretion, and since discretion is relatively more important for older wearers (i.e., bedwetting school age children, adults, etc.), the cores of the present invention should have relatively high urine capacities. In embodiments of the present invention intended for wearers older than about 4 years of age (i.e., beyond typical toilet training age), the cores preferably have a capacity of at least about 500 grams of synthetic urine, more preferably more than about 700 grams of synthetic urine, and most preferably more than about 900 grams of synthetic urine.

In some embodiments, the absorbent core may comprise a fluid acquisition component which acquires fluid exudates and partitions the exudates away from a wearer's body, a fluid distribution component which distributes/redistributes fluid exudates points away from the point of initial exudate loading, and/or a fluid storage component which retains a majority of the fluid exudates on a weight basis. In some embodiments of the present invention the absorbent core may comprise, in addition to the storage layer and the durable hydrophilic core wrap, an acquisition system, which comprises an upper acquisition layer facing towards the wearer and a lower acquisition layer. In one embodiment the upper acquisition layer comprises a nonwoven fabric whereas the lower acquisition layer comprises a mixture of chemically stiffened, twisted and curled fibers, high surface area fibers and thermoplastic binding fibers. In other embodiments, both acquisition layers are provided from a non-woven material, which can be hydrophilic. The acquisition layer is in direct contact with the storage layer. Furthermore, the storage layer or parts thereof, such as the upper acquisition layer, can optionally be coated with a hydrophilicity boosting composition.

An example of a suitable absorbent core comprising an acquisition layer, a distribution layer, and/or a storage layer is described in U.S. Pat. No. 6,013,589. Other exemplary absorbent core configurations are discussed in U.S. Patent Application Publication No. 2003/0225382A1; U.S. application Ser. No. 11/329,797, entitled, "End Seal For an Absorbent Core", filed on Jan. 11, 2006; and U.S. application Ser. No. 11/329,796, entitled, "Sealed Core For An Absorbent Article", filed on Jan. 11, 2006. Yet other exemplary absorbent structures for use as the absorbent assemblies are described in U.S. Pat. No. 4,834,735, entitled "High Density Absorbent Members Having Lower Density and Lower Basis Weight Acquisition Zones", issued to Alemany et al. on May 30, 1989; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997.

The components of the core assembly 23 can be joined as described via any suitable adhesive or cohesive. While adhesive or cohesive can be used to connect various absorbent article components as illustrated and described herein, one having ordinary skill in the art will appreciate that any suitable alternative attachment mechanism can facilitate such connections. Examples of suitable alternatives include, but are not limited to, thermal bonds, RF (radio frequency) bonds, pressure bonds, ultrasonic bonds, welds, stitching, and the like. Any of the aforementioned layers of the core assembly 23 can comprise a single material or may comprise a laminate or other combination of two or more materials.

In conventional absorbent articles, cores are typically not stretchable. Because the outer cover can be biaxially stretchable, it may be beneficial to render the core stretchable, at least in the longitudinal direction. This will allow the product length to be reduced, while still being able to fit all the wearers in a given size. The core can be rendered stretchable in one of several ways. For example, the components that make up the core could be inherently stretchable, e.g. stretchable nonwovens. As another example, the core may comprise folds in the longitudinal direction, which unfold when the product is stretched. As another example, the core may comprise two separate parts, a front half and a back half, with some overlap in the crotch region, the first waist region, or the second waist region. As the diaper stretches, the two parts of the core slide past each other, decreasing the degree of overlap. It should be appreciated, however, that the core need not be stretchable for an absorbent article to suitably conform to the wearer's body in accordance with the principles of the present invention.

In certain embodiments, the chassis 21 provides the main structure of the diaper 20 with other features added to form the composite diaper structure. While the topsheet 22, the outer cover 24, and the core assembly 23 can be assembled in a variety of well-known configurations, certain diaper configurations are described generally in U.S. Pat. Nos. 3,860,003; 5,151,092; 5,221,274; 5,554,145; 5,569,234; 5,580,411; and 6,004,306. Topsheet 22, outer cover 24, and absorbent core 26 are discussed in more detail below.

Furthermore, while the topsheet 22, the outer cover 24, and the absorbent core 26 can include many different materials and can be assembled in a variety of well known configurations, suitable diaper materials and configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 issued to Buell on Sep. 9, 1992; and U.S. Pat. No. 5,221,274 issued to Buell on Jun. 22, 1993.

As described herein, the topsheet 22 is generally a portion of the diaper that can be positioned at least in partial contact or close proximity to a wearer. Accordingly, the topsheet can be supple, soft feeling, and non-irritating to a wearer's skin. Generally, at least a portion of the topsheet is liquid pervious, permitting liquids (e.g., urine) to readily penetrate through its thickness. The topsheet can be made of a hydrophobic material to isolate the wearer's skin from liquids contained in the absorbent core. Suitable topsheets can be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. A suitable topsheet is available from BBA Fiberweb, Brentwood, Tenn. as supplier code 055SLPV09U. Other examples of suitable topsheets 22 are described in U.S. Pat. No. 3,929,135, issued to Thompson on Dec. 30, 1975; U.S. Pat. No. 4,324,246 issued to Mullane et al. on Apr. 13, 1982; U.S. Pat. No. 4,342,314 issued to Radel et al on Aug. 3, 1982; U.S. Pat. No. 4,463,045 issued to Ahr et al. on Jul. 31, 1984; and U.S. Pat. No. 5,006,394 issued to Baird on Apr. 9, 1991. Other suitable examples of materials suitable for use as a topsheet are described in U.S. Pat. No. 5,916,661; U.S. Pat. No. 6,680,422B2; U.S. Pat. No. 5,342,338; and U.S. Patent Application Publication No. 2003/0021951A1.

In the various embodiments discussed above, the topsheet can span the entire range from being completely non-stretchable to being biaxially elastic. This covers extensibility in the lateral direction, longitudinal direction, or both the lateral and longitudinal directions, extensibility in one direction and elasticity in the other direction, and elasticity in one or both directions. In accordance with certain aspects of the invention, particularly considering manufacturing costs, it may be desired to confine all the elastic stretch (recoverable stretch) to just the outer cover.

Alternatively, the topsheet can be rendered stretchable (extensible or elastic) by any of the methods known in the art, including incremental stretching, stretch bonding, neck bonding, and the like. A non-stretchable topsheet can be made extensible in the lateral direction during fabrication by incrementally stretching in the lateral direction, maintaining enough longitudinal tension in the web in order to prevent the web from spreading out, and bonding the topsheet to the outer cover and core of the diaper while the width of the web is maintained. Extensibility or slack can be built into a non-elastic topsheet in the longitudinal direction by pre-stretching a shorter, elastic outer cover in the longitudinal direction to make it the same length as the longer topsheet, bonding the two together at least in some areas, and allowing the outer cover to retract. This produces regions in the topsheet that are gathered in the longitudinal direction, thus allowing the diaper to stretch up to the full length of the topsheet without the topsheet offering any significant resistance.

The topsheet can be rendered elastic using any of the methods known in the art, including stretch bonding, neck bonding incremental stretching, and the like. The preferred options for making an elastic topsheet are similar to those used to make the elastic outer cover.

The topsheet can be made stretchable in one direction or biaxially stretchable by any of the methods known in the art. In accordance with certain aspects of the present invention, the topsheet can be rendered biaxially elastic. For example, the topsheet could be an elastomeric nonwoven formed from a mixture of elastomeric and non-elastomeric fibers/filaments. Incrementally stretching the nonwoven releases the stretch properties. An alternative approach would be printing an elastomeric composition onto an extensible substrate, followed by incremental stretching if desired. Yet another approach is to print an elastomeric composition onto an elastomeric nonwoven or film.

Any portion of the topsheet can be coated with a lotion as is known in the art. Examples of suitable lotions include those described in U.S. Pat. Nos. 5,607,760; 5,609,587; 5,635,191; and 5,643,588. The topsheet can be fully or partially elasticized or can be foreshortened so as to provide a void space between the topsheet and the core. Exemplary structures including elasticized or foreshortened topsheets are described in more detail in U.S. Pat. Nos. 4,892,536; 4,990,147; 5,037,416; and 5,269,775.

For example, the diaper may also include a waistband 43 (see FIG. 1A) that can generally form at least a portion of the end edge 56 of the diaper 20. The waistband 43 is that portion or zone of the diaper 20 which is intended to elastically expand and contract to dynamically fit the wearer's waist, and that helps provide improved fit and containment. The elastic waistband 43 can include a segment positioned in the front waist region 36 and/or back waist region 38, and can be discretely attached or an integral part of the chassis 21. Examples of suitable waistbands include those described in U.S. Pat. No. 4,515,595; U.S. Pat. No. 5,151,092; and U.S. Pat. No. 5,221,274.

The diaper can also include a leg band or leg elastic that helps provide improved fit and containment, as is appreciated by one having ordinary skill in the art. The leg band is that portion or zone of the diaper 20, which is intended to elastically expand and contract to dynamically fit the wearer's leg. Leg elastics may include several different embodiments for reducing the leakage of body exudates in the leg regions. Leg elastics and contractible leg openings are discussed in U.S. Pat. No. 3,860,003; U.S. Pat. No. 4,909,803; U.S. Pat. No. 4,695,278; and U.S. Pat. No. 4,795,454.

Alternatively, the waist and/or leg bands may comprise a separate element discretely affixed to the inner or outer surface of the article in proximity to the lateral or longitudinal edges of the article. The separate element is preferably elastomeric and more preferably pre-tensioned prior to attachment to the article so as to provide a contracted waist and/or leg feature. The waist and/or leg band elements may comprise a zero-strain laminate or a pre-stretched laminate, a film, a foam, or an elastic nonwoven. If a laminate, the separate element preferably additionally comprises at least one elastomeric element such as an elastomeric film, a printed elastomeric pattern, elastic strands, or an elastic nonwoven or foam. The distal edge of the waist and/or leg band may be aligned with the distal edge of the article, may extend beyond the edge of the article, or may terminate inboard of the article edge. In certain embodiments, the waist and/or leg band may at least partially wrap around the edge of the article and may be bonded to both the inner and outer surfaces of the article, or a component thereof.

Additionally, in some embodiments, the diaper 20 may comprise finished outer leg cuffs. Finished outer leg cuffs and waist edges are discussed in U.S. Pat. No. 5,797,824 and U.S. Pat. No. 7,013,941, while the latter also discusses methods and an apparatus for applying the material.

In certain alternative embodiments, the waist edge may be nonparallel to the lateral centerline of the article. Nonlinear waist edges may be convex or concave relative to the lateral centerline, or may have portions which are concave and other portions which are convex relative to the lateral centerline. The waist edge is preferably symmetric relative to the longitudinal centerline, but embodiments are contemplated having a waist edge asymmetric relative to the longitudinal axis.

Additionally, in some embodiments, in order to provide more comfort and fit to the wearer, the leg elastics may be joined to the chassis 21 of the diaper 20 such that the leg elastics are curved. In some embodiments, the elastics can be applied in a direction which is generally parallel to the longitudinal centerline. In some embodiments, the leg elastics can be applied in a curvilinear configuration. The leg elastics may be joined to the chassis 21 in any suitable manner known in the art whether the leg elastics are curved or otherwise.

Figure 9:
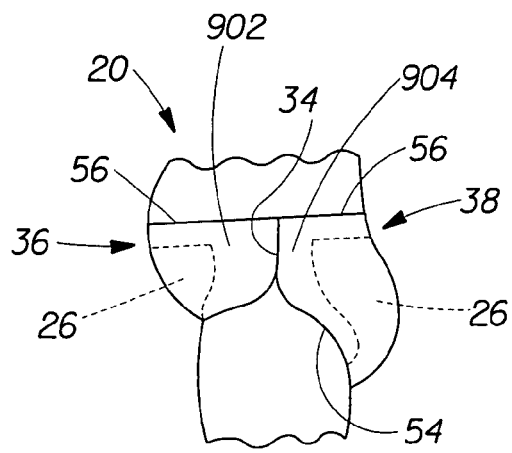
FIG. 9 illustrates a side view of an embodiment of an absorbent article as worn on a wearer, according to the present disclosure.

Referring now to FIG. 9, when the diaper 20 is configured as a pull on diaper, the diaper 20 is worn on the lower torso of a wearer. As shown, when a first side panel 902 is joined to a second side panel 904, the end edges 56 encircle the waist of the wearer while, at the same time, the chassis side edges 54 define leg openings that receive the legs of the wearer. The crotch region 37 (shown in FIG. 1A) is generally positioned between the legs of the wearer, such that the absorbent core 26 extends from the front waist region 36 through the crotch region 37 to the back waist region 38.

In some embodiments, the first and/or second side panel 902 and 904, can be formed of discrete separate elements affixed to the diaper 20. In some embodiments, the first and/or second side panel 902, 904, can be formed from a unitary piece of material that is neither divided nor discontinuous with an element of the diaper 20. For example, in some embodiments, the side panels may comprise a portion of a topsheet. As another example, the side panels may comprise a portion of a backsheet. As yet another example, the side panels may comprise a portion of a barrier leg cuff (discussed hereafter).

The side panels 902 and 904 can be extensible or can be elastically extensible. While extensible side panels may be constructed in a number of configurations, examples of diapers with extensible side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; in U.S. Pat. No. 5,151,092 issued to Buell et al. on Sep. 29, 1992; U.S. Pat. No. 6,677,258 issued to Carroll et al. on Jan. 13, 2004; U.S. patent application Ser. No. 10/396,977 filed on Mar. 25, 2003, U.S. Pat. No. 5,580,411 entitled "Zero Scrap Method For Manufacturing Side Panels For Absorbent Articles" issued to Nease, et al. on Dec. 3, 1996; and U.S. Pat. No. 6,004,306 entitled "Absorbent Article With Multi-Directional Extensible Side Panels" issued to Robles et al. on Dec. 21, 1999.

The diaper 20 can be preformed by the manufacturer to create a pull-on diaper or pant. Specifically, the diaper 20 may include left and right closed side seams 34, each disposed at regions proximal the front and back ends of side edges 54. Each side seam 34 can be closed by buttressing and subsequently attaching a given side edge 54 in the front and back waist regions 36 and 38 either using a permanent seam or refastenable closure member. It should be appreciated that side edges can alternatively be attached in an exterior surface-to-exterior surface configuration, interior surface-to-interior surface configuration, or interior surface-to-exterior surface (overlapping) configuration.

Figure 10:
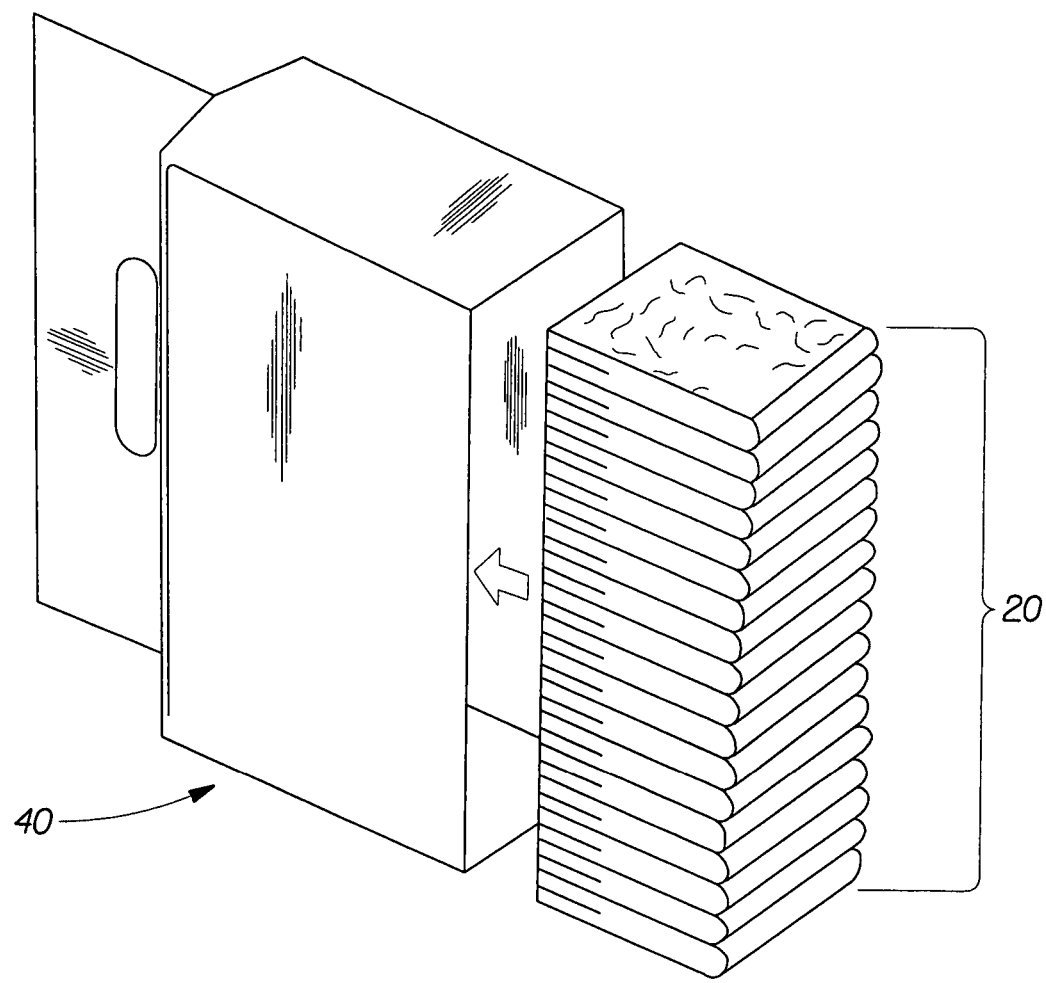
FIG. 10 illustrates a perspective view of an embodiment of package of absorbent articles, according to the present disclosure.

Because the diaper 20 is configured as a pull-on diaper, both side seams 34 can be closed prior to the application of the article to a wearer. In some embodiments, the diaper 20 can be configured such that the diaper 20 is prefastened by the manufacturer, i.e. the caregiver or wearer does not have to fasten the diaper 20 upon removal of the diaper from a package 40 (shown in FIG. 10). In some embodiments, the diaper 20 can be unfastened in the package 40, i.e. the caregiver or wearer fastens the diaper 20 prior to donning the diaper 20 on the wearer such that the diaper 20 is configured as a pull-on.

The side seams 34 can be closed in accordance with any known techniques or methods known in the art. For instance, the seams 34 can be formed with a permanent seam, which can include a bond formed by heat sealing such as ultrasonic bonding, high pressure bonding, RF (radio frequency) bonding, hot air bonding, heated point bonding, and the like as appreciated by one having ordinary skill in the art.

As another example, the side seams 34 may comprise fastening elements which are refastenable. The fastening elements may comprise any refastenable fastening elements known in the art. For example, the fastening elements may comprise hook and loop fasteners, hook and hook fasteners, macrofasteners, tape fasteners, adhesive fasteners, cohesive fasteners, magnetic fasteners, hermaphrodidic fasteners, buttons, snaps, tab and slot fasteners, and the like. Some suitable examples of fastening systems and/or fastening elements are discussed in U.S. Pat. Nos. 3,848,594; 4,662,875; 4,846,815; 4,894,060; 4,946,527; 5,151,092; 5,221,274; 6,432,098; U.S. patent application Ser. No. 11/240,943, entitled, "Anti-Pop Open Macrofasteners" filed on Sep. 30, 2005; U.S. patent application Ser. No. 11/240,838, entitled, "A Fastening System Having Multiple Engagement Orientations", filed on Sep. 30, 2005. Additionally, various suitable pant configurations are disclosed in U.S. Pat. No. 5,246,433; U.S. Pat. No. 5,569,234; U.S. Pat. No. 6,120,487; U.S. Pat. No. 6,120,489; U.S. Pat. No. 4,940,464; U.S. Pat. No. 5,092,861; U.S. Pat. No. 5,897,545; U.S. Pat. No. 5,957,908; and U.S. Patent Publication No. 2003/0233082 A1 (published on Dec. 18, 2003 to Mark J. Kline, et al.).

In other embodiments, secondary fasteners may be employed to enable adjustment of the article once the article has been applied to a wearer. Secondary fasteners serve to increase the tension (i.e., "cinch") in the waist hoop subsequent to application in order to provide enhanced sustained fit of the article. Secondary fasteners may include any type of fastener as known in the art and may be associated with a stretch element that aids in increasing the tension in the waist hoop.

Alternatively, the closed side seams 34 can be formed as disclosed in U.S. Pat. No. 5,779,831; U.S. Pat. No. 5,772,825; U.S. Pat. No. 5,607,537; U.S. Pat. No. 5,622,589; U.S. Pat. No. 5,662,638; U.S. Pat. No. 6,042,673; and U.S. Pat. No. 6,726,792. The aforementioned patents disclose various processing methods to provide absorbent pull-on diapers. One of the processes utilizes a final knife followed by a reciprocating tucker blade that pushes the pad from a horizontal orientation to a vertical orientation and a vacuum conveyor belt that holds the pad through a high pressure side seaming unit. The side seaming unit is followed by a slitter that trims the pant edges to provide a finished seam edge. An alternative method disclosed in the aforementioned patents involves cutting the pad in the final knife and bi-folding the pad collecting the pads in a "waterwheel" stacker (a rotary slotted wheel). The bonding is accomplished while the pad is held in place on the rotating wheel.

The present invention therefore recognizes that a plurality of pull-on diapers 20 can be pre-formed with closed side seams 34 and subsequently packaged and delivered to a user to prevent the need for the user (which could be the wearer) to close the side edges 54 prior to securing the diaper 20 on the wearer. Accordingly, referring to FIG. 10, the present invention includes the method of providing a plurality of pull-on diapers 20 of the type described above, and placing the diapers 20 into a closed package 40 that retains the diapers 20. Accordingly, when the end user opens the packaging 40, the pull-on diaper 20 can be donned on the wearer more easily than conventional taped diapers. Embodiments comprising taped diapers are discussed hereafter.

Other Embodiments

One having ordinary skill in the art will appreciate that the anchoring system 42 of the present invention can assume many alternative configurations that decouple forces from the core and the outer cover and direct the decoupled forces to the wearer's hip region. It will thus be apparent that any of the features of anchoring system elements (e.g., the circumferential anchoring member, anchoring members, and the LDEs) can be combined in any desired manner in accordance with the principles of the present invention. Some additional embodiments of anchoring systems have been provided heretofore. Still other exemplary embodiments follow.

Additionally, one of ordinary skill in the art will appreciate that the anchoring system can be adapted to a number of different core assembly configurations and diaper configurations. For example, diapers constructed in accordance with the present invention may comprise additional elements from those discussed heretofore. Some exemplary core assembly and diaper assembly configurations are provided hereafter.

Figure 11:
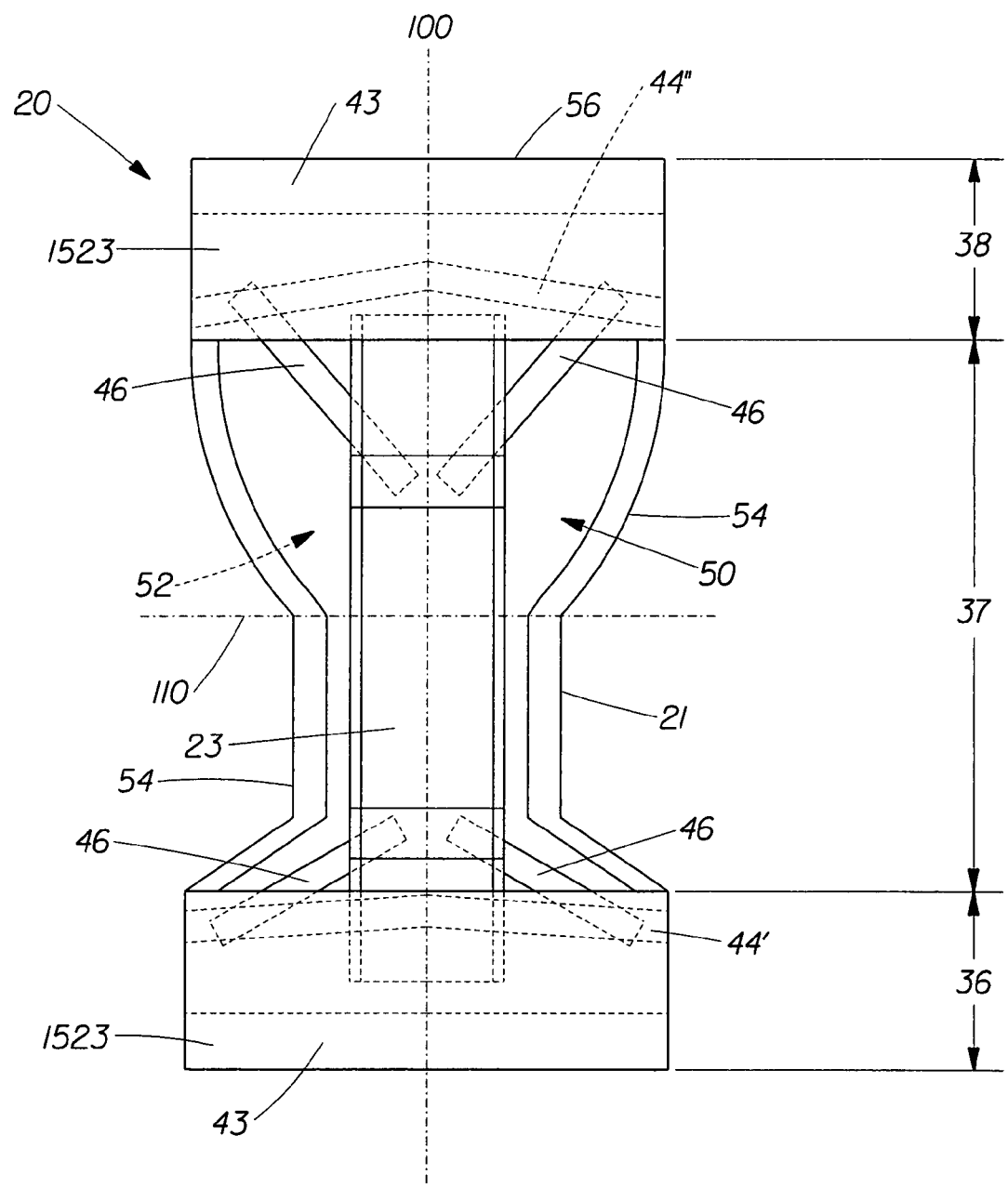
FIG. 11 illustrates a plan view of an embodiment of disposable absorbent article with an absorbent core, an anchoring system, and a waist cover, according to the present disclosure.
Figure 12A:
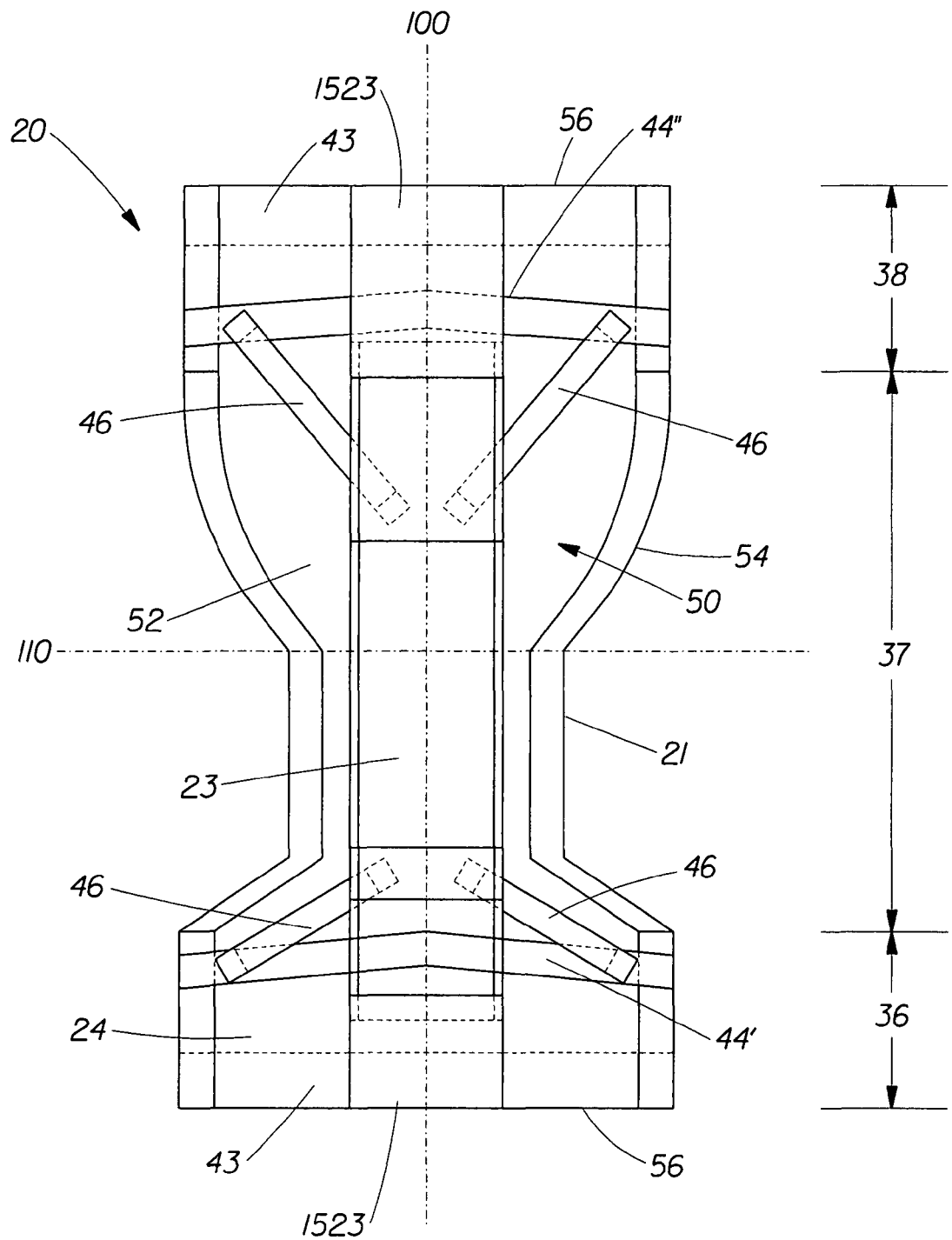
FIG. 12A illustrates a plan view of an embodiment of disposable absorbent article with an absorbent core, an anchoring system, and a waist cover, according to the present disclosure.

With regard to FIGS. 11 and 12A, in some embodiments, the diaper 20 may further comprise a stretchable waist cover 1523 which may be attached to the diaper 20 in the first waist region 36 and/or the second waist region 38. The waist cover makes it possible to effectively manage the edges of the discrete core bucket when the core bucket is not attached to the outer cover along its full length, but only in a narrow region in the center. Without the waist cover, the edges of the core bucket would need to be bonded to the outer cover, thus compromising outer cover stretch. As shown in FIG. 11, in some embodiments, the waist cover 1523 can be full width, e.g. extending from the first side edge 54 to the second side edge 54 in the first waist region 36 and/or the second region 38. A full width waist cover 1523 may be joined to a portion of the core assembly 23 proximate to an end of the core assembly 23, may be joined to the chassis 21 adjacent to the side edges 54, and/or may be joined to the waistband 43.

As shown in FIG. 12A, in some embodiments, the waist cover 1523 may extend laterally about the same width as the core assembly 23. The waist cover 1523, as shown in FIG. 12A, in some embodiments, may be joined proximate to an end of the core assembly 23 and/or the waistband 43. In one specific embodiment, the diaper 20 may comprise the waist cover 1523 which has a width which is generally about equal to the width of the core assembly 23. In an alternate embodiment, the waist cover is formed by a discrete waistband attached to the inner surface of the article and extending longitudinally inboard a sufficient distance to cover the longitudinal ends of the core. In this embodiment, the waistband may be bonded to the outer cover proximate the waist edge and along its longitudinal edges, but not to the core assembly. In a further alternate embodiment wherein the core assembly comprises a "bucket" construction and wherein the bucket core assembly has a longitudinal dimension smaller than the longitudinal dimension of the article, the waist cover may comprise an extension of the topsheet portion of the bucket core assembly affixed to the outer cover proximate the waist edge of the article. In this embodiment, lateral extensibility in the waist cover region is provided via use of an extensible topsheet and/or mechanical activation (incremental stretching) of the portion of the topsheet extending beyond the bucket core assembly.

The waist cover 1523 may have several functions. For example, the waist cover 1523 may prevent the ends of the core assembly 23 disposed nearest to the first waist region 36 and the second waist region 38, which may not be bonded to the outer cover 24, from flipping over or buckling during product application/wearing. It should be noted that by not locking the stretchable outer cover 24 down with the longitudinal ends of the core assembly 23, the diaper 20 may be capable of more stretch in the longitudinal direction, and thus capable of providing a better conforming fit. As another example, the waist cover 1523 may improve aesthetics by hiding any non-bonded ends of the core assembly 23. As yet another example, the anchoring bands 44', 44", and/or LDEs 46 can be attached to the waist cover 1523 instead of the outer cover 24, thus significantly improving outer cover 24 aesthetics and product conformity, especially in the longitudinal direction. In some embodiments, the anchoring bands 44', 44", and/or the LDEs 46, or a portion thereof, can be integral with the waist cover 1523. For example, portions of the waist cover 1523 which are not the anchoring bands 44', 44", and/or the LDEs 46 may be incrementally stretched more so than the anchoring bands 44', 44", and/or the LDEs 46. The waist cover 1523 can be treated as described above with regard to the integral formation of the anchoring system in the outer cover.

In some embodiments, the waist cover 1523 can be stretchable in at least one direction (lateral or longitudinal), preferably in both. Also, in some embodiments, the waist cover 1523 may be elastic. The waist covers 1523 may utilize any suitable material known in the art. Some suitable examples of material suitable for use as the waist cover 1523 include some of the examples provided for the outer cover 24. Additionally, the waist covers 1523 may have the same properties as the outer cover 24 described heretofore, e.g. force at 15% strain and % set (per the Hysteresis Test provided hereafter). Additionally, the waist cover material 307 is preferably a skin friendly, soft, and liquid permeable, stretchable in machine direction material. Suitable materials are activatable nonwoven and apertured nonwoven material as described in U.S. Pat. Nos. 5,342,338 6,680,422B2.

The anchoring bands 44' and/or 44" can be partly or fully attached to either the waist cover 1523 or the outer cover 24 or both, in some embodiments. For example, anchoring band 44' may be attached to the outer cover 24, while anchoring band 44" may be attached to the waist cover 1523, or vice versa. One skilled in the art will appreciate that the anchoring bands 44' and 44" can be positioned at the desired location on the wearer's body to carry the desired level of force/modulus regardless of whether the anchoring bands are partially or fully attached to the waist cover 1523, the outer cover 24, or both.

Figure 12B:
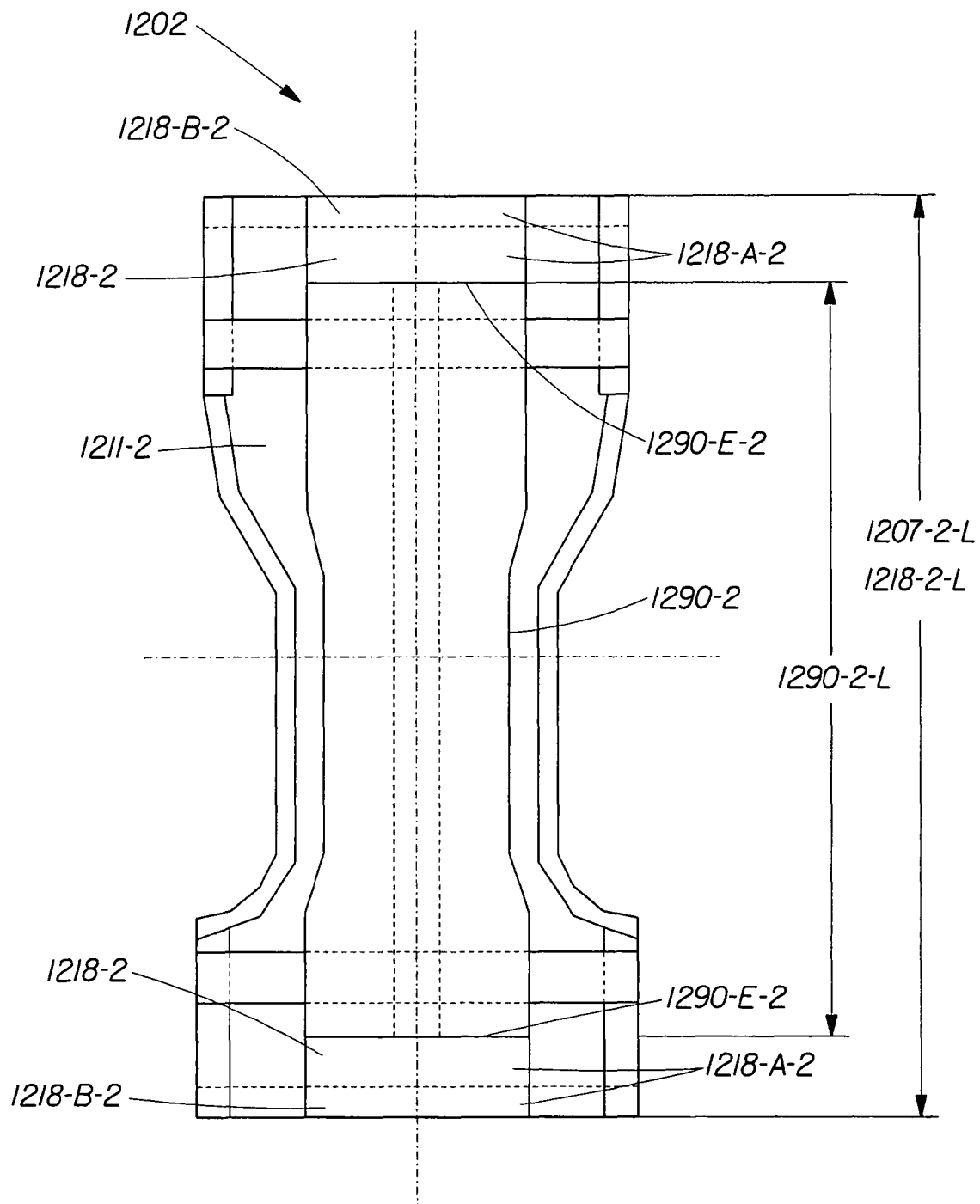
FIG. 12B illustrates a plan view of an embodiment of disposable absorbent article with a carrier web for core end management, according to the present disclosure.

In order to manage the edges of the core bucket, in some embodiments, a carrier web may be attached to the core bucket, the carrier web being the full length of the product. The carrier web is extensible in either the lateral or longitudinal direction, or both. The carrier web may also be elastic. The carrier web may be a nonwoven or a film. In some embodiments, the carrier web is incrementally stretched at least at one of the two longitudinal ends in and near the waist band area, or even over substantially all of the carrier web. This incremental stretching may be done prior to or after bonding the carrier web to the outer cover in the waist band area. This carrier web may be attached to the garment facing side of the core bucket or anywhere inside the core bucket. This carrier web is longer than the core bucket and either the same as or less than the length of the outer cover. In the embodiment of FIG. 12B, an absorbent article 1202 has a chassis 1211-2, an outer cover, a carrier web 1218-2, and an absorbent core 1290-2 with ends 1290-E-2. The outer cover has an outer cover length 1207-2-L, which is about the same as a carrier web length 1218-2-L of the carrier web 1218-2. The carrier web 1218-2 includes activated regions 1218-A-2. The carrier web 1218-2 is attached to the outer cover at locations 1218-B-2.

Figure 12C:
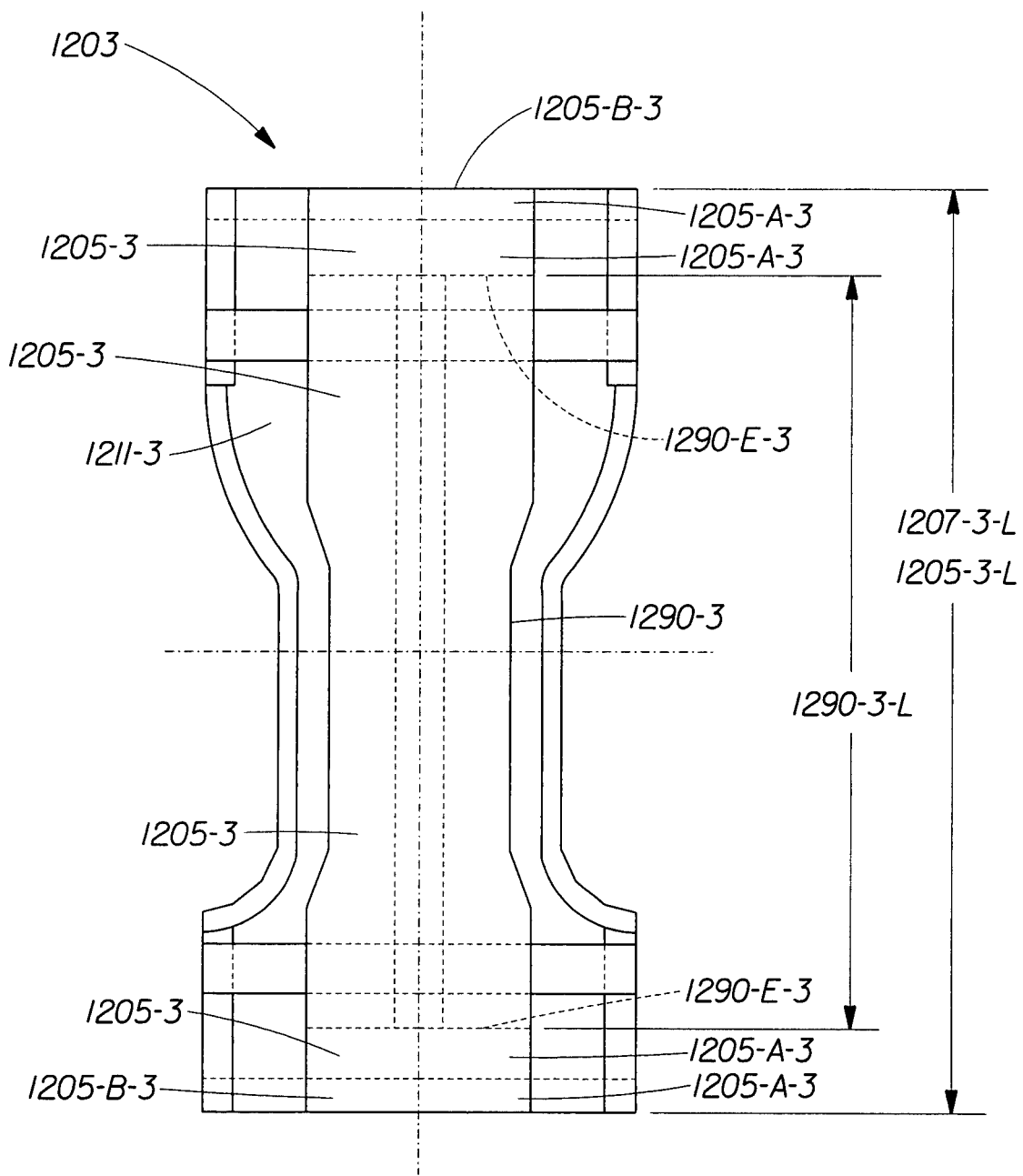
FIG. 12C illustrates a plan view of an embodiment of disposable absorbent article with an activated topsheet for core end management, according to the present disclosure.

In some embodiments, one of the components of the core bucket may serve the function of the carrier web. For example, either the topsheet (or body side liner), or the breathable polyethylene film, or the barrier leg cuff or combinations thereof may be made longer than the core bucket and incrementally stretched at the longitudinal ends. These components of the core bucket that are about the length of the product are then attached to the outer cover in the waist band area. In the embodiment of FIG. 12C, an absorbent article 1203 has a chassis 1211-3, an outer cover, a full-length topsheet 1205-3, and an absorbent core 1290-3 with ends 1290-E-3. The outer cover has an outer cover length 1207-3-L, which is about the same as a topsheet length 1205-3-L of the full-length topsheet 1205-3. The full-length topsheet 1205-3 includes activated ends 1205-A-3 past the ends 1290-E-3 of the absorbent core 1290-3. The carrier web 1218-2 is attached to the outer cover at location 1218-B-3.

Figure 13B:
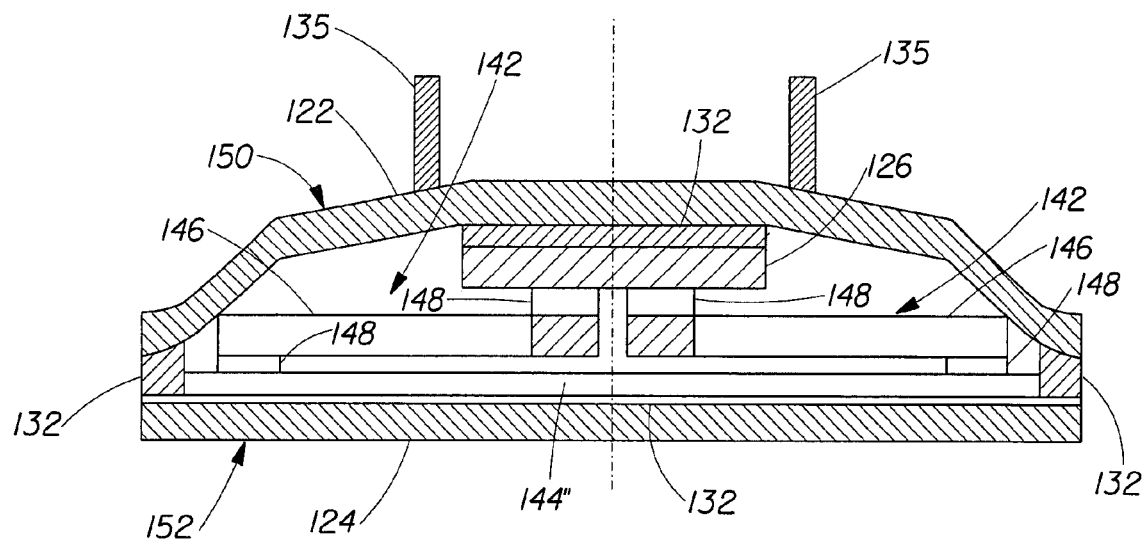
FIG. 13B illustrates a cross-sectional view of the disposable absorbent article of FIG. 13A, according to the present disclosure.
Figure 13C:
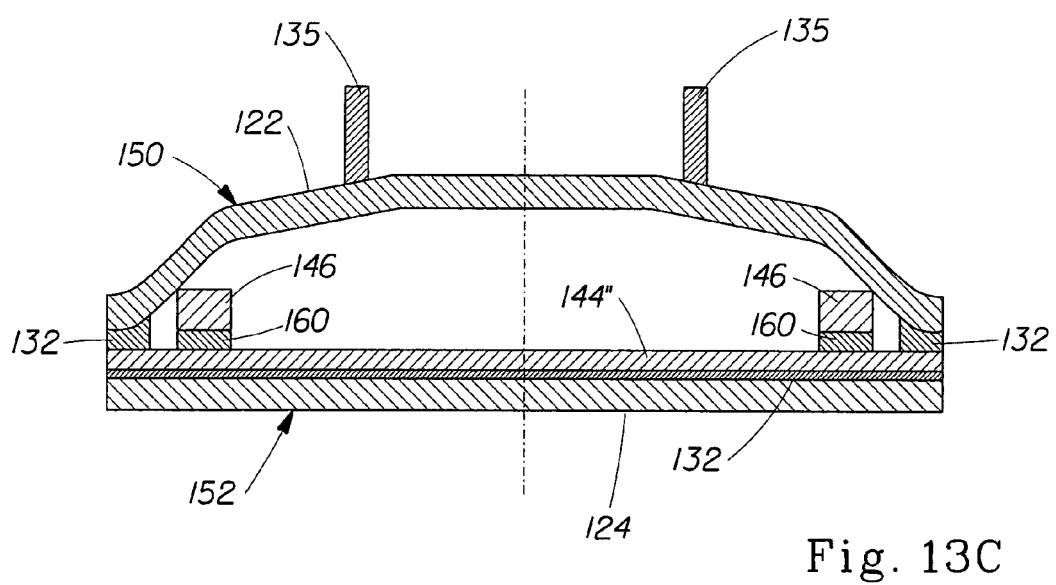
FIG. 13C illustrates a cross-sectional view of the disposable absorbent article of FIG. 13A, according to the present disclosure.

With regard to FIGS. 13A-13C, an absorbent article 120 is illustrated in accordance with an alternative embodiment, wherein reference numerals of elements illustrated in FIGS. 13A-13C correspond to like elements of FIGS. 1A-1C and are incremented by 100 for the purposes of clarity and convenience.

The absorbent article 120 may be constructed similar to the absorbent article 20. However, in some embodiments, the chassis 121 may include a liquid pervious topsheet 122, and a liquid impervious outer cover 124 joined to the topsheet 122 proximal the lateral end edges 156 and the longitudinal side edges 154 via any suitable adhesive or cohesive 132. As described above, the outer cover 124 can advantageously be stretchable in one or more directions, preferably biaxially stretchable, and more preferably biaxially elastic, thereby enhancing both the comfort of the diaper 120 on the wearer and the conformability to the wearer's anatomy during movement.

A core assembly 123 may include an absorbent core 126 that is positioned between the topsheet 122 and the outer cover 124. In some embodiments, the outer cover 124 and the topsheet 122 are stretchable, either axially or biaxially; and the core 126 can be said to "float" between the topsheet 122 and the outer cover 124. In some floating core embodiments, the core, or any components of the core, may not be bonded to the topsheet and/or outer cover. In other floating core embodiments, the core is bonded to the topsheet and/or outer cover over a limited portion of its surface area so as to maximize the "underwear-like" nature of the outer cover (i.e., the outer cover is substantially decoupled from the core or loads generated by the core or contents thereof). For example, a floating core may be bonded to the topsheet and/or outer cover over less than 50% of its surface area, and preferably less than 25% of its surface area. The floating cores of the present invention may be bonded to the topsheet and/or outer cover over an area between about 2 percent and about 20 percent of the core surface area. The absorbent core 126 can be disposed symmetrically or asymmetrically with respect to either or both of the longitudinal centerline 200 and the lateral centerline 210. For example, as shown in FIG. 13A, the absorbent core 126 is symmetrical with respect to both the longitudinal centerline 200 and the lateral centerline 210.

As shown in FIG. 13B, the topsheet 122 can be disposed adjacent the body-facing surface of the absorbent core 126, while the outer cover 124 can be disposed adjacent the garment-facing surface of the absorbent core 126. The topsheet 122 can be (partially) attached to the core 126 via the adhesive or cohesive 132 or any suitable means known in the art. In another embodiment the topsheet 122 and outer cover 124 are not directly attached to the core. Rather the core is only connected to the outer cover and the topsheet via the LDE(s) and the CAM(s). In this execution it may be desirable to reduce the coefficient of friction of the core against the topsheet and/or the coefficient of friction of the core against the outer cover. In one embodiment, the outer cover 124 is substantially impervious to liquids. It should be appreciated that the topsheet 122 can be attached to the core 126 and/or the outer cover 124 and that the outer cover 124 can be attached to the core 126 and/or the topsheet 122.

It should be further recognized that other structures, elements, or substrates can be positioned between the core 126 and the topsheet 122 and/or outer cover 124. For instance, the core 126 can be disposed between the topsheet 122 and a breathable liquid impermeable film formed from polyethylene or the like. In such an embodiment, the outer cover 124 could be pervious to liquids, as described above with reference to FIG. 1A.

As shown in FIG. 13A, in some embodiments, the topsheet 122 and the outer cover 124 have length and width dimensions generally larger than those of the absorbent core 126. The topsheet 122 and the outer cover 124 can extend beyond the lateral and longitudinal edges of the absorbent core 126 to form the periphery of the diaper 120. While the topsheet 122, the outer cover 124, and the absorbent core 126, can include many different materials and can be assembled in a variety of well known configurations, suitable diaper materials and configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 issued to Buell on Sep. 9, 1992; and U.S. Pat. No. 5,221,274 issued to Buell on Jun. 22, 1993.

The topsheet 122 can be configured in a similar manner to the outer cover 124. Additionally, in some embodiments, the anchoring system 142 of the present invention may be integral with the topsheet 122. For example, portions of the topsheet 122 which do not comprise a portion of the anchoring system 142 can be mechanically activated to a greater extent than portions of the topsheet 122 comprising the anchoring system 142. The topsheet 122 can be treated as described above with regard to the integral formation of the anchoring system in the outer cover.

The diaper 120 can further include a pair of opposing and longitudinally extending barrier leg cuffs 135 that extend out from the inner body-facing surface 150 of the chassis 121 to provide a seal against the wearer's body and improve containment of liquids and other body exudates. Each barrier leg cuff 135 can include several different embodiments for reducing the leakage of body exudates in the leg regions. Some suitable examples of barrier leg cuffs are discussed in U.S. Pat. No. 3,860,003; U.S. Pat. No. 4,909,803; and U.S. Pat. No. 4,695,278.

In some embodiments, the barrier leg cuffs 135 can be generally parallel to the longitudinal centerline 200 of the diaper 120. However, embodiments are contemplated where the barrier leg cuffs 135 are curved outward. For example, the spacing between the barrier leg cuffs 135 may be less in the crotch region 137 and more in the waist regions 136 and 138.

The diaper 120 may further comprise a waistband 143 that helps provide improved fit and containment, as is appreciated by one having ordinary skill in the art. The waistband 143 may be configured similar to the waistband 43 described heretofore. In contrast, embodiments are contemplated where the anchoring bands 144' and/or 144" generally form at least a portion of the end edge 156 of the diaper 120.

Disposable diapers are often constructed so as to have at least one elastic waistband 143 positioned in the front waist region 136 and/or back waist region 136. Furthermore, while in some embodiments the elastic waistband 143 or any of its constituent elements can include a separate element affixed to the diaper 120, the waistband 143 need not be separately affixed to the diaper 120. For instance, the elastic waistband 143 can be constructed as an extension of other elements of the diaper 120 such as the outer cover 124, the topsheet 122 or both the outer cover 124 and the topsheet 122. Examples of suitable waistbands include those described in U.S. Pat. No. 4,515,595; U.S. Pat. No. 5,151,092; and U.S. Pat. No. 5,221,274.

The diaper 120 also includes a leg band or leg elastic that helps provide improved fit and containment, as is appreciated by one having ordinary skill in the art. The leg band is that portion or zone of the diaper 120, which is intended to elastically expand and contract to dynamically fit the wearer's leg. Leg elastics may include several different embodiments for reducing the leakage of body exudates in the leg regions. Leg elastics and contractible leg openings are discussed in U.S. Pat. No. 3,860,003; U.S. Pat. No. 4,909,803; U.S. Pat. No. 4,695,278; and U.S. Pat. No. 4,795,454.

Additionally, in some embodiments, in order to provide more comfort and fit to the wearer, the leg elastics may be joined to the chassis 121 of the diaper 120 such that the leg elastics are curved. In some embodiments, the elastics can be applied in a direction which is generally parallel to the longitudinal centerline. In some embodiments, the leg elastics can be applied in a curvilinear configuration. The elastics may be applied to the chassis 121 by any suitable means known in the art.

The diaper 120 further includes an anchoring system 142 (shown in FIG. 13A) of the type described above with reference to FIGS. 1A-1C that is intended to fit to the pelvic region of the torso and that supports the core 126 and central chassis 121, and directs the load forces to at least a portion of the wearer's waist region where the forces can be coupled into the wearer's body. During wear, the waist and leg perimeters, 156 and 154, respectively, move with the parts of the body (spine and legs, respectively) that can move relative to the pelvis. Thus these perimeters can move relative to the anchoring system 142, which, in turn, changes the distances between the perimeters and the anchoring system 142. The waist and leg perimeters can be mechanically isolated from the anchoring system 142 by a bi-axially stretchable outer cover 124, "BSOC", and or a biaxially stretchable topsheet, both designed to minimize forces that arise between the waist or leg perimeters and the anchoring system from movement of the legs and spine relative to the pelvis.

As shown in FIGS. 13A-13C, the diaper 120 may further comprise a pair of anchoring bands 144' and 144" which can form a circumferential anchoring member as described heretofore with regard to the CAM 44A (shown in FIG. 2A). In some embodiments, the anchoring bands 144' and/or 144" can be attached to the wearer-facing surface of the outer cover 124 via any suitable adhesive or cohesive. When the diaper 120 is preformed in to a pant, the anchoring bands 144' and 144" are operatively connected via the side seam or closure member to form the continuous circumferential anchoring member that circumscribes the wearer's lower torso region.

As shown in FIG. 13A, the diaper 120 may further comprise a plurality of LDEs 146. For example, as shown, two LDEs 146 may be disposed in the first waist region 136 extending outward from the core 126 toward their respective side edges 154. Similarly, two LDEs 146 may be disposed in the second waist region 138 extending outward from the core 126 toward their respective side edges 154. Additionally, the LDEs 146 can extend laterally outward from the core 126 and toward the corresponding end edge 156 and terminate at opposing ends that can be joined to the inner (i.e., body-facing) surface or the outer-facing surface of the circumferential anchoring member at the connection zones 148.

In the embodiment illustrated in 13A-13C, the LDEs 146 may be joined to the garment-facing surface of the core 126 at attachment zones 148. The LDEs 146 may be joined to the core 126 by any suitable means known in the art. For example, the LDEs 146 may be joined to the core 126 by any suitable adhesive, cohesive, or the like. Alternatively, the LDEs 146 can be joined to the wearer-facing surface of the core 126.

Figure 13D:
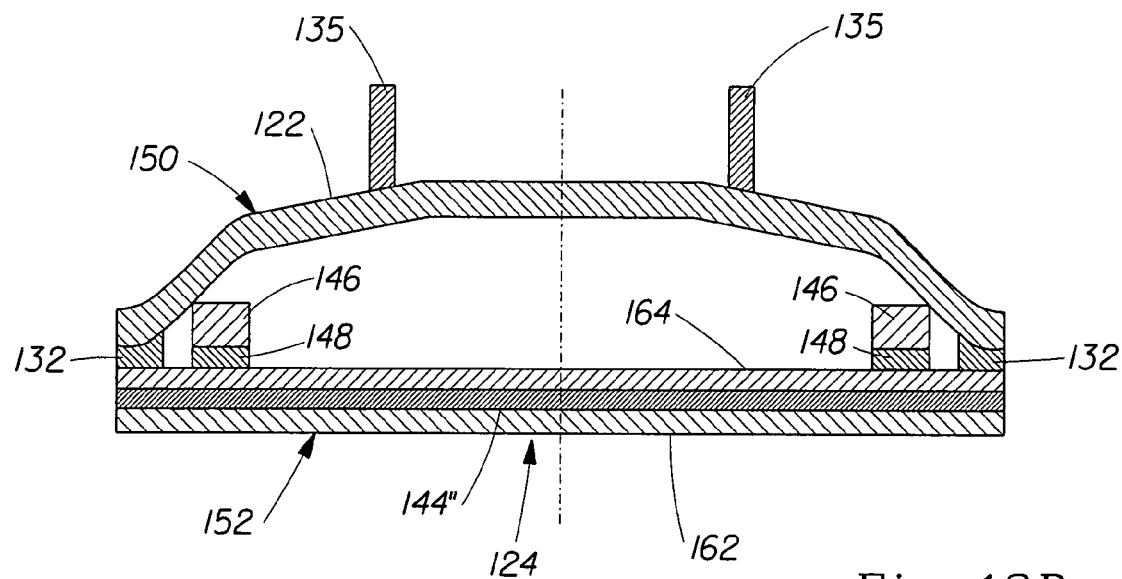
FIG. 13D illustrates a cross-sectional view of the disposable absorbent article of FIG. 13A, according to the present disclosure.
Figure 13E:
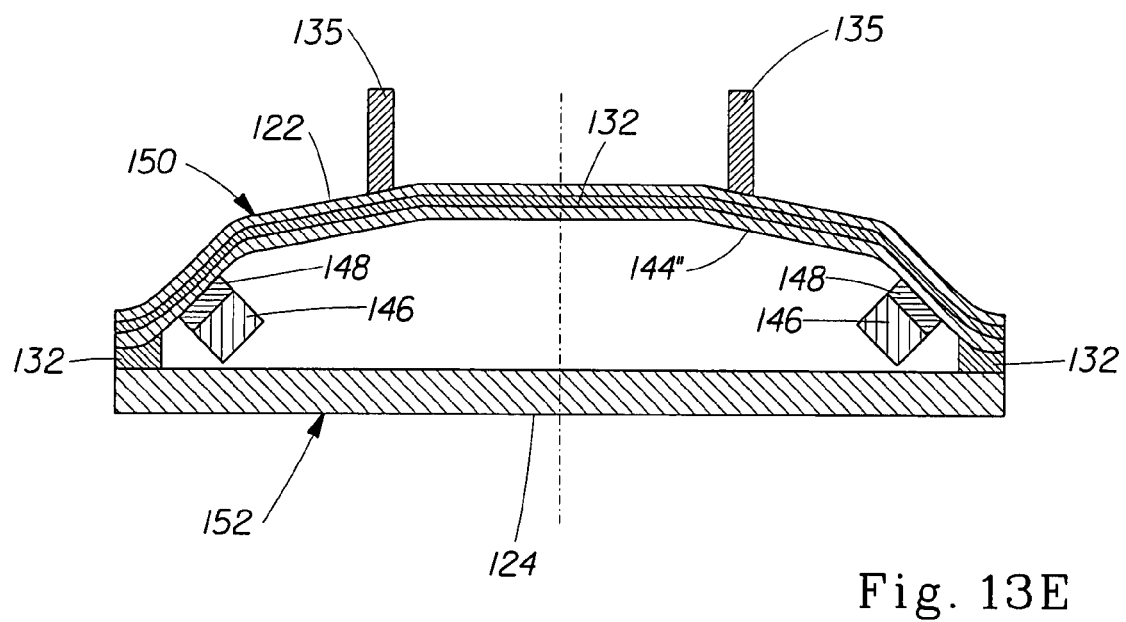
FIG. 13E illustrates a cross-sectional view of the disposable absorbent article of FIG. 13A, according to the present disclosure.

In the embodiment illustrated in FIG. 13A, the topsheet 122 can be joined to the outer cover 124 along the perimeter of the absorbent article 120 with an adhesive. Alternatively, the topsheet 122 can be joined to the outer cover 124 in any area in which the topsheet 122 and outer cover 124 overlap, so long as the bonded area lies outside the core 126. However, the bonds should be constructed such that movement or otherwise suitable operation of the anchoring system 142 is unencumbered and, preferably, such that the bonded region remains stretchable As described above, the anchoring bands 144' and/or 144" can be attached to the body facing side of the outer cover 124, as illustrated in FIG. 13C. This outer cover 124 can be formed from a nonwoven or a laminate of a nonwoven and a water-impermeable, breathable film. If the outer cover 124 is formed of multiple layers 164, 162, e.g. breathable film and nonwoven, the CAM or a portion thereof, e.g. anchoring band 144" could alternatively be embedded in between these two layers as illustrated in FIG. 13D. The CAM or a portion thereof, e.g. anchoring band 144", can also be either attached on one side of the topsheet 122 as illustrated in FIG. 13E, or embedded between two layers that are part of a multi-layered topsheet. The CAM or a portion thereof can be attached to the topsheet 122 and/or outer cover 124 at discrete locations or can be fully attached as appreciated by one having ordinary skill in the art. Partial bonding of the CAM to the topsheet 122 or outer cover 124 may allow the CAM to stretch more freely.

A suitable outer layer 162 (shown in FIG. 13D) is available from Corovin GmbH, Peine, Germany as supplier code A18AH0, and a suitable inner layer 164 is available from RKW Gronau GmbH, Gronau, Germany as supplier code PGBR4WPR. While a variety of outer cover configurations are contemplated herein, it would be obvious to those skilled in the art that various other changes and modifications can be made without departing from the spirit and scope of the invention.

With regard to FIG. 13D, where the outer cover 124 comprises a bi-laminate, the outer layer 162 can be made of a soft, non-woven material, while the inner layer 164 can be made of a substantially liquid-impermeable film. The outer layer 162 and the inner layer 164 can be attached together by adhesive or any other suitable material or method. Accordingly, in some embodiments, the CAM or portion thereof, e.g. anchoring band 144", can be joined to the inner surface of the inner layer 164.

If the inner layer 164 is liquid-impermeable, then the outer layer 162 need not be liquid-impermeable and can be formed from a traditional bi-axially stretchable material or a biaxially stretchable synthetic fibrous web material, thereby simulating conventional underwear. The laterally outer ends of the outer layer 162 can be attached to the laterally outer ends of the topsheet 122 by any suitable means known in the art, for example, via adhesive, cohesive, or the like.

Accordingly, as illustrated in FIG. 13D, the CAM or portion thereof, e.g. anchoring band 144" can be attached to the outer cover 124 laminate. In these embodiments, the LDEs 146 may be joined to the inner-facing surface of the inner layer 164 in the manner described above, thereby operatively coupling the core 126 to the circumferential anchoring band 144".

Referring now to FIG. 13E, in particular, the CAM or portion thereof, e.g. 144", can be attached to the garment-facing surface of the topsheet 122 via any suitable means known in the art, for example via adhesive, cohesive, or the like. The laterally outer ends of the CAM may be, in turn, attached to the outer cover 124 via adhesive, cohesive, or the like 132. The LDEs 146 may be, in turn, connected to the exposed garment-facing surface of the CAM or portion thereof, e.g. 144", at connection zones 148. In this illustrated embodiment, the topsheet is preferably stretchable or elastic, and more preferably biaxially stretchable or elastic.

In this case, the topsheet 122 can be fabricated as a biaxially stretchable layer. The LDEs 146 can also be partly or fully attached to the topsheet 122, or integrated into the topsheet by fabricating the topsheet 122 with recoverable biaxial stretchability at low forces everywhere except at the location where the topsheet 122 would overlap the LDEs 146 if the discrete LDEs were present, as described above with reference to the outer cover 124.

It should be appreciated that the CAM need not be a discrete structure, but could instead comprise a mechanically, thermally, or chemically treated portion of the outer cover 124 (i.e., an integral structure) to provide the desired structural properties described herein. For example, during the process of making a biaxially stretchable outer cover 124, a portion can be kept inextensible (e.g., where the outer cover overlaps the CAM) as discussed with regard to FIG. 8. Alternatively, a first portion of the CAM may be a discrete band or other separate element that is attached to the chassis 121, while a second portion of circumferential anchoring member is integral with the outer cover 124 to which the discrete band or other separate element is attached.

The LDEs 146 can be configured as described herein. For example, the LDEs 146 and/or CAM 144 may be joined to the outer cover 124 as discrete elements or may be integral with the outer cover 124 as described previously.

Figure 14:
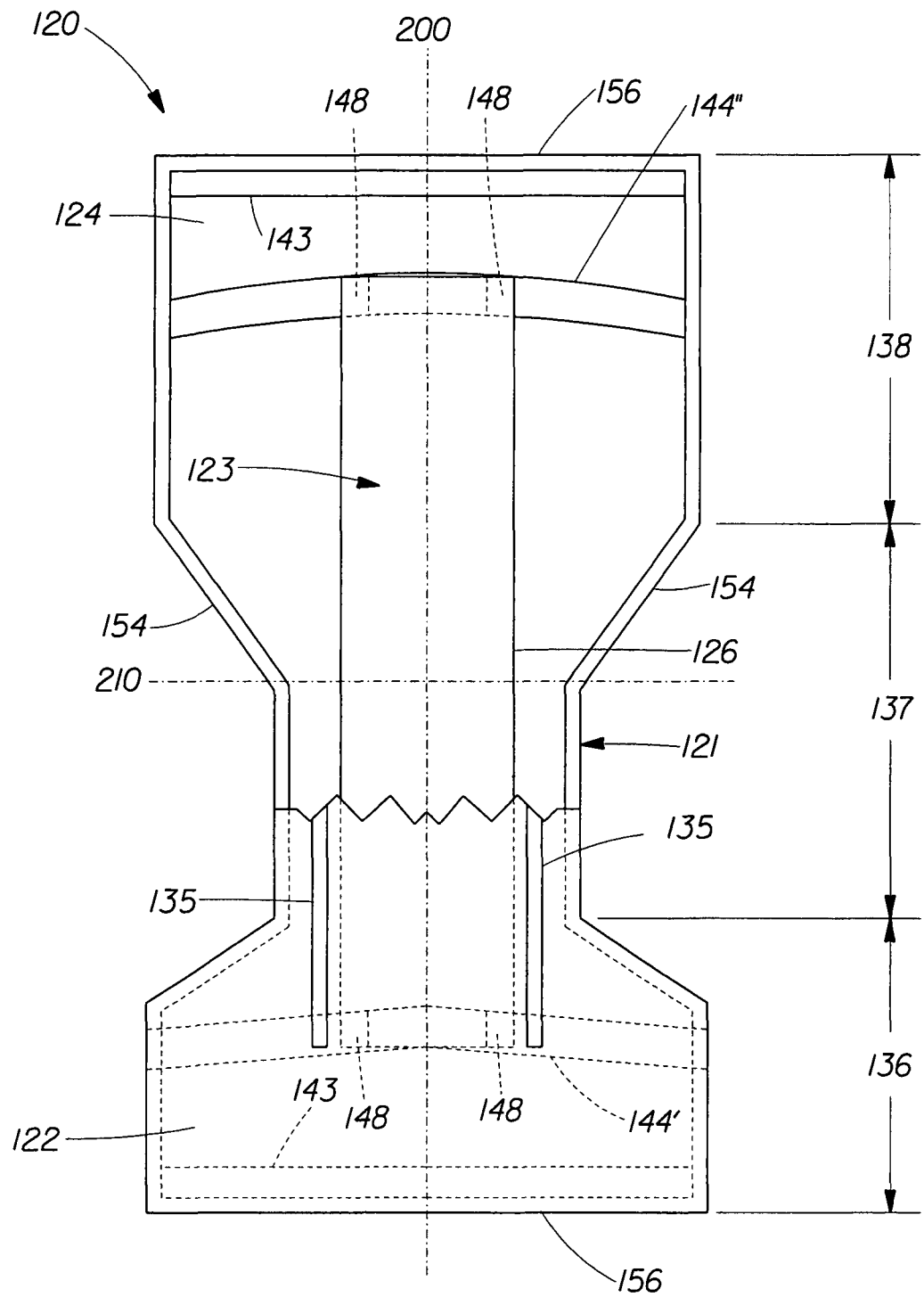
FIG. 14 illustrates a plan view of an embodiment of disposable absorbent article with an absorbent core and an anchoring system, according to the present disclosure.

Referring now to FIG. 14, embodiments are contemplated where anchoring bands 144' and/or 144" are directly joined to a core assembly. For example, the anchoring bands 144' and 144" may be joined to the core assembly 123 without the use of LDEs. Therefore, in some embodiments, the force from the core assembly can be directly transmitted to the anchoring bands 144' and/or 144" via connection zones 148. Additionally, embodiments comprising waist covers as discussed heretofore may be utilized in the absorbent articles configured in accordance with FIG. 14. Also, in these contemplated embodiments, the CAM 144 or portion thereof may be joined to the waist cover(s) or may be integral with the waist cover(s).

As shown in FIG. 14, in some embodiments, one or both longitudinal ends of the core 126 can extend from the first anchoring band 144' to the second anchoring band 144" (it should further be appreciated that the core 126 could extend beyond anchoring bands 144' and 144"). The anchoring bands 144' and/or 144" may be joined to the core 126 by any suitable means known in the art. Some suitable examples include adhesives, cohesives, heat seals such as ultrasonic bonds, high pressure bonds, RF (radio frequency) bonds, hot air bonds, heated point bonds, and the like as appreciated by one having ordinary skill in the art.

Figure 15A:
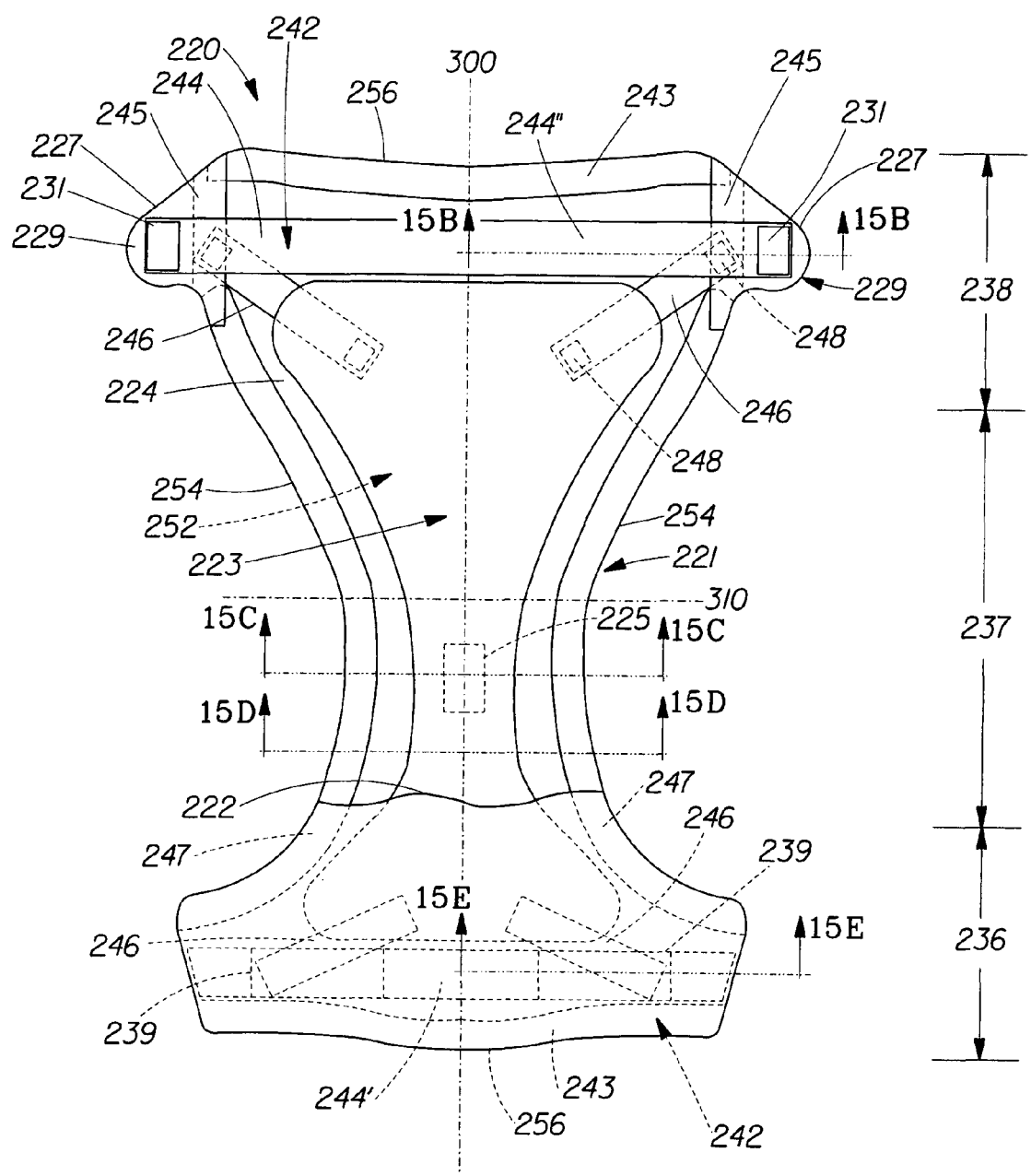
FIG. 15A illustrates a plan view of an embodiment of disposable absorbent article with an absorbent core and an anchoring system, according to the present disclosure.

Referring now to FIGS. 15A-15G, the present inventors recognize that the principles of the present invention as described above with respect to pant-like garments are equally applicable to garments, such as absorbent articles, that are configured as taped diapers (i.e., diapers that are not necessarily pre-closed within a package of absorbent articles). While some of the description above pertaining to pant-like garments is included in the description below of taped diapers for the purposes of form and clarity, the omission of other portions above from the description below does not imply that those omitted portions are not, or cannot be, incorporated into a taped diaper. Rather, the omitted portions are not described below to minimize redundant description throughout this document. Accordingly, unless otherwise specified, it should be appreciated that all features described above with respect to the pant-like absorbent articles can also be incorporated into taped diapers. Furthermore, unless otherwise specified, it should be appreciated that all features described below with respect to taped diapers can also be incorporated into pant-like garments. For the purposes of form and clarity, a taped absorbent article 220 is illustrated in FIG. 15A with like reference numerals corresponding to similar elements of FIGS. 1A-1C incremented by 200.

As shown in FIG. 15A, the absorbent article 220 has a central longitudinal centerline 300 and a central lateral centerline 310. The absorbent article 220 may include a substantially hourglass-shaped chassis 221 having a first, or front, waist region 236, a second, or back, waist region 238 opposed to the front waist region 236, and a crotch region 237 located between the front waist region 236 and the back waist region 238. The waist regions 236 and 238 generally comprise those portions of the diaper 220 which, when the diaper 220 is worn, encircle the waist of the wearer. The waist regions 236 and 238 can include elastic elements such that they gather about the waist of the wearer to provide improved fit and containment. The crotch region 237 is that portion of the diaper 220 which, when the diaper 220 is worn, is generally positioned between the legs of the wearer. The outer periphery of the chassis 221 is defined by lateral end edges 256 that can be oriented generally parallel to the lateral centerline 310, and by longitudinal side edges 254 that can be oriented generally parallel to the longitudinal centerline 300 or, for better fit, can be curved or angled, as illustrated, to produce an "hourglass" shaped garment when viewed in a plan view. In some embodiments, the longitudinal centerline 300 may bisect the end edges 256 while the lateral centerline 310 may bisect the side edges 254.

The chassis 221 can comprise a liquid pervious topsheet 222, and a liquid impervious outer cover 224 joined to the topsheet 222 proximal the lateral end edges 256 and the longitudinal side edges 254 via any suitable method known in the art. Some suitable examples include adhesives or cohesives. While adhesive or cohesive may be used to connect various absorbent article components as illustrated and described herein, one having ordinary skill in the art will appreciate that any suitable alternative attachment mechanism can facilitate such connections. Examples of suitable alternatives include, but are not limited to, thermal bonds, RF (radio frequency) bonds, pressure bonds, ultrasonic bonds, welds, stitching, and the like.

A cover 247 can be disposed about the side edges 254 that provide the periphery of the leg openings once the diaper 220 is closed, and thus engage the wearer's legs during use. Similarly, as shown, in some embodiments, a cover may similarly be disposed about the end edges 256 that provide the periphery of the waist opening once the diaper 220 is closed, and thus engages the wearer's waist during use. In some embodiments, the cover 247 can be elastic and joined to the outer cover 224 while the cover 247 is under tension such that upon relaxation gathers the side edges 254. Finished outer leg cuffs and waist edges are discussed in U.S. Pat. No. 5,797,824 and U.S. Pat. No. 7,013,941, while the latter also discusses methods and an apparatus for applying the material.

As described above with respect to absorbent article 220, the outer cover 224 can advantageously be bi-axially stretchable, thereby enhancing both the comfort of the diaper 220 on the wearer and the conformability to the wearer's anatomy during movement. In some embodiments, a substantially hourglass-shaped absorbent core assembly 223 can be positioned between the topsheet 222 and the outer cover 224. In some embodiments the core assembly 223 can be configured similar to the core assembly 23 described heretofore.

As illustrated in FIG. 15C, in some embodiments the core assembly 223 can be "tacked" (either via an adhesive, cohesive, or the like) to the outer cover 224 at one or more discrete locations 225, where wearer movement is unlikely to cause the connection between the core assembly 223 and the outer cover 224 to restrict outer cover stretchability. These discrete locations are also referred to herein as regions of low motion. Tacking the core assembly 223 in this manner would assist in preventing substantial movement of the core assembly 223 relative to the wearer's body. One example of a location suitable to tack the core assembly 223 to the outer cover 224 includes the crotch region 237, and particularly proximal to the intersection of the longitudinal axis 300 and the lateral axis 310. As illustrated in FIG. 15D, the remaining regions of the core assembly 223 are not required to be attached to the outer cover 224. In some embodiments, the bond area between the core assembly 223 and the outer cover 224 can be between about 1 cm² and about 20 cm² or any individual number within the range. In some embodiments, the core assembly 223 may be bonded to the outer cover 224 wherein the bond area resemble a strip extending the substantial length of the core assembly 223 and being long and narrow.

Referring again to FIG. 15A, the diaper 220 can also include a waistband 243 that helps provide improved fit and containment, as is appreciated by one having ordinary skill in the art. The waistband 243 is that portion or zone of the diaper 220, which is intended to elastically expand and contract to dynamically fit the wearer's waist. The elastic waistband 243, in some embodiments, may form at least a portion of the end edge 256 of the diaper 220. Disposable diapers can be constructed so as to have at least one elastic waistband positioned in the front waist region 236 and/or back waist region 238. Furthermore, while in some embodiments the elastic waistband 243 or any of its constituent elements can include a separate element affixed to the diaper 220, the waistband 243 need not be separately affixed to the diaper 220, as described heretofore. The waistband 243 may be configured as described heretofore.

The diaper 220 can include a pair of side panels 227 that extend laterally outward from the longitudinal side edges 254 proximal the lateral end edge 256 in the back waist region 238. The side panels 227 can be attached to the chassis 221 at attachment zone 245 using any known attachment apparatus or, alternatively, the side panels 227 can be formed integrally with the chassis 221. The side panels 227 may be elastic in some embodiments. Additionally, in some embodiments, the diaper 220 may further comprise a pair of side panels extending laterally outward from the longitudinal side edges 254 in the first waist region 236. The side panels 227 may be discrete elements which are joined to the first waist region 236 and/or the second waist region 238. Alternatively, in some embodiments, the side panels 227 may be integral with a portion of the diaper 220. For example, the side panels 227 may comprise a portion of the topsheet 222, outer cover 224, and/or leg cuffs.

The disposable absorbent article 220 further comprises a fastening system 229 which can join at least a portion of the first waist region 236 with at least a portion of a second waist region 238, preferably to form leg and waist openings. The fastening system 229 also works with the waistband 243 to maintain lateral tension about the waist of the wearer. The fastening system 229 may comprise engaging components 231 which, in some embodiments, can be disposed on the side panels 227. The fastening system 229 may further comprise a receiving component 239 which, as illustrated, is disposed in the front waist region 236. The receiving component 239 can be integral with the chassis 221, or can be connected via a side panel extending outward from the chassis 221.

Any suitable engaging element 231 can be used in the present invention. An example of a suitable engaging element 231 comprises hook fastening material. The hook fastening material can mechanically engage fibrous elements of the receiving element 239 so as to provide a secure closure. A hook fastening material according to the present invention may be manufactured from a wide range of materials. Suitable materials include nylon, polyester, polypropylene, or any combination of these materials, or other materials as are known in the art.

A suitable hook fastening material comprises a number of shaped engaging elements projecting from a backing such as the commercially available material designated Scotchmate™ brand No. FJ3402 available from Minnesota Mining and Manufacturing Company, St. Paul, Minn. Alternatively, the engaging elements may have any shape such as hooks, "T's", mushrooms, or any other shape as are well known in the art. An exemplary hook fastening material is described in U.S. Pat. No. 4,846,815. Another suitable hook fastening material comprises an array of prongs formed of thermoplastic material. Hot melt adhesive thermoplastics, in particular polyester and polyamide hot melt adhesives, are particularly well suited for forming the prongs of the hook fastening material. The prongs, in some embodiments, can be manufactured using a modified gravure printing process by printing the thermoplastic material in its molten state onto a substrate in discrete units, severing the material in a manner that allows stretching of a portion of the thermoplastic material prior to severance, and allowing the stretched molten material to "freeze" resulting in prongs. This hook fastening material and methods and apparatus for making such a hook fastening material are more fully detailed in European Patent Application 0 381 087.

The fastening system 229 may be the primary fastening system for joining the front and back waist regions 236 and 238. However, the fastening system 229 may be used alone or in conjunction with other fastening means such as tab and slot fasteners, tape fasteners, snaps, buttons, and the like to provide different fastening characteristics. For example, the fastening system 229 may provide the disposable absorbent article 220 with a disposal means for fastening the disposable absorbent article 220 in a configuration convenient for disposal. Further, secondary fastening means may provide the disposable absorbent article 220 with a means for adjusting fit or may increase the strength of the connection between the front waist region 236 and the back waist region 238.

When the diaper 220 is worn on the lower torso of a wearer, the end edges 256 encircle the waist of the wearer while, at the same time, the chassis side edges 254 define leg openings that receive the legs of the wearer. The crotch region 237 is generally positioned between the legs of the wearer, such that the absorbent core assembly 223 extends from the front waist region 236 through the crotch region 237 to the back waist region 238.

It should be appreciated that the positions of the side panels 227 and the receiving elements 239 can be reversed with respect to the embodiment illustrated in FIG. 15A, such that the side panels 227 extend from the longitudinal side edges 254 proximal the lateral end edge 256 in the front waist region 236, while the receiving elements 239 are disposed proximal the lateral end edge in the back waist region 238. Alternatively still, a pair of side panels 227 can be disposed in both the front and back waist regions 236 and 238, with a pair of the side panels in a given waist region including a fastening member configured to engage the opposing side panels.

The present invention recognizes that the core assembly 223 is capable of absorbing substantial loads during use, and that the fit of conventional diapers can be worsened when the increased weight and resultant downward forces exerted on the core (and from the core to other diaper components) cause the absorbent article 220 to sag or otherwise be distended. Accordingly, referring again to FIGS. 15A-19B the diaper 220 includes an anchoring system 242 similar to the anchoring system 42 described above and illustrated with respect to absorbent article 20. Like anchoring system 42, the anchoring system 242 includes a circumferential anchoring member 244 (designated as 244' in the front waist region and 244" in the back waist region) that surrounds the wearer's body at the lower torso region, and a plurality of LDEs 246 connected between the core assembly 223 and the circumferential anchoring member 244. In some embodiments, the circumferential anchoring member 244 can be disposed longitudinally inboard of the elastic waistband 243. In some embodiments, the CAM 244 may form a portion of the end edge 256 of the diaper 220.

During use, when the core assembly 223 absorbs an excremental load, for example, a gravitational and/or inertial force is applied to the core assembly 223 which tends to push the core assembly 223 downward. The core assembly 223 transmits the force to the LDEs 246 which in turn distributes the force to the CAM 244. The CAM 244 in turn, transfers the force to the wearer's body (e.g., at the lower torso region). In embodiments comprising the BSOC, the BSOC can force-decouple a potential pathway between the core assembly 223 and the anchoring system 242 ensuring that the anchoring system 242 receives loads from the core assembly 223 only by the LDEs 246 as opposed to receiving loads from the core assembly 223 by both the LDEs 246 and the outer cover 224. In some embodiments, substantially all of the load from the core assembly 223 may be transferred to the CAM 244 via the LDEs 246. It will be thus appreciated that the anchoring system 242 enables the taped diaper 220 to achieve an enhanced, more comfortable and underwear-like fit relative to conventional diapers.

As shown in FIG. 15A, in some embodiments, the CAM 244 may comprise a first anchoring band segment 244' extending between opposing side edges 254 in the front waist region 236, and a second anchoring band segment 244" extending between opposing side edges 254 in the back waist region 238. While segments 244' and 244" can assume any one of a number of configurations as described heretofore with regard to the CAM and/or anchoring bands, in the illustrated embodiment, the segment 244' and 244' are substantially straight and extend laterally across the diaper 220.

As shown in FIGS. 15B and 15E, the CAM 244 can be attached to the inner surface (i.e., opposite the garment-facing surface 252) of the outer cover 224 via any suitable means known in the art, for example, adhesive or cohesive. When the fastening system 229 is closed to correspondingly close the taped diaper 220, the segments 244' and 244" are operatively connected to form the continuous CAM 244 that surrounds the wearer's lower torso region.

As shown in FIG. 15A, in some embodiments, the CAM 244 may comprise one or more connection zones 248 where the LDEs 246 are joined to the CAM 244. Similarly, connection zones 248 can exist where the LDEs 246 are joined to the core assembly 223. The LDEs 246 may be configured similarly to the LDEs 46 and 146.

In some embodiments, the LDEs 246 can comprise bands that are non-stretchable so as to transfer the gravitational and/or inertia forces at the core assembly 223 to the connection zone 248 of the circumferential anchoring member 244. In some embodiments, the LDEs 246 may comprise stretchable and/or elastic bands which transfer forces from the core assembly 223 to the CAM 244. For example, during loading of core assembly 223, if the modulus of the LDEs 246 were designed to stretch by the same amount as the added load would swell the core; this would prevent the anchoring system 242 from having an added load source from the core swelling.

In a particular embodiment illustrated in FIG. 15A, four LDEs 246 are connected at one end to the four corresponding corner regions, or any portion of the four quadrants formed by the intersection of the longitudinal 300 and lateral 310 axes of the article, of the core assembly 223. In the illustrated embodiment, the LDEs 246 are connected to the outer (i.e., garment-facing) surface of the core assembly 223. Alternatively, the LDEs 246 can be connected to the inner (wearer-facing) surface of the core assembly 223. As illustrated in FIG. 15A, the LDEs 246 can extend outward from the core 226 and toward the corresponding end edge 256 and terminate at opposing ends that are connected to the outer (i.e., garment-facing) surface or the inner-facing surface of the CAM 244 at the connection zones 248. The LDEs can be joined to the core assembly 223 and to the CAM 244 via any suitable method known in the art, for example, any suitable adhesive, cohesive, or the like. Similar to the embodiment discussed with regard to FIG. 6, embodiments are contemplated where the connection zones 248 may comprise a discrete intermediate material which can be non-stretchable, stretchable, or elastic, in order to allow the CAM 244 to receive the forces from the core assembly 223 while preventing the core assembly 223 from sagging away from the wearer's body during use.

The outer cover 224 represents a potential force transmission path between the core assembly 223 and the anchoring system 242, a force transmission path between the core assembly 223 and the leg perimeters, and a force transmission path between the anchoring system 242 and the waist perimeter. For enhanced operation of the anchoring system 242, it may be desirable to force decouple the above mentioned transmission paths utilizing a suitable outer cover 224. For example, a suitable outer cover 224 as previously discussed, is a BSOC.

As shown in FIG. 15F, in some embodiments, the first anchoring band segment 244' can overlap a portion of the second anchoring segment band 244". The receiving component 239 is joined to 244' which has distal edge 244A and a proximal edge 244B. In a fastened state, the engaging component 231 engages the receiving component 239.

In order for the LDEs 246A and 246B to be properly coupled into the CAM 244, the overlap between the anchoring bands 244' and 244" should be disposed between the connection zones 248 of the LDE 246A and the connection zone 248 of the LDE 246B. Additionally, in order for the LDEs 246A and 246B to be properly coupled into the CAM 244, the engaging component 231 should be disposed between the connection zones 248 of the LDE 246A and the connection zone 248 of the LDE 246B. For example, as shown, the engaging component 231 can engage the receiving component 239 adjacent to the distal edge 244A of the receiving component 239. This positioning represents the largest circumference possible in the CAM 244, when a corresponding engaging element is similarly affixed on the opposite side of the article.

In contrast, as shown in FIG. 15G, the engaging element 231 is disposed proximate to the connection zone 248 of the LDE 246B. This embodiment represents a larger configuration for the positioning of the engagement element 231 with respect to the connection zone 248 of the LDE 246B. Additionally, this positioning represents a smaller circumference of the CAM 244, when a corresponding engaging element is similarly affixed on the opposite side of the article.

Figure 16:
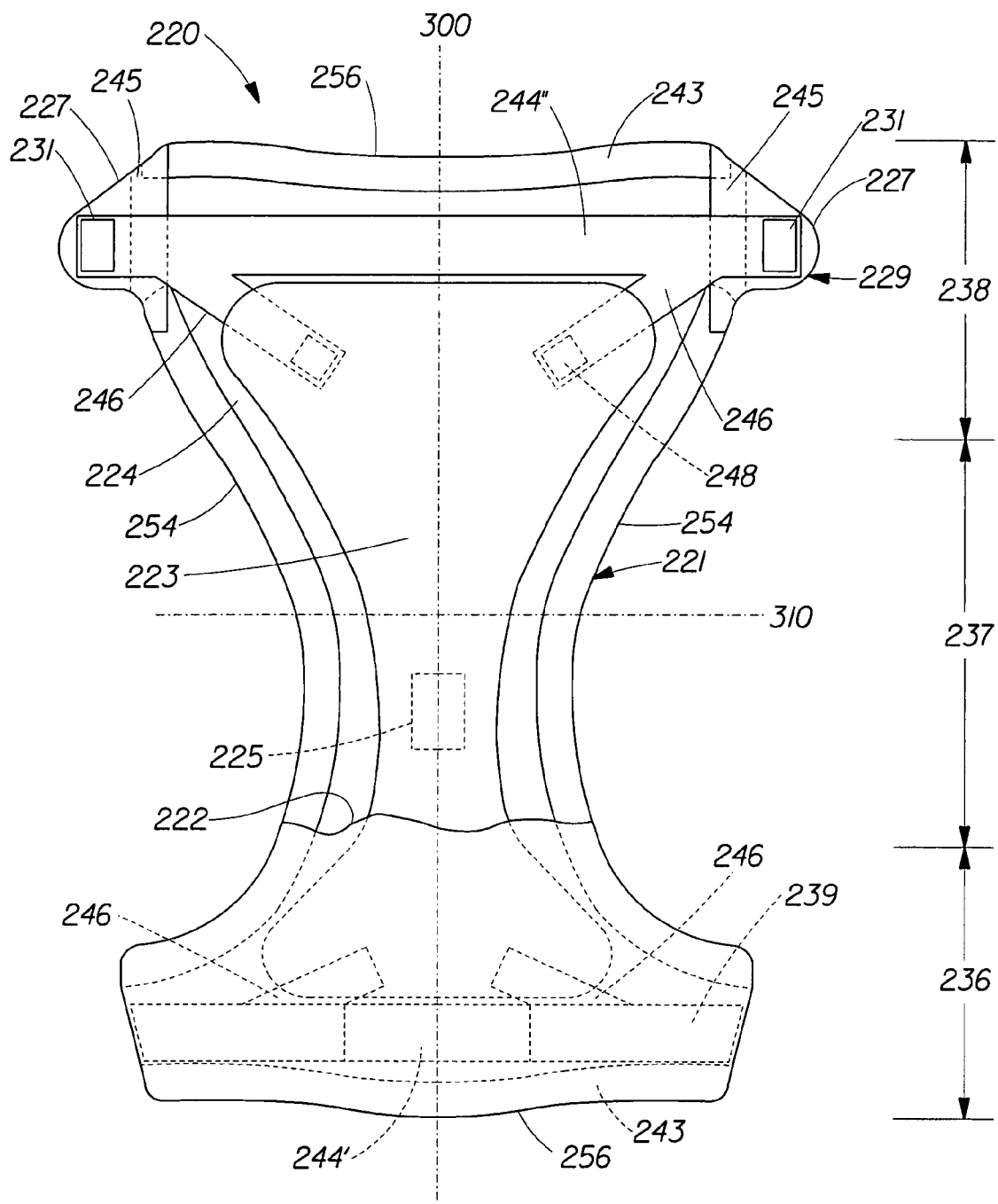
FIG. 16 illustrates a plan view of an embodiment of a disposable absorbent article with an absorbent core and an anchoring system, according to the present disclosure.

Referring now to FIG. 16, one alternative embodiment of the present invention recognizes that the LDEs 246 can be integrally connected to the circumferential anchoring member 244. For example, as shown, at least one of the LDEs 246 is integral with its corresponding anchoring band 244' and/or 244".

Figure 17:
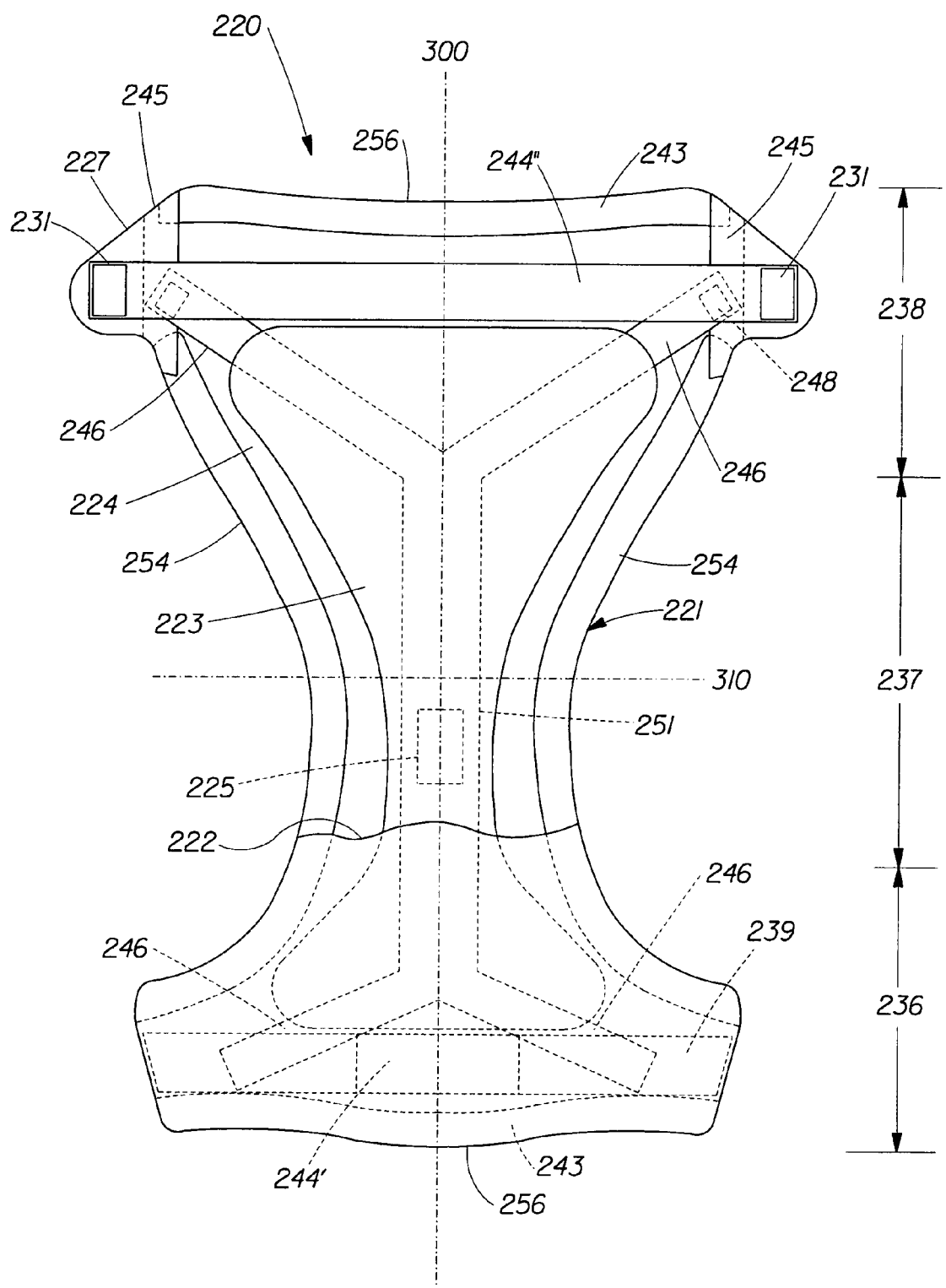
FIG. 17 illustrates a plan view of an embodiment of a disposable absorbent article with an absorbent core and an anchoring system, according to the present disclosure.
Figure 18:
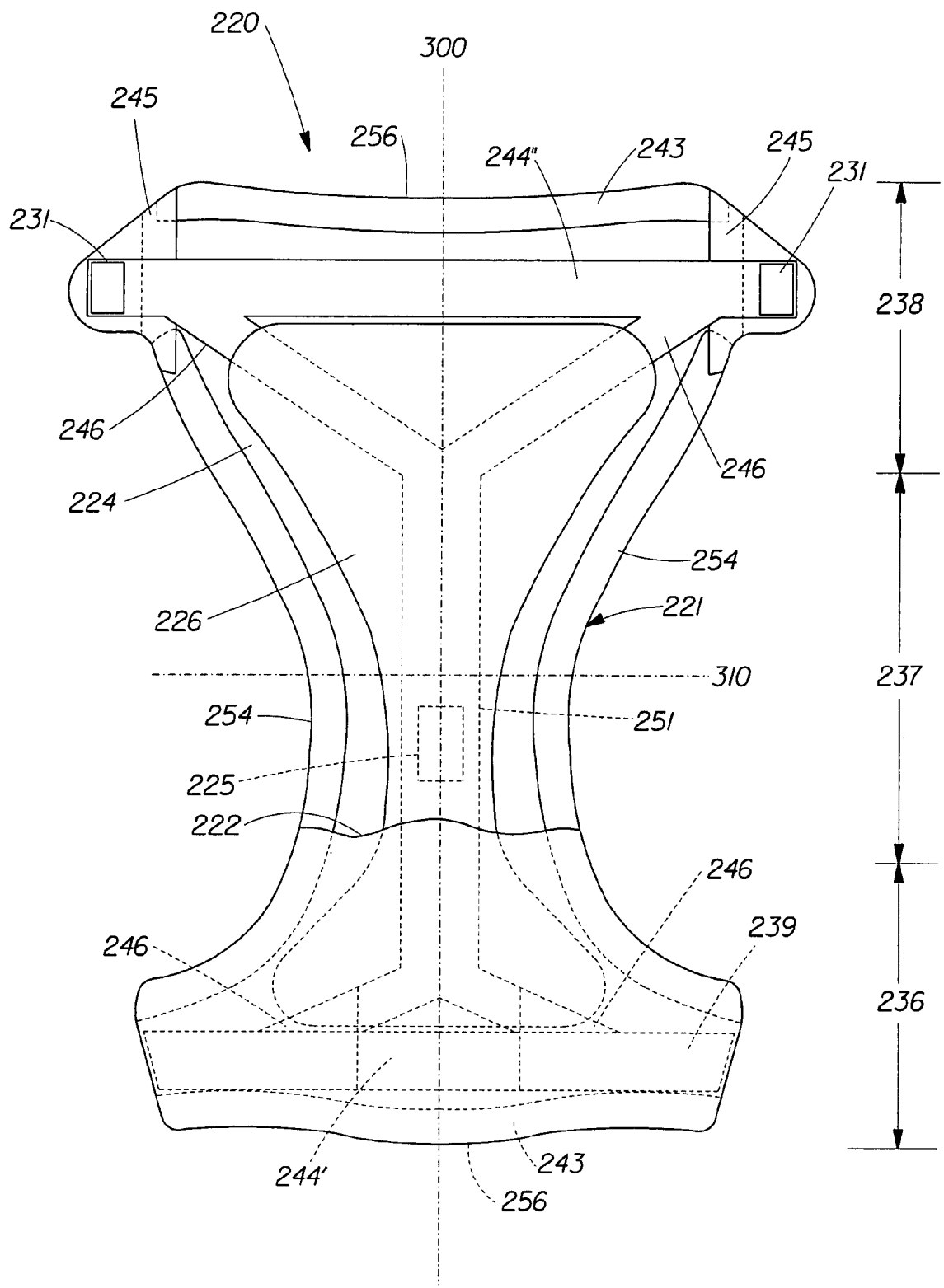
FIG. 18 illustrates a plan view of an embodiment of a disposable absorbent article with an absorbent core and an anchoring system, according to the present disclosure.

In some embodiments, as illustrated in FIG. 17, the LDEs 246 can be integrally connected via a spine 251 that extends longitudinally along the core assembly 223. In particular, at least a portion of, the spine 251 may be connected to the outer (garment-facing) surface of the core assembly 223 via an adhesive, cohesive, or suitable alternative and/or equivalent. In some embodiments, the spine 251 can be laterally centrally disposed on the core assembly 223, and can extend between the longitudinal outer edges of the core assembly 223. As illustrated, in some embodiments, the spine 251 terminates at both longitudinal ends short of the longitudinal end of the core assembly 223. The LDEs 246 may extend longitudinally and laterally outboard of the spine 251. Alternatively, in some embodiments, the spine 251 and LDEs 246 can be integrally connected to the circumferential anchoring band segments 244' and 244" as illustrated in FIG. 18.

The spine 251 can provide structural support for the core assembly 223. For example, conventional cores made up of airfelt may benefit from the incorporation of the spine 251.

As shown in FIG. 17, in some embodiments, the LDEs 246 may be discretely joined to the spine 251 and to the anchoring band segments 244' and/or 244". Alternatively, in some embodiments, the LDEs 246 may be integral with the spine 251 and discretely joined to the anchoring band 244' and/or 244". In still other embodiments, the LDEs 246 may be integral with the anchoring band 244' and/or 244" and discretely joined to the spine 251. In some embodiments, such as the embodiment of FIG. 18, the anchoring bands 244' and 244" and the LDEs 246 and the spine 251 can all be integral with each other. It should be appreciated that the spine 251 can be formed from the same material as LDEs 46, 146, and 246 or, if LDEs 246 are discretely connected to the spine 251, the spine can be formed from any suitable alternative material appreciated by one having ordinary skill in the art, including a portion of the outer cover subjected to less incremental stretching than the surrounding regions of the outer cover, as discussed heretofore.

Referring to FIGS. 19A and 19B, an absorbent article 320 is illustrated having reference numerals corresponding to like elements of FIGS. 1A-1C incremented by 300 for the purposes of clarity and convenience. The absorbent article 320 can include a pair of stretchable (e.g., in the machine cross direction) ears 317 (also referred to as an elastically stretchable side panel) that are attached (e.g., via mechanical, pressure, or ultrasonic bonding and/or glue etc.) to a chassis 321. The ears are thus stretchable in a direction substantially parallel to the lateral centerline 410.

Such stretchable ears are 317 are described, e.g., in U.S. Pat. No. 5,674,216. Typically they consist of a laminate of an (breathable) elastomeric film sandwiched (preferably with glue) between two layers of (preferably activatable) nonwoven such as DAPP or HEC. After lamination the ears 317 are activated, i.e., via ring rolling, as e.g. described in U.S. Pat. No. 5,156,793 or in U.S. Pat. No. 5,167,897 to allow the ears to stretch in the cross direction.

Hooks 319 (and associated stiffener element, if desired) may be applied to the ear during the process of manufacturing the article or when the ear laminate is produced. Suitable hooks 319 are available from Aplix Corporation as 963 hooks. Additionally, any hooks discussed heretofore may be utilized.

The ears 317 can be attached to an activatable auxiliary nonwoven 315 such as a DAPP or HEC. An example of a suitable DAPP nonwoven is available under the designation Softspan 200 by BBA Fiberweb, Brentwood, Tenn.

An auxiliary nonwoven layer 315 can join the absorbent assembly 323 and the ears 317 as shown in FIG. 19B. The auxiliary nonwoven may be folded over to encapsulate the outer leg elastics 363. In this embodiment, the auxiliary nonwoven 315 forms the front ear 313, the area to attach to back ears 317, and the material that encapsulates the curved outer elastics 363.

After the (curved) outer elastics 363 are attached to the biaxially stretchable outer cover 324 material and the auxiliary nonwoven 315 is folded over and (glue) bonded to the biaxially stretchable outer cover 324, the chassis 321 is selectively activated as e.g. described in U.S. Pat. No. 6,383,431 (Dobrin et al) in the machine direction and in the cross direction. The core assembly 323 can be tacked, if desired, to the outer cover 324 at location 339. An example of a suitable outer leg elastic 363 is available under the designation item#17087 available from Fulflex.

As seen in the drawing, some regions of the chassis 321 are not activated. These regions will form the chassis part of the anchoring system 342. The drawing clearly shows the circumferential anchoring member 344 and the load distribution elements 346 intended to link the core assembly 323 to the circumferential anchoring member 344. These regions are subjected to substantially less incremental stretching then the other regions of the outer cover. As can be seen in this execution the anchoring system 342 is made of the same structure as the whole chassis 321 via selective activation and is an intimate part of the outer cover 324.

In certain embodiments, the circumferential anchoring member 344 exhibits minimal strain under applied tension. An exemplary circumferential anchoring member 344 stretches only by 2% under a load of 0.9 N/cm.

If the unactivated biaxially stretchable outer cover material is, in its basic state, insufficiently resistant to extension, the strength of the circumferential anchoring member 344 may be increased via over-bonding the material. Over-bonding works especially well for nonwovens, but also works for laminates. Over-bonding, in essence, involves the application of heat and pressure to selected areas of the biaxially stretchable outer cover material, thereby melting part of the material and creating additional bond sites, or even film like structures (rather than the nonwoven structures).

It may be desirable to not activate the distal edges (the areas of the auxiliary nonwoven 315 that extend beyond the biaxially stretchable outer cover 324) of the auxiliary nonwoven 315. If said distal edges are not activated the web maintains a portion that has a relatively high modulus. This can be advantageous for web handling during the process of manufacturing the absorbent article.

When activating the chassis 321, care should be taken to not to create too much fuzz (i.e., dust, lint, loose fibers/material), create pin-holes, or damage the outer elastics, while achieving the desired level of lateral and longitudinal extensibility.

Fuzz creation is undesirable for line hygiene reasons and because consumers associate low fuzz levels with durability. With respect to the creation of fuzz, it has been found that it is desirable to create less than 0.12 mg/cm$^2$ of fuzz. A suitable fuzz test method is disclosed in U.S. Pat. No. 5,433,826.

Fuzz creation can be minimized by selection of appropriate nonwovens, the right activation process settings (lower strain rates, less depth of engagement are preferred), and the way how the auxiliary nonwoven is combined/bonded with the biaxially stretchable outer cover. In certain embodiments, it is preferable that the bonding between the auxiliary nonwoven 315 and the biaxially stretchable outer cover is not too intimate. For example, spiral glue has been found to be an acceptable method of bonding. In addition it has been found that it is desirable to activate the chassis 321 while the (spiral) glue combining the auxiliary nonwoven with the biaxially stretchable outer cover is still hot to minimize fuzz and pinhole generation.

While in this execution the chassis 321 does not need to be liquid impermeable, it still has been found that it is desirable to have as few pin-holes as possible. One reason is that the absence of pinholes is a signal of quality to the consumer as well as a re-assurance that the product will not leak. In light of this it has been found that it is desirable to have less than 0.1 pinholes per linear meter of chassis. In broad terms, a pinhole is a part of the chassis 321 stretched to 10% in machine direction and to 10% in cross direction were the opacity is at least 10 units lower than the average, and the pinhole area is larger than 0.5 mm$^2$.

It has been found that in general the same considerations that reduce fuzz also reduce pin-holes. Beyond the considerations identical to the fuzz generation it has been found that if the biaxially stretchable outer cover has a layer that is the main contributor of the opacity of the biaxially stretchable outer cover (like a film or a layer of melt blown or nano fibers), then it is desirable that this layer have elastic properties.

One way of avoiding the destruction of elastics is to avoid activating in the areas in which the outer elastics are disposed. Another way is to decrease the depth of engagement in the areas containing the outer elastics.

If desired, a preferably chevron shape landing zone 339 may be attached (glued) to the biaxially stretchable outer cover. An example of a suitable landing zone is sold under the designation NALT 27 chevron shaped landing zone produced by Aplix.

In some embodiments, biaxially stretchable outer cover 324 materials provide enough loops of fibers on the outside, such that the hooks 319 can engage with the biaxially stretchable outer cover 324 without the need of an additional landing zone 339. For example, a biaxially stretchable outer cover 324 may comprise an SMS nonwoven that is activated in the region typically occupied by a landing zone and subsequently over-bonded to create sufficient strength in the lateral direction to form an integral landing zone from the outer cover material. In other embodiments, the landing zone can be extensible in both the longitudinal and lateral directions and may be glued to the center chassis prior to or after activation.

A contractible finished waistband (not shown in this figure) may be applied to the inside, outside, or both, of the center chassis. Any suitable waistband known in the art may be utilized.

After the chassis 321 is activated a self-contained (or "bucket") core assembly 323, such as that depicted in FIGS. 1A-1C, may be attached to the chassis 321 by attaching the core to the LDE(s) 346, the CAM(s) 344, and/or directly to the outer cover 324. FIG. 19A shows regions 332 where the core assembly 323 is preferably attached to the chassis 321 and additional regions 311 where the core assembly 323 may be attached to the chassis 321 in certain embodiments. While the drawing shows the attachment sites 332 as squares, the attachment regions may comprise any suitable shape. When attaching the core assembly 323 to the chassis 321, the desire to bond as little area as possible to allow the chassis 321 to stretch and conform to the wearers body as much as possible is balanced with the desire to bond as much as possible, so that the core assembly 323 does not easily separate from the rest of the absorbent article 320.

One preferred way of attaching the core assembly 323 to the chassis 321 is to sandwich the core assembly 323 in the front and back regions 336 and 338 between the center chassis 321 and an optional waist cover 307. This way the core assembly 323 can not flip over, but by making the waist cover 307 extensible at least in the machine direction the ability of the center chassis 321 to stretch and conform to the wearer's body is less restricted than by gluing the core assembly 323 to the center chassis 321.

The waist cover 307 can be configured as discussed heretofore with regard to the waist cover 1523 (shown in FIGS. 11 and 12A). Additionally, in some embodiments, the CAM 344 and/or LDEs 346 can be attached to the waist cover 307 instead of the outer cover 324, thus significantly improving outer cover 324 aesthetics and product conformity, especially in the longitudinal direction. In some embodiments, the CAM 344 and/or the LDEs 346, or a portion thereof, can be integral with the waist cover 307. For example, portions of the waist cover 307 which are not the CAM 344 and/or the LDEs 346 may be incrementally stretched more so than the CAM 344 and/or the LDEs 346.

After the core assembly 323 has been attached to the chassis 321, the back ear 317 may be attached and the side notch may be cut out. After this the diaper 320 may be cut, folded, and put into bags.

The advantage of making the diaper 320 this way is that by assembling the absorbent article in the described sequence, there is always a part of the web that has a relatively high elastic modulus, providing easier web handling at high line speeds.

While a rectangular shaped core assembly 323 is relatively easy to fabricate, it can be desirable for the absorbent materials contained inside the core assembly 323 (e.g., nonwoven acquisition layers, fibrous acquisition layers, cellulose fibers, superabsorbent polymers, nonwoven forming or containment layers, etc.) to be shaped. Shaped absorbent materials conform much better to the wearer's anatomy; give the impression of less bulk between the legs and the impression of a better fitting product.

Specifically it has been found that it is desirable that the width of the absorbent materials in the region of the wearer crotch. i.e., the width of the core assembly in the crotch region is no greater than about 50 mm wide (independent of the age of the wearer). Alternatively, the width of the core in the crotch region may be up to about 70 mm, or even about 90 mm, in come embodiments.

An additional advantage of a relatively narrow core assembly in the crotch region 337 is that the effective cuff height of the barrier leg cuffs is increased.

Similarly, it has been found that it is desirable for the absorbent materials to be as wide as 110 mm, or even 130 mm in the front region 336 and in the back region 338 (for babies). For adults it may be desirable to spread the absorbent materials in the front and in the back even further.

The illustrated embodiment can be made from the following materials in accordance with one aspect of the invention.

Variations to the embodiment illustrated in FIGS. 19A-19B could be implemented. For instance, the bucket core assembly 323 could be discrete (i.e., not run the full length of the chassis 321). Furthermore, the biaxially stretchable outer cover 324 could be folded over and replace the auxiliary nonwoven. Additionally, rather than attaching the stretch back ears 313, the biaxially stretchable outer cover 324 could extend the full width of the article and comprise stretch elements. Finally, rather than making the anchoring system 342 out of the biaxially stretchable outer cover 324 via selective activation one could add an anchoring system made of a nonwoven or of an elastomeric film/nonwoven laminate attached separately to the core assembly as described herein.

Figure 20A:
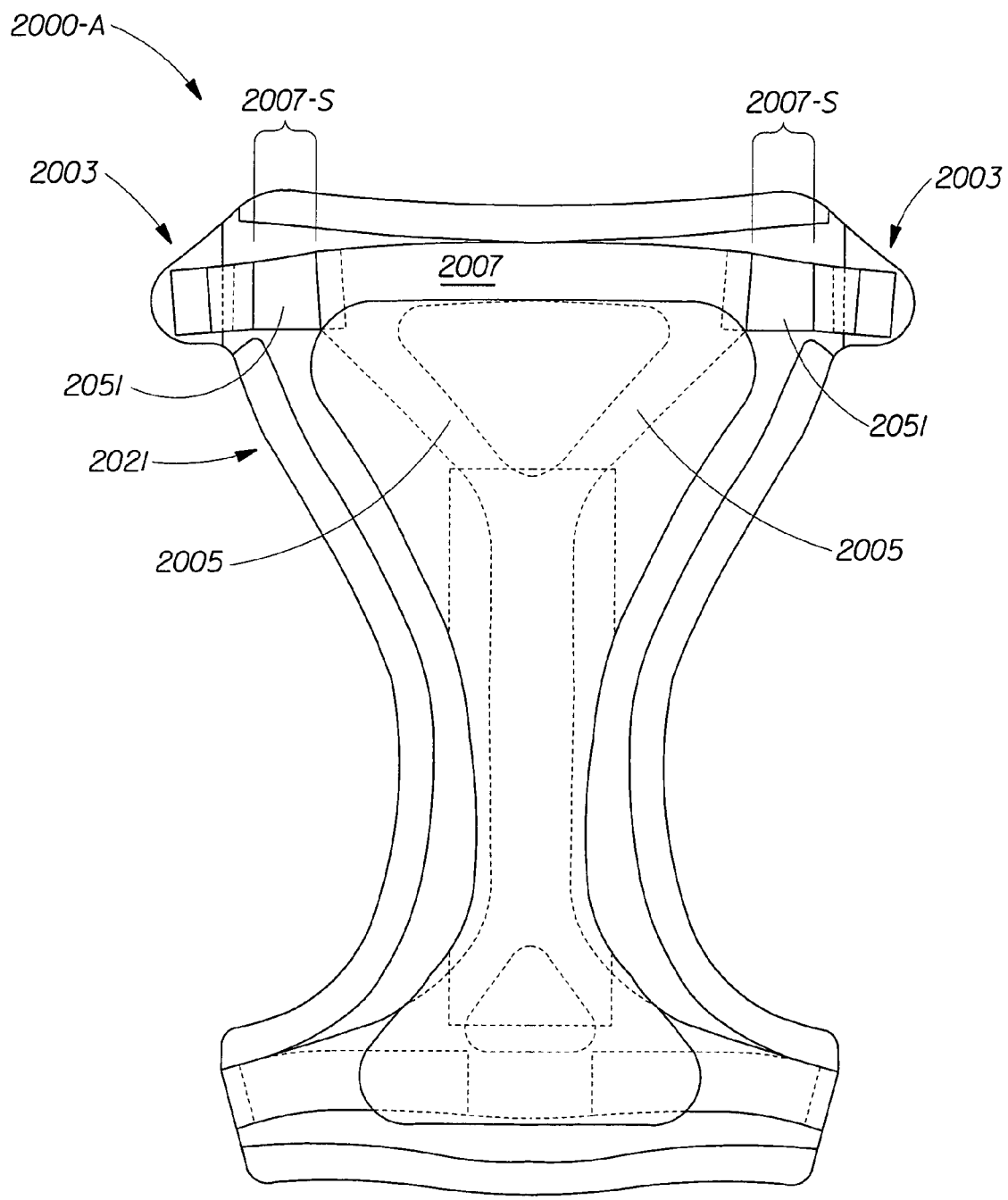
FIG. 20A illustrates a plan view of an embodiment of disposable absorbent article with an anchoring system, including a stretchable portion, according to the present disclosure.

FIG. 20A illustrates a plan view of an embodiment of disposable absorbent article 2000-A with side fasteners 2003 and an anchoring system 2021. The anchoring system 2021 includes a CAM 2007 and LDEs 2005. The anchoring system 2021 includes stretchable portions 2051 including stretchable CAM portions 2007-S, disposed laterally outboard of intersections between the CAM 2007 and the LDEs 2005.

Figure 20B:
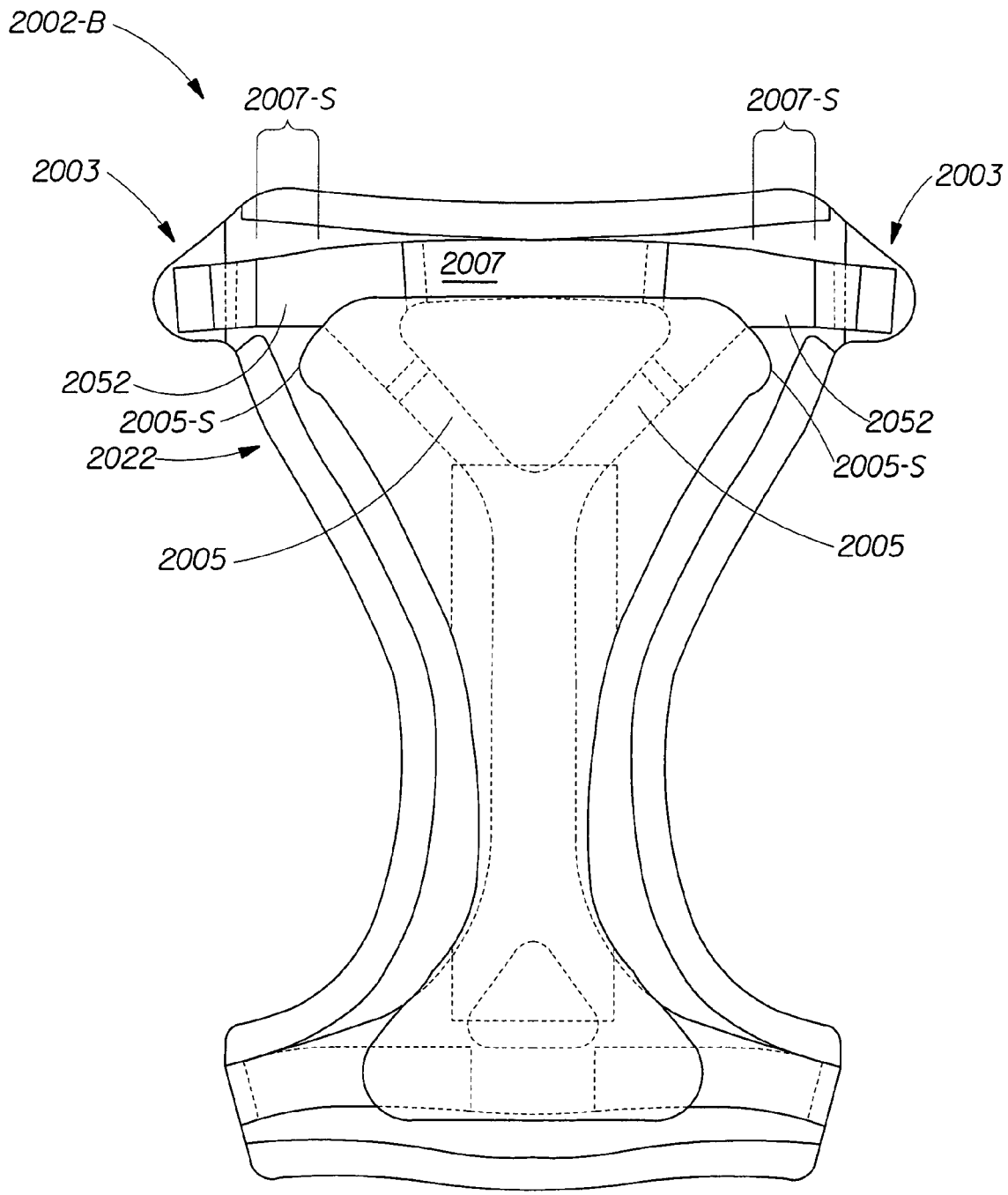
FIG. 20B illustrates a plan view of an embodiment of disposable absorbent article with an anchoring system, including a stretchable portion, according to the present disclosure.

FIG. 20B illustrates a plan view of an embodiment of disposable absorbent article 2000-B with side fasteners 2003 and an anchoring system 2022. The anchoring system 2022 includes a CAM 2007 and LDEs 2005. The anchoring system 2022 includes stretchable portions 2052 including stretchable CAM portions 2007-S and stretchable LDE portions 2005-S, disposed through intersections between the CAM 2007 and the LDEs 2005.

Figure 20C:
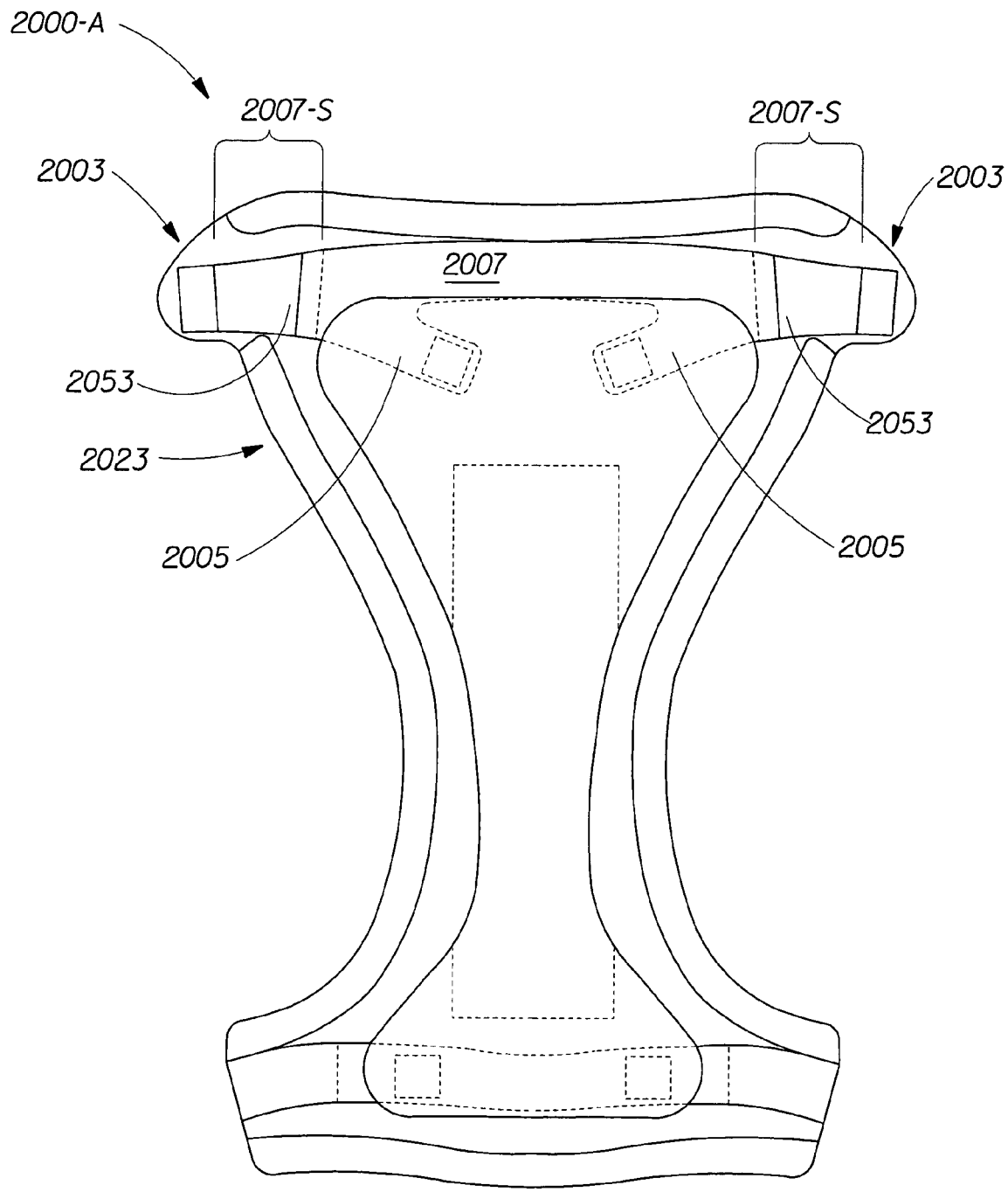
FIG. 20C illustrates a plan view of an embodiment of disposable absorbent article with an anchoring system, including a stretchable portion, according to the present disclosure.

FIG. 20C illustrates a plan view of an embodiment of disposable absorbent article 2000-C with side fasteners 2003 and an anchoring system 2023. The anchoring system 2023 includes a CAM 2007 and LDEs 2005. The anchoring system 2023 includes stretchable portions 2053 including stretchable CAM portions 2007-S, disposed laterally outboard of intersections between the CAM 2007 and the LDEs 2005.

Test Methods

Hysteresis Test for Elastic Properties (i) Sample Preparation for the Elastomeric Material Samples dimensions are as described below.

BSOC—(1" width by 3" length)

Topsheet (1" width by 3" length)

CAM—(width of the CAM generally parallel to the longitudinal axis of the diaper by 3")

LDE—(width of the LDE by 3")

Hysteresis Test for the Elastomeric Composite

A commercial tensile tester from Instron Engineering Corp., Canton, Mass. or SINTECH-MTS Systems Corporation, Eden Prairie, Minn. (or a comparable tensile tester) is used for this test. The instrument is interfaced with a computer for controlling the test speed and other test parameters, and for collecting, calculating and reporting the data. The hysteresis is measured under typical laboratory conditions (i.e., room temperature of about 20° C. and relative humidity of about 50%).

The procedure for determining hysteresis involves the following steps:

1. choose the appropriate jaws and load cell for the test; the jaws are wide enough to fit the sample, typically 1" wide jaws are used; the load cell is chosen so that the tensile response from the sample tested will be between 25% and 75% of the capacity of the load cells or the load range used, typically a 50 lb load cell is used;
2. calibrate the tester according to the manufacturer's instructions;
3. set the gauge length at 25 mm;
4. place the sample in the flat surface of the jaws such that the longitudinal axis of the sample is substantially parallel to the gauge length direction;
5. the hysteresis test involves the following steps:
   a) pull the sample to 50% strain at a cross head speed of 10 in./min (254 mm/min)—first cycle loading
   b) hold at that strain for 30 seconds and return to 0% strain at the same crosshead speed—first cycle unloading
   c) allow the sample to remain at this strain for 1 minute; and
   d) pull to 50% strain at a constant rate of 10"/min (254 mm/min)—second cycle load
   e) hold at that strain for 30 seconds and return to 0% strain at the same crosshead speed—second cycle unloading From the data collected in step 5, the following two measurements are used:

a) first cycle force at 15% strain
   b) % set, which is defined as the strain at 0.05N in the second loading cycle. The 0.05N force is deemed sufficient to remove the slack but low enough to impart, at most, insubstantial stretch to the sample.

6. Record data for first cycle load at 15% strain
7. Record data for % set.

Air Permeability

Air permeability is determined by measuring the time in which a standard volume of air is drawn through a test specimen of a defined area at a constant pressure and temperature. This test is particularly suited to materials having relatively high permeability to gases, such as nonwovens, apertured films and the like. The air permeability test is performed according to ASTM D737-96 entitled "Standard Test Method for Air Permeability of Textile Fabrics" with the following test parameters. A TexTest FX3300 instrument is used. (Available by Textest AG in Switzerland (www.textest.ch), or from Advanced Testing Instruments in Spartanburg S.C., USA.) The test is conducted in a laboratory environment at about 22±2° C. and about 50% relative humidity. The test pressure drop is 125 Pascal and the test area is 38 cm$^2$. In this test, the instrument creates a constant differential pressure across the sample which draws air through the sample. The rate of air flow through the sample is measured in ft$^3$/ft$^2$/min (often called cfm or ft/min) or m$^3$/m$^2$/min (or m/min). For each sample, three replicates should be run, and the average result is reported.

Hydrostatic Head (Hydrohead) Pressure

The property determined by this test is a measure of the liquid barrier property (or liquid impermeability) of a material. Specifically, this test measures the hydrostatic pressure the material will support: when a controlled level of water penetration occurs. The hydrohead test is performed according to EDANA 120.2-02 entitled "Repellency: Hydrostatic Head" with the following test parameters. A TexTest Hydrostatic Head Tester FX3000 (available from Advanced Testing Instruments, Corp., Spartanburg, S.C., or by Textest AG in Switzerland (www.textest.ch)) is used. For this test, pressure is applied to a defined sample portion and gradually increases until water penetrates through the sample. The test is conducted in a laboratory environment at about 22±2° C. temperature and about 50% relative humidity. The sample is clamped over the top of the column fixture, using an appropriate gasketing material (o-ring style) to prevent side leakage during testing. The area of water contact with the sample is equal to the cross sectional area of the water column, which equals 28 cm$^2$. Water is pumped into the water column at a rate of 20 mbar/min. Thus, the sample is subjected to a steadily increasing water pressure on one surface. When water penetration appears in three locations on the other surface of the sample, the pressure (measured in mbar) at which the third penetration occurs is recorded. If water immediately penetrates the sample (i.e., the sample provided no resistance), a zero reading is recorded. For each material, three specimens are tested and the average result is reported.

In various embodiments of the present disclosure, an absorbent article with an anchoring system can have a backsheet, an absorbent core and a topsheet, provided with at least one opening adapted to receive fecal material, said topsheet and said opening thereof each having a front region and a back region, characterized in that said diaper comprises a genital coversheet, which in use covers the genitals, and which is positioned in, under or above said front region of the opening, whereby a void space is formable between the genital coversheet and the absorbent core, and whereby a void space is present between the topsheet and the absorbent core. Thus, the genital coversheet reduces the size of the opening.

Such a genital coversheet is typically urine permeable, so that the urine can pass through it immediately to the absorbent core of the diaper, and it preferably has a low rewet, so that the amount of urine passing back to the genitals is minimized. In another embodiment, an absorbent article, typically an adult or infant diaper or training pants comprising a backsheet, includes an absorbent core and a topsheet, and integral therewith a genital cover portion, said topsheet having a front region and a back region, and said topsheet comprising in part of said front region and part of said back region back region an opening, preferably a single opening, to receive fecal material, characterized in that said topsheet comprises in the front region a genital cover portion that is urine permeable (and that preferably can form a pocket and/or has the extendibility described herein for the genital coversheet) and that the topsheet comprises in the back region an urine-impermeable and feces-impermeable feces-retaining portion, having a mean pore size of less than 20 microns and a air-permeability of at least 3 Darcy, whereby there is a void space between the genital-cover portion of the topsheet and the absorbent core and between the feces-retaining portion of the topsheet and the absorbent core.

In various embodiments, an absorbent article with an anchoring system of the present disclosure can also be configured as described in US Pat. No. 6,482,191, which is hereby incorporated by reference.

Theory of Anchoring:

Those skilled in the art of absorbent articles will appreciate that the size and shape of the wearer has a substantial impact on the comfort and performance of an article in use. Absorbent articles are typically sized to fit a given segment of the human population and a range of sizes is offered to cover each target market for the product (such as infants, toddlers, small children or adults). Each size is intended to provide comfort and performance for all the wearers in the segment it is designed to fit. Anchoring is particularly sensitive to the shape and size of the wearer.

The present invention provides anchoring systems that are more robust across a size segment than the present art. Nevertheless, absorbent articles have many design tradeoffs and interactions which often lead to unintended and unexpected results from seemingly innocuous changes to a product design. While not wishing to be bound by theory, the inventors offer a theory herein to explain the principles behind various aspects of the present invention.

To help with description of locations on the wearer's body, a coordinate system for the wearer is defined. Detailed numerical coordinates need not be used in this disclosure, but the coordinate axes will provide the ability to qualitatively discuss relative locations. It is convenient to use the pelvis to base a coordinate system because the anchoring systems described herein are intended to remain in a fixed position about the pelvis. Note that the waist and leg perimeters of the diaper will contact surfaces of the body which are driven by the spine and legs and can move relative to the pelvis. Thus the body surfaces surrounding the spine and legs move and deform somewhat independently of the surface surrounding the pelvis. Thus during wear, the diaper perimeters at the waist and legs may move relative to the anchoring system of the present invention.

Figure 21:
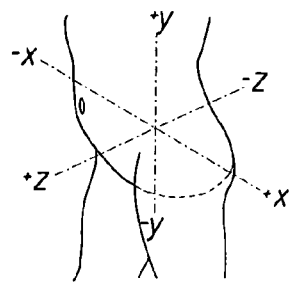
FIG. 21 illustrates a perspective view of a portion of a human body along with a coordinate system.

Referring to FIG. 21, the coordinate system is established relative to the pelvis as it is positioned in a baby standing upright. A baby is used as an exemplary wearer but the principles illustrated and described herein apply to all human wearers. The origin of the coordinate system is the center of gravity of the pelvis. The "y" axis is vertical (in line with gravity) with the positive direction pointing up. The "x" axis is oriented in the wearer's left-to-right direction with positive direction pointing to the wearer's left (thus when viewing the wearer from the front, positive "x" is toward the right). The "z" axis is in the front-to-back direction with the positive direction toward the front.

Unless stated otherwise, the wearer is assumed to be standing in the following description of the theory. It is also assumed that wearable articles are held in place on the body by the physics of mechanical contact. This limits the possible interactions between the wearer's body and the article to normal force and friction. The present invention is fully compatible with any method to favorably enhance the interaction in contact areas such as body adhesives and the like, but these are ignored during the discussion of theory.

From the moment a diaper is put on a body, various forces arise within the diaper and between the diaper and body. These forces come from many sources such as the initial taping forces, diaper mass, body movement, urination, bowel movements, and physical interaction with clothes and parents. The weight of an absorbent article can generate significant force in the negative y direction (downward) as it collects and stores bodily wastes. For example, a diaper designed for a toddler may weigh 50 grams initially when dry and typically 100 to 200 grams when changed. If the toddler were standing, this load force would tend to drag the diaper down the body unless there was an equal upward support reaction imposed on the diaper. Another important load force comes from deceleration that occurs from the impact of the feet hitting the floor when the toddler runs or jumps. The deceleration of the body would tend to drag the diaper down the body unless there was an equal upward support reaction generated on the diaper which decelerates at the same rate that the body decelerates so that the diaper will not move down the body. These two load forces are the target loads for the anchoring system of the present invention.

Load forces originating from the weight of the absorbent article typically originate in the lower half of the article; however, locations on the body that can successfully create support reactions (i.e., can support the load forces) are typically engaged by the upper half of the article. It therefore follows that a system designed to anchor the article may have to perform various functions such as, for example: 1) collecting load forces, 2) transmitting the load forces to parts of the body surface favorable for creating support reactions, and 3) arranging the load forces so that sufficient support reactions are generated.

One feature that distinguishes the various aspects of the present invention from the prior art is that these functions are carried out by an anchoring system made up of a network of anchoring bands and load distribution elements. Another feature includes the reduction of load stresses on other parts of the article. For example, the inclusion of a BSOC may reduce the tendency for the wearer's movement to also induce movement in the waist and leg perimeters of the article. Additionally, by reducing force transmission from the core assembly through the outer cover, the materials selected for the outer cover may include elastic/extensible materials which can provide an underwear like look and feel to the article while also delivering comfort and fit to the wearer.

Further, these networks can direct the load forces to the most desirable areas of the body for support in the most desirable directions that all together provide the needed support at the lowest tension and therefore maximum comfort.

Regarding the first role of the anchoring system, the theory assumes that the load forces are already collected and presented to the anchoring system as point sources. For those embodiments that have a core assembly such as 23 in FIG. 1A, there is sufficient structural support for the absorbent core so that the load forces arising from the distributed mass of the core and its contents can be "collected" to a few attachment points on the assembly. These attachments points can be designed to withstand the rigors that concentrated loads place on them. Those skilled in the art would recognize that other core structures may include a functionally equivalent structure to the containment member 28 in FIG. 1B to serve to collect the load forces so that attachments for transmitting the loads to the anchoring system will not destroy the attachment or core integrity during wear.

Regarding the second role, the transmission of load forces can be modeled in theory by abstract curved lines with no weight, width, thickness, or bending stiffness but possessing the axial properties of an ideal spring thus the ability to carry loads in tension. These theoretical "springs" are termed "load bands" or "force bands" herein. Loads are transmitted by load bands to those areas of the body that are suitable for creating support reactions. A load band has a length, a spring constant, and a connection point at each end. Connection points are endpoints of the load band which can be connected to other load bands or a load. Loads and other load bands that meet at a given connection point are free to rotate about the connection point without resistance in any direction except for the barrier imposed by the body surface.

Regarding the third role, anchoring can be described in terms of a load force inducing an opposing support reaction. Therefore areas of contact between the body and the anchoring system where the load forces and opposing support reactions meet are termed anchoring zones. The theory considers three different modes in which the body can generate support reactions in response to a load force in the anchoring zones. Each mode has a different relationship between the direction of the load force and the direction of support reaction. To some degree the three modes are complimentary, which in a properly engineered anchoring system, creates a more robust system than reliance on a single mode. The modes are termed "frictional", "geodesic", and "geometric". All three anchoring modes depend, at least in part, on the generation of a normal force when flexible materials are wrapped in tension on a curved surface. Geometric anchoring additionally uses stored elastic energy to create support forces.

In general, solid bodies that contact each other interact only by normal force and friction. A normal force is one that is directed perpendicular to the surface of contact. Friction is a force generated parallel to the surface of contact in response to a sliding force between the bodies. Friction requires normal force in order to operate. Thus a normal force is required for any type of support interaction in the anchoring zone. Since an anchoring zone is a contact zone, the load force transmitted to the anchoring band arrives at the anchoring zone parallel (tangential) to the surface of contact. A normal force forms in this anchoring zone if the surface of contact has a convex curvature in the axial direction of the anchoring band.

Figure 36:
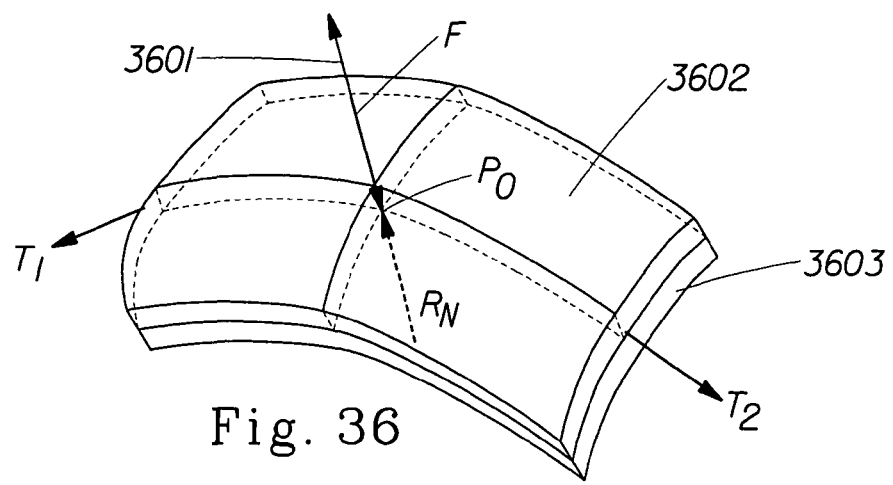
FIG. 36 illustrates a portion of an element of an anchoring system, according to embodiments of the present disclosure.

FIG. 36 shows an element of an anchoring band in an anchoring zone. The anchoring zone is depicted as a layer of diaper material 3602 tensioned over a curved element of the body. Only an outside layer of skin 3603 is represented. As shown in FIG. 36, the anchoring zone is the surface interface between the layer of diaper material and outside layer of skin. The band is tensioned along an axis indicated by $T_1$ and $T_2$. The tension and curvature cause a normal force/unit area, F, to form at every point there is tension and curvature. The body-side surface of the anchoring zone responds to F with a support reaction, $R_N$, of equal magnitude, which is also normal 3601 to the surface, but in the opposite direction. For clarity, the forces are shown only at point $P_0$, but integrating the force per unit area across the area will give a total normal force on the surface element. The normal force at a given point is proportional to the curvature of the surface and proportional to the tension in the band at that point.

The principles of geodesic and geometric anchoring are more easily described in the absence of friction, so with regard to the discussion pertaining to geodesic and geometric anchoring, an assumption is made that frictional forces are zero.

As stated previously, in theory, a force band may act as an ideal spring. When stretched across a curved surface between two points, the force band will seek a path that minimizes its potential energy. The potential energy of a spring being proportional to its stretched length, a stretched force band takes an equilibrium path that is the shortest path between the two points. The shortest path between two points on a curved surface is mathematically defined as a "geodesic". The geodesic formed between two points is called an "open" geodesic.

Some of the relevant properties of geodesics as defined by generally accepted mathematics will be used herein to describe the application of geodesic principles to the anchoring systems of the present invention. More information on geodesics and their mathematical properties can be found in texts on differential geometry and the theory of general relativity, for example, Barrett O'Neill, Elementary Differential Geometry Ch. 7 (Academic Press 2006); and James Foster & David J. Nightingale, A Short Course in General Relativity Ch. 2.1 (Springer Science and Business Media 2006).

On a convex, frictionless surface, a force band in tension will follow a geodesic path. The two points that define the force band are termed "endpoints". If the region between two endpoints on a surface contains a concave area, a force band under tension can bridge the concave area. The portions of the path that the force band contacts will be geodesics, and the portions of the force band spanning the contacted portions of the path will also be a geodesic because it is a straight line in space. In contrast, a mathematical geodesic would be forced to follow the concave surface and would not be able to bridge (span) the concave surface. Thus a mathematical geodesic would have a longer path than the force band where the shortest distance between the two endpoints included a concave surface. Although they are used in a similar fashion here, a geodesic is a geometric concept that has no means to carry tension; and a force band does. This explains why a force band bridges a concave region of a surface and a geodesic doesn't.

Figure 22:
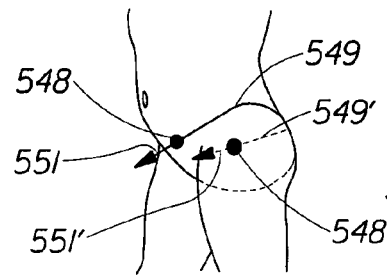
FIG. 22 illustrates a perspective view of a human body with force vectors relating to an anchoring system for a disposable absorbent article, according to the present disclosure.
Figure 23:
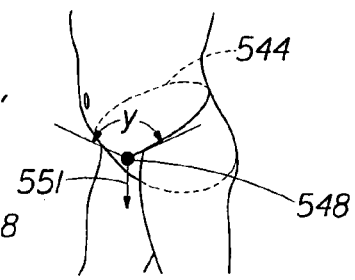
FIG. 23 illustrates another perspective view of a human body with force vectors relating to an anchoring system for a disposable absorbent article, according to the present disclosure.
Figure 37:
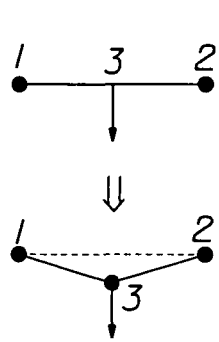
FIG. 37 illustrates a force band with a point load, according to embodiments of the present disclosure.
Figure 38:
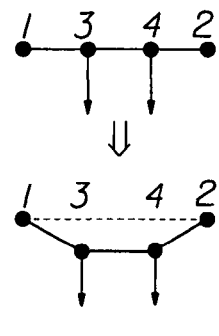
FIG. 38 illustrates a force band with two point loads, according to embodiments of the present disclosure.
Figure 39:
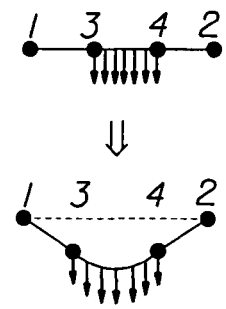
FIG. 39 illustrates a force band with a distributed load, according to embodiments of the present disclosure.
Figure 40:
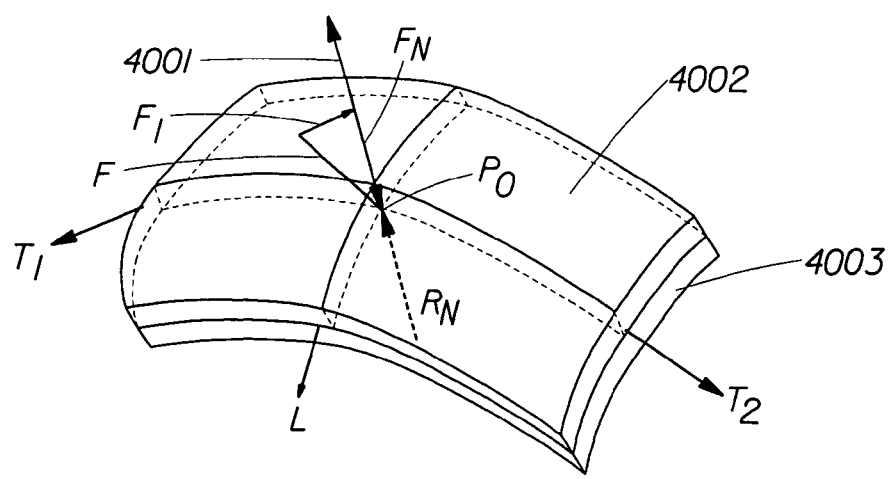
FIG. 40 illustrates another portion of an element of an anchoring system, according to embodiments of the present disclosure.

Force bands have some very useful properties for constructing anchoring systems because they follow geodesic surface pathways and because they carry tension. These properties have a direct bearing on how the anchoring system works. In the following discussion the surface is assumed to be a convex curved surface. In general what applies to a mathematical geodesic on a convex surface also applies to a force band on a surface with concave regions. Key aspects of mathematical geodesics as they relate to anchoring systems include:

1. The mathematical definition of a geodesic allows one to extend a geodesic beyond the two points that originally defined it, i.e., mathematically, a geodesic has no end other than where it intersects the edge of a bounded surface. For many closed surfaces, the extended geodesic may intersect itself forming a closed geodesic. FIGS. 22 and 23 show force bands on open and closed geodesics, respectively.
2. A closed geodesic may form an angle, $\gamma$, where it intersects itself (called a "corner"). Note that geometrically, only the circumferential path turns the corner. Both ends of the geodesic path theoretically continue straight through the corner and follow the mathematic definition of a geodesic as long as there is surface. In schematic anchoring systems, force bands typically end at the corner and the geodesic extensions are truncated and replaced by a single vector representing a load force. The corner itself is considered a connection point 548 where a load force or another force band can be attached (shown in FIG. 23).
3. A force band under tension following a closed geodesic, but with no load connections may form a continuous smooth curve with no corner (therefore $\gamma=\pi$ radians). This condition is a shortest closed path. A closed geodesic with a corner has a longer path compared to a closed geodesic that passes through the corner at $\gamma=\pi$.
4. Another consequence of the mathematical definition of geodesics is that the only force a tensioned force band places on a frictionless surface is normal to the surface. For this reason anchoring by normal force is termed the "geodesic anchoring mode".
5. The geodesic path does not depend on tension, i.e., increasing the tension of a force band has no tendency to change or "straighten the path. In this sense, the geodesic on a curved surface is an exact analog of a straight line in Euclidean space.
6. In the absence of friction, force bands may arrange themselves so they are loaded tangent to the endpoints. This is also termed "axial" loading. If the direction of a load placed on one endpoint changes, that endpoint will move until a new path is established tangent to the new loading direction (in the absence of friction).
7. All straight lines in a plane are geodesics. In FIGS. 37-39, force bands are conveniently drawn as straight lines and the surface is planar. However, the following statements that refer to straight lines on a plane also hold for force bands on a curved surface.
8. A load attached to a force band in between endpoints at any angle other than 0 degrees or 180 degrees (i.e. tangential, in line with the axis) causes a new geodesic endpoint to form. Referring to FIG. 37, a force band is formed by points 1 and 2 that are fixed to a surface (endpoints are shown as circles). A load is attached to the force band at point 3 thereby forcing the force band off its geodesic path and creating a corner. The corner is regarded as a connection point dividing the force band's original geodesic path into two new ones and creating a force equilibrium with the load force. The two force bands formed between points 1 and 3 and between 3 and 2 lengthen until the magnitude of their vector sum is equal to the load. If the surface is curved, the vector directions would be tangent to the geodesics. The geometry will adjust until each force band is loaded axially. A corollary to this is that two force bands connected to each other at their endpoints will form a single new force band following the geodesic path between the unconnected endpoints. Note: endpoints and connection points are essentially the same thing except that "connection point" emphasizes that force is being transmitted between force bands.
9. Referring to FIG. 38, when two point loads are added to a force band, the original force band can be broken into 3 geodesics. In order for the forces to balance around the connection point, the length (and therefore the tension) of all 3 force bands increases.
10. Referring to FIG. 39, if instead of point load connections, the load was distributed continuously along a portion of the force band, the original force band can be broken into 2 geodesic segments and a non-geodesic segment. The load is distributed continuously between points 3 and 4. Segments between points 1 and 3 and between 4 and 2 follow geodesics. The segment between points 3 and 4 is a non-geodesic force band that has been pulled away from the surface geodesic between point 3 and 4 (represented by the thin straight dashed line connecting them). FIG. 40 shows what happens in an element of the anchoring zone, assuming there is contact and curvature. FIG. 40 shows an element of an anchoring band in an anchoring zone. The anchoring zone is depicted as a layer of diaper material 4002 tensioned over a curved element of the body. Only an outside layer of skin 4003 is represented. The effect of a distributed load, L, is to shift the force, F, created on the surface away from the normal 4001. F therefore has a normal component, $F_N$, and a tangential component, $F_T$, along the surface perpendicular to the axis of the tension in the segment (between $T_1$ and $T_2$). In other words, when a distributed load pulls a force band off of its geodesic, the original normal force becomes tilted and the article side of the element gains a tangential component to counter the load. This tangential force is termed the "geometric anchoring force". The geometric anchoring force comes from stored elastic energy created as the load pulls the force band off a geodesic path. Note that the geometric anchoring force does not come from the body. In fact, the load force for this portion of the load is transmitted to another site in the anchoring system where geodesic anchoring occurs and a normal support reaction is generated. Thus "geometric anchoring" is actually a means to redirect loads to a location more suitable for geodesic anchoring.

The force bands described above can be configured into geodesic networks that can be tailored for specific applications. These networks may be represented as anchoring "schematics" that indicate the configuration of elements of the network. Each element in an anchoring schematic indicates the function that is to be carried out by an analogous element in the physical anchoring system. As used herein, anchoring schematics are shown in a perspective view on a wearer's body to indicate the approximate body location for each function. Any physical embodiment may be used to carry out the function as long as it can perform as desired in the location indicated and be successfully connected the other elements in the system. Anchoring schematics have only three different elements—force bands, connection points, and load forces. Force bands are represented by geodesic curves. Load forces are represented by force vectors that indicate the line of action of the load as expected in the physical embodiment while in use. Connection points are the idealized junctions between force bands and the means of attaching load forces to the network. Connection points are designated hereafter as item 548. Force bands and load forces attached to connection points communicate forces with each other and are free to rotate in all directions about the connection point. The only constraint is that none of the elements is allowed to penetrate the wearer's surface. Networks are assumed to be in equilibrium, which in some cases implies that each force band is in tension.

The human surface used in the schematics presented herein is intended to represent a typical walking baby between 12 and 24 months. Force bands are shown to be in the approximate geodesic location of this typical user of absorbent diapers but it should be appreciated that surface geometry is somewhat different in humans at different stages of growth and maturity. Once there is knowledge of where the geodesics in the schematics reside on a target wearer, the elements for a physical anchoring system can be sized and placed from the schematic and fabricated.

The simplest element of an anchoring system is a force band that follows an open geodesic path. FIG. 22 is a schematic of an open geodesic 549 between a point 548 in the center of the front and a point 548 in the center of the back of the baby. Force vectors 551 and 551' of equal magnitude, each tangent to its respective endpoint, represent either load forces acting on the force band or tension from another connected force band.

On a frictionless, but otherwise real baby, the tensioned load band would automatically adjust to follow a geodesic. If the tension were increased, the path could change slightly as the baby surface deforms in response to the increased normal force in the curved areas, but the path would remain stable. Schematics are assumed to be at their equilibrium geometry. It should be appreciated that in a physical embodiment of an open force band, efforts should be made to maintain substantially equal tension at both ends in order to prevent the band from moving along the geodesic path—i.e., sliding axially across the wearer's skin.

Load forces acting at the endpoints are anchored by support reactions occurring everywhere along the band where there is contact, tension, and curvature. Therefore most of the contact area under the band is considered an anchoring zone. However the amount of support provided varies within the anchoring zone. One reason is that the magnitudes of support reactions vary with surface curvature. The second reason is that the force balance on the system requires the sum of the reactions be equal and opposite to the sum of the load forces. Thus only the reaction components in the same direction as the vector sum of the load forces will support the load. It then follows that the portions of the anchoring zone that provides the most support are those that have a high curvature surface and are the most perpendicular to the vector sum of the loads of each force band. Thus in the case of the open load band in FIG. 22, most of the anchoring occurs over the hips where the surface has high curvature and is mostly perpendicular to the sum of the loads (the loads and their sum are all substantially parallel).

If the wearer is standing upright, most of the load forces to be anchored are substantially vertical. Therefore the valuable geodesics for anchoring are those that pass over surfaces with a horizontal component (and therefore the surface normal has a vertical component). Some portions of the body surface can be roughly conical. These surfaces can be characterized by their "cone angle" which is the angle that straight lines on the surface emanating from the theoretical apex of the cone make with the vertical axis of the cone. The larger the cone angle the flatter the cone and the larger the horizontal component of the surface. The un-deformed surface of the naked human has geodesics that have sufficient cone angles and curvature in places suitable for anchoring. These places tend to be at the sides of the body in the hip region. Because the geodesics passing over such surfaces produce normal force, the body compresses. If the body has compressibility gradients in y-direction, a roughly horizontal band with a width will tilt in at the top and enhance the cone angle and thus the amount of anchoring that can occur increases at a given tension. When a bone is relatively close to the surface, an anchoring band just above the bone in the y-direction will see a compressibility gradient in an advantageous direction and the cone angle will increase. Boney prominences that are particularly useful in anchoring are the iliac crest (of the pelvis) and the greater trochanter (of the femur).

By itself, this horizontal open force band may not perform useful anchoring because the surfaces it passes over are substantially vertical. However, by making sure the geodesic passes over areas with a good compression gradient and thus getting the benefit of a large cone angle, the endpoints could be rotated downward and produce a greater potential for anchoring. With endpoints rotated down, the force band will possess a favorable vertical component in the front and back can be directly used to anchor vertical loads in the front and back. By itself this force band may not be stable on its geodesic because there is no means to couple a vertical load into the force band axially.

Figure 24A:
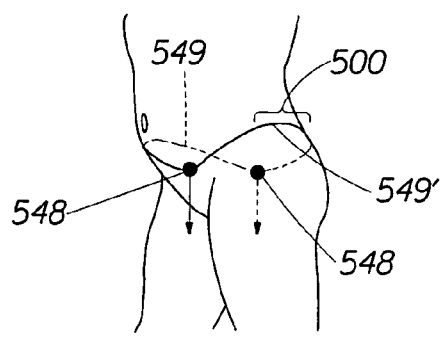
FIG. 24A illustrates a perspective view of a human body with force vectors relating to a particular embodiment of an anchoring system for a disposable absorbent article, according to the present disclosure.
Figure 24B:
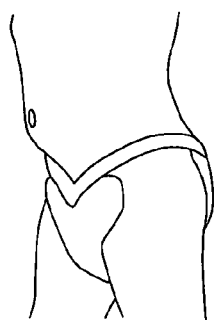
FIG. 24B illustrates a perspective view of the anchoring system for the force vectors of FIG. 24A, according to the present disclosure.
Figure 24C:
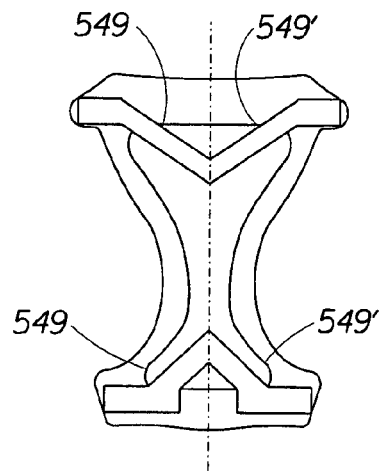
FIG. 24C illustrates a perspective view of the disposable absorbent article for the anchoring system of FIG. 24B, according to the present disclosure.

To overcome this, open geodesics can be combined into networks. For instance, FIG. 24A illustrates two mirror image open force bands 549 and 549' connected in the center of the wearer's front and back. If equal downward loads are attached to the connection points 548, a stable system can be achieved. The loads can be arranged so that they split equally between, and act tangentially on, the ends of the force bands 549 and 549'. For example, this will happen if the load forces bisect the angle between the two force bands at each connection point 548. The over-the-hip geodesics illustrated in FIG. 24A may depend on y-direction compressibility gradients to achieve a sufficiently vertical component.

In contrast, closed geodesics may provide self-stability. FIG. 23, for instance, illustrates a schematic of a typical closed geodesic force band 544 on a baby. When $\gamma < \pi$, the geodesic intersection (corner) is the ideal connection point 548 for loads. When the load is attached to the connection point 548, equal loads at both ends of the geodesic can occur. The closed geodesic force band 544 may automatically shift as needed to keep the load equally distributed to both ends of the band.

When the system anchors geodesically, the tension in the force band is a function of load, L (the vector 551 pointing downward) and the corner angle, $\gamma$. Tension, T, in the band equals $L/(2 \cos \gamma/2)$. From this equation it can be observed that, as $\gamma$ approaches 0, the tension in the band approaches L/2 (since the load splits evenly between the two ends), and is the lowest theoretically possible. As $\gamma \to \pi$ (while loaded), the tension theoretically approaches infinity. The value of $\gamma$ can be controlled by the relaxed length and spring constant of the force band. For example, $\gamma$ may decrease if the relaxed length is made longer or the spring constant, k, of the force band is made smaller. Reducing k, causes the force band to stretch further for the same load. As $\gamma$ gets smaller, the tension gets smaller, but the load connection point drops lower on the body. Therefore there are significant design tradeoffs between these parameters.

If $\gamma < \pi$ there is potential for "slack" to form in the load band during dynamic wear. This is because $\gamma < \pi$ implies that a shorter closed path exists. In dynamic wear situations, it is possible for the load to be temporarily in free flight and thus effectively reduce the load force to zero. It is then possible that with motion the force band will move to that shorter path and slack will form. With slack present it is possible for the force band to be easily moved off the desired geodesic and possibly cause it to fall off the wearer.

Figures 25A, 25B, 25C:
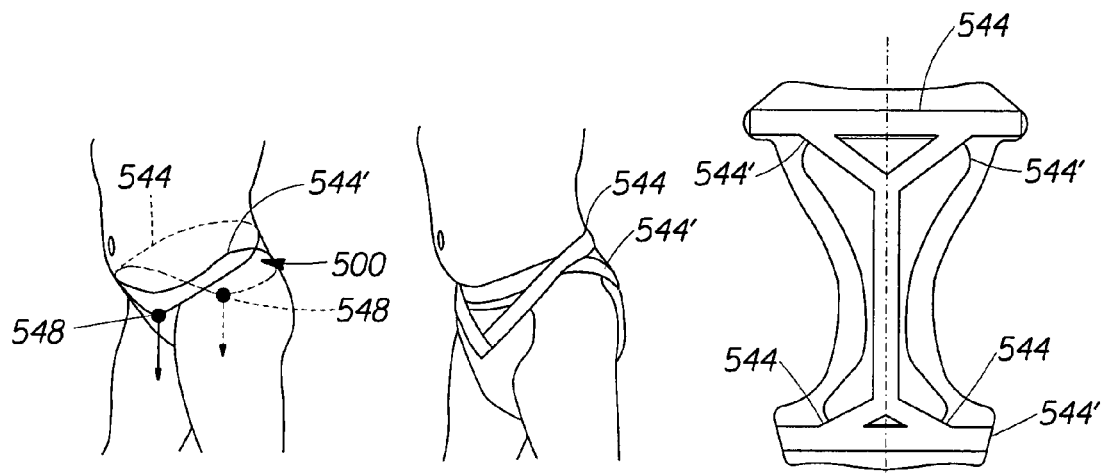
FIG. 25A illustrates a perspective view of a human body with force vectors relating to another particular embodiment of an anchoring system for a disposable absorbent article, according to the present disclosure.
FIG. 25B illustrates a perspective view of the anchoring system for the force vectors of FIG. 25A, according to the present disclosure.
FIG. 25C illustrates a perspective view of the disposable absorbent article for the anchoring system of FIG. 25B, according to the present disclosure.
Figures 26A, 26B, 26C:
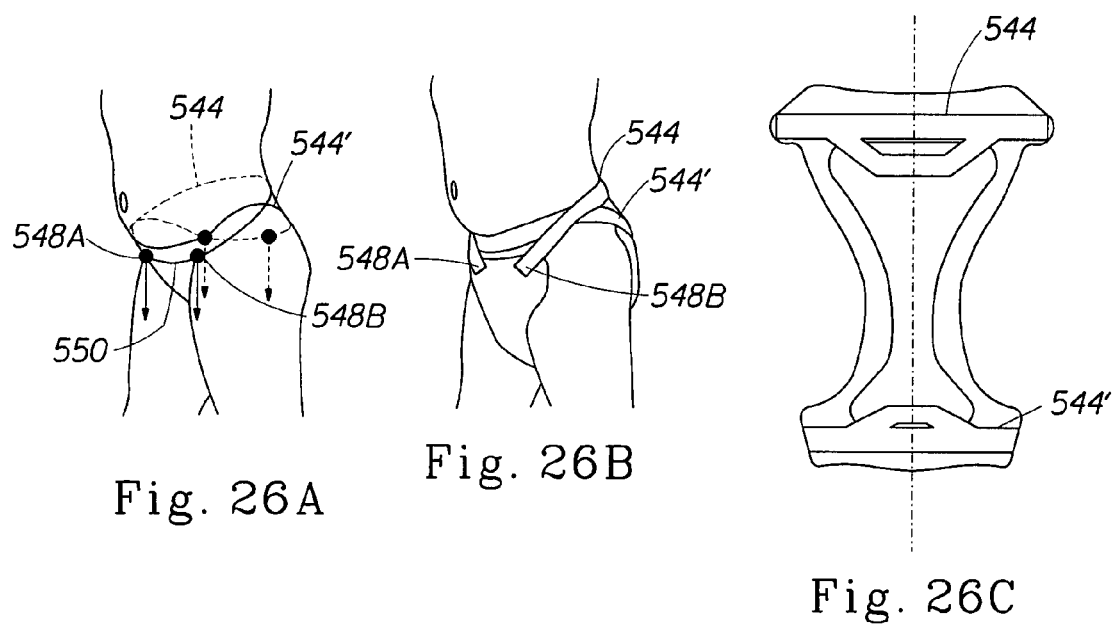
FIG. 26A illustrates a perspective view of a human body with force vectors relating to yet another particular embodiment of an anchoring system for a disposable absorbent article, according to the present disclosure.
FIG. 26B illustrates a perspective view of the anchoring system for the force vectors of FIG. 26A, according to the present disclosure.
FIG. 26C illustrates a perspective view of the disposable absorbent article for the anchoring system of FIG. 26B, according to the present disclosure.
Figure 27:
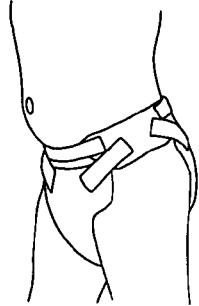
FIG. 27 illustrates a perspective view of an embodiment of an anchoring system for a disposable absorbent article, according to the present disclosure.

FIG. 25A shows two closed force bands, one band 544 to support loads in the front and another band 544' to support loads in the back. Independent front and back load supports can provide a stable solution for situations where loads originating in the front and back may be significantly different. The force band configurations shown in FIGS. 24A and 25A depict the approximate body location of four geodesics found to be useful in anchoring systems. The exact locations of the geodesics vary somewhat between groups at different stages of growth and maturity and between individual wearers within groups.

With knowledge of the basic principles of geodesics and the locations of useful body geodesics it can be appreciated that many different theoretical anchoring configurations can be created from force bands, connection points, and load forces toward particular design objectives. These schematics can be embodied digitally or physically and tested on virtual or real wearers as anchoring systems attached to a core assembly.

In anchoring system schematics, load forces are depicted in the figures only by their connection points and directions. By convention the schematic provides connection points on the anchoring system that anticipate matching connections on the core assembly; therefore making it unnecessary to specify the load forces further. A brief discussion follows of how some of the schematic anchoring configurations contemplated by the present invention are theoretically believed to work.

With regard to FIGS. 24A-33C, the "A" figures are the functional schematic, the "B" figures are the physical embodiment of the functional model, and the "C" figures are the physical embodiment within an absorbent article. As such, the force bands referred to hereafter represent the functional model for anchoring bands and LDEs of the physical anchoring system.

A suitable configuration of an anchoring system constructed in accordance with the present invention is shown in FIG. 24A. The FIG. 24A configuration may comprise two over-the-hip force bands 549, 549' with centered load connections, front and back. This is the simplest possible geodesic anchoring system. Anchoring occurs primarily by the normal force generated over the hips 500. The configuration is characterized by an angle, $\gamma$, at connection point 548 which is defined exactly as in FIG. 23. As $\gamma \to \pi$ this two geodesic system approaches a single closed geodesic. As described earlier in regard to a closed geodesic, there is a relationship between tension, load, and $\gamma$. $T=L/(2 \cos \gamma/2)$. An infinite tension causes $\gamma$ to approach $\pi$ with a non-zero load.

However, the configuration of FIG. 24A can be subject to two instabilities described previously. For example, in a frictionless system, unequal front and back loads may cause the system to rotate (e.g., from the front going down and back going up or vice-versa) generally about the x-axis (shown in FIG. 8). In a physical embodiment, friction will permit a difference in front and back loads. As such, in some embodiments, the tension in the anchoring bands can be increased by increasing $\gamma$. The increase in $\gamma$ will increase the tension in the anchoring bands thereby increasing the friction which can widen the tolerance for unequal loads. However, friction is not always dependable in dynamic situations. As such, in some embodiments, load balancing can be achieved by separately adjusting $\gamma$ between front and back by changing the elevation of the connection points 548. This approach may be particularly useful if the ratio of the front and back loads remains fairly constant. Tension would be the same front and back when the following condition is met.

$$\frac{L_1}{L_2} = \frac{\cos(\gamma_1/2)}{\cos(\gamma_2/2)}$$

Note that changing $\gamma$ can change the geodesic path. Another example of an instability comes from slack (also described previously) in a dynamic system. The smaller $\gamma$ is, the longer the total path length of the geodesics, and the larger the potential slack. Potential slack has an advantage in pant products because if $\gamma$ is low enough, the slack can be enough to allow the pant to be pulled over the buttocks and hips without requiring the anchoring bands to stretch. Of course, the downside of slack is instability. Where $\gamma$ smaller, stability can be obtained by providing low-force elastic structures designed to simply keep the geodesics in place in the event of slack-caused a dynamic excursion. In the present invention an elastic biaxial stretch outer cover can serve the role. For stand-alone anchoring systems, the following configuration can be used.

In some embodiments, an anchoring system constructed in accordance with the present invention may be configured as shown in FIG. 29A. The FIG. 29A configuration may comprise two over-the-hip force bands 549, 549' with centered load connections 548, front and back with an elastic stabilizing band 561. This configuration takes care of the stability problem of the anchoring system of FIG. 24A configuration by adding a low force closed elastic geodesic to simply maintain the location of the anchoring bands in the event they are slack during a dynamic excursion. Stabilizing bands are joined to the geodesic force bands; however, there may be no significant force balance to be considered at the attachment points. In some embodiments, for example, in a pant, the elastic stabilizing band 561 can easily stretch when the pant is pulled up, but it would not have to carry a large portion if any of anchoring load during wear.

Figure 32A:
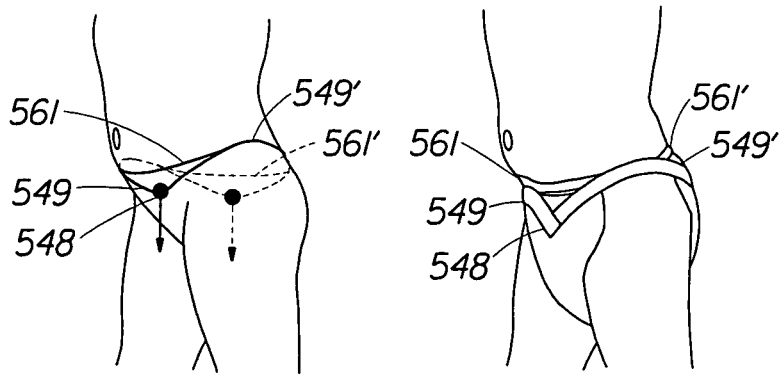
FIG. 32A illustrates a perspective view of a human body with force vectors relating to an additional particular embodiment of an anchoring system for a disposable absorbent article, according to the present disclosure.
Figure 32B:
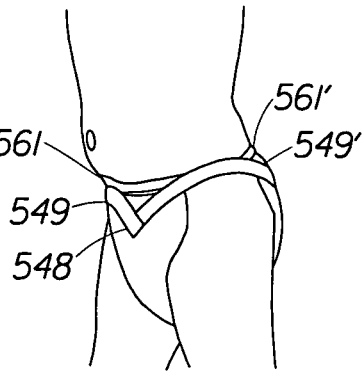
FIG. 32B illustrates a perspective view of the anchoring system for the force vectors of FIG. 32A, according to the present disclosure.
Figure 32C:
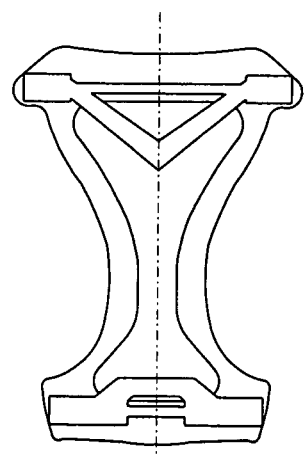
FIG. 32C illustrates a perspective view of the disposable absorbent article for the anchoring system of FIG. 32B, according to the present disclosure.

In some embodiments an anchoring system constructed in accordance with the present invention may be configured as shown in FIG. 32A. The anchoring system of FIG. 32A may comprise two open geodesic stabilizing bands 561, 561' instead of the single closed geodesic of FIG. 29A. The stabilizing bands 561 and 561' may be joined to the force bands 549 and 549'; however, no significant force balance may need to be considered. Both stabilizing band configurations of FIGS. 29A and 32A can work for stand-alone anchoring systems.

In some embodiments, an anchoring system constructed in accordance with the present invention may be configured as shown in FIG. 25A. The FIG. 25A configuration may comprise two closed force bands 544, 544' and centered load connections 548, front and back. The closed geodesics are anchored in the same general area 500 over the hips as the other systems described thus far. This system is very stable particularly if operating with little or no slack. It can be particularly effective where the article is a side-fastened taped diaper. In some cases the center load connection points 548 may be too low on the core assembly (as may be the case for any centered load connections). The load connection points 548 can be raised using the configuration shown in FIG. 26A.

In some embodiments, the load connection points 548 can be configured to provide two load connection points 548A and 548B that are higher and outboard of the original location of the single connection point 548 (shown in FIG. 25A). FIGS. 34 and 35 show how the two configurations provide equivalent anchoring with different load connections. FIG. 34 represents one of the closed force bands 544 with a center load connection 548. The force band is "cut" by a horizontal line 501 above the original connection point 548 and below the portion of the force band 544 where normal support reactions occur 500 (shown in FIG. 25A). This creates two new connection points 548A and 548B. In FIG. 35, a new single geodesic 550 reconnects the force band 544 at the new connection points 548A and 548B and provides the means to resolve the horizontal components of the tension in the remainder of the original force band 544. The vertical load force may be split into two halves and moved to the two new connection points 548A and 548B. At each connection point 548A and 548B, the force band 544 and new load force add vectorially so that the portion of force band 544 above the "cut" line 501 may experience the same axial tension as before. Any load connection point can be reconfigured as long as the parts of the geodesic where the anchoring reactions take place are unchanged and they remain axially loaded with the same tension.

Figure 28A:
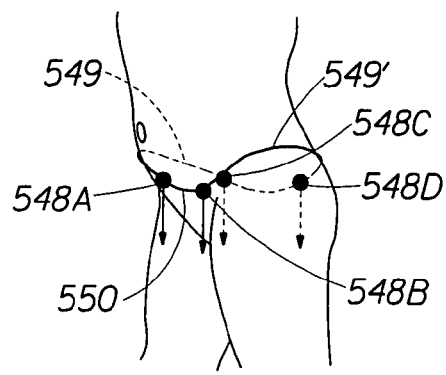
FIG. 28A illustrates a perspective view of a human body with force vectors relating to still another particular embodiment of an anchoring system for a disposable absorbent article, according to the present disclosure.
Figure 28B:
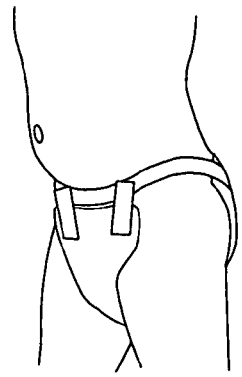
FIG. 28B illustrates a perspective view of the anchoring system for the force vectors of FIG. 28A, according to the present disclosure.
Figure 28C:
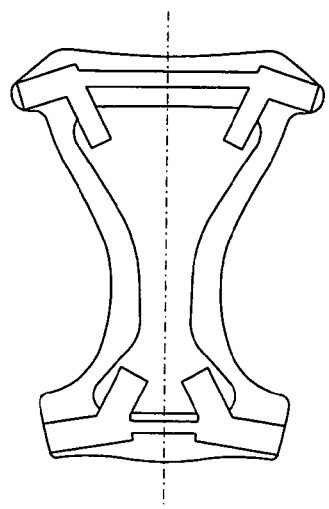
FIG. 28C illustrates a perspective view of the disposable absorbent article for the anchoring system of FIG. 28B, according to the present disclosure.

In some embodiments, an anchoring system constructed in accordance with the present invention may be configured as shown in FIGS. 28A-28C. As shown in FIG. 28A, the anchoring system may comprise two over-the-hip force bands 549, 549' similar to the FIG. 24A configuration but with raised connection points 548A, 548B, 548C, and 548D. The connection points 548A and 548B may be disposed at the front of a wearer while the connection points 548C and 548D may be disposed at the back of a wearer, when the anchoring system is in use. The load connection points may be derived from the FIG. 24A configuration in the same way that the FIG. 26A configuration was derived from the FIG. 25A configuration.

Figure 31A:
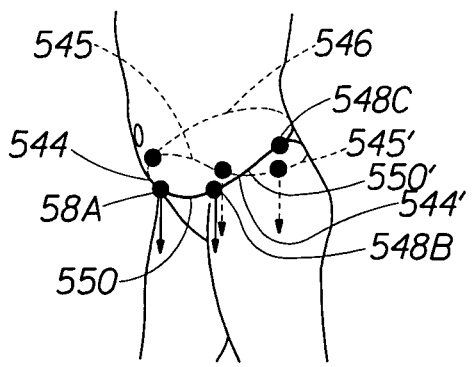
FIG. 31A illustrates a perspective view of a human body with force vectors relating to a yet further particular embodiment of an anchoring system for a disposable absorbent article, according to the present disclosure.
Figure 31B:
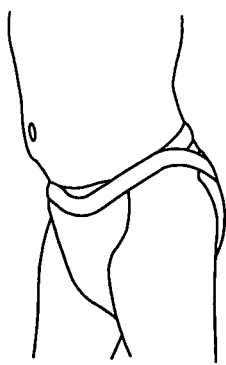
FIG. 31B illustrates a perspective view of the anchoring system for the force vectors of FIG. 31A, according to the present disclosure.
Figure 31C:
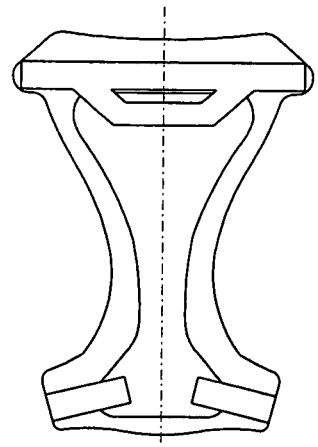
FIG. 31C illustrates a perspective view of the disposable absorbent article for the anchoring system of FIG. 31B, according to the present disclosure.

In some embodiments, an anchoring system constructed in accordance with the present invention may be configured as shown in FIGS. 30A, 30B, and 31A-31C. As shown in FIGS. 30A and 31A in some embodiments, an anchoring system may comprise portions of the open and closed geodesic configurations discussed with regard to FIGS. 24A and 25A. For example, an anchoring system may comprise two and four load connection point versions of a hybrid of the closed and open geodesic configurations of FIGS. 24A and 25A. These configurations have 5 and 7 open geodesic force bands, respectively. The creation of the extra connection points can create two additional open geodesic force bands (550 and 550') in FIG. 31A. They are distinguished from previous configurations by pre-tensioned force bands made up of an upper open force band 546 in the back and two front open force bands 544, 544'. Pre-tensioning (i.e. tension caused by the application process, not by load forces) provides stability for the force bands and a tension bias that improves geometric anchoring.

Once loads are applied (as illustrated), the geodesics that meet at the side connection points form angles that balance the forces in 546, 545' and 544'. The same can be true for the opposite side of the body. Thus the geodesic paths of this configuration will be slightly different than geodesics that run continuously through this area of the body such as those of FIGS. 24A and 25A. There are many practical advantages to this configuration. As in most configurations, anchoring occurs primarily in the hip regions.

In some embodiments, an anchoring system constructed in accordance with the present invention may be configured as shown in FIGS. 33A-33C. As shown, the FIG. 33A configuration may comprise a single pre-tensioned circumference made up of four open force bands 570, 571, 572, 573 and a zone 574, 574' of distributed load force over each hip. The schematic symbol for a distributed load force is introduced in this figure. The idea behind this configuration is to leverage the geometric anchoring mode. This load distribution is not straight-forward to physically embody because there are no loads nor pathways to loads directly below this area. In practice, a structure is provided that can take loads diagonally from the front and back, balance the horizontal components and distribute the vertical components to the geodesic. Such loads would cause the geodesic to move off its true geodesic path as has been previously described. FIG. 33B shows a structure that approximates this behavior.

A small amount of stretch can help geodesic stability and is hence often desirable. On the other hand, increasing the length of the force bands will change the geometry and run the risk that the new geometry may not fall on desirable geodesics. There are many ways to configure stretch in the anchoring system. One skilled in the art will recognize that it would be useful to test theoretical configurations incorporating stretch prior to engineering an anchoring configuration into a complete product. Force bands can be divided into sections with differing stretch properties. Often the same amount of stretch in one section can have a lower impact on geodesic geometry than in another.

If an anatomically accurate digital or physical mannequin is available, schematics can be literally studied with systems of strings, springs, and load weights. Each force band is simulated by a string in series with a steel spring with a known constant. Simple ways are devised to connect simulated force bands together. Loads can be simulated by hanging weights. This allows the geodesic stability response of the network to be studied and optimized for the stretch placement and extension properties. Since stretch is often employed to improve size range, this too can be easily studied if different size mannequins or "virtual wearers" are available.

In the case of anchoring systems implemented into taped diapers, it is usually possible to select a force band section for stretch that will have a minimum impact on geodesic geometry. For example, in the FIG. 31A configuration the force bands 544 and 544' between each side connection point and the front is a good place for stretch. The connection point on the core could literally be the landing zone for a fastener. A landing zone located along the connecting geodesic across the core could provide sufficient rigidity so that the weight of the core could be correctly directed to the stretch anchoring band.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference, however the citation of any document is not construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It should be apparent that combinations of such embodiments and features are possible and can result in executions within the scope of this invention. It is therefore intended to cover in the appended claims all such changes and modifications that are within the scope of this invention.

What is claimed is:

1. A disposable wearable absorbent article comprising an absorbent core, an outer cover, wherein the outer cover has an outer cover modulus of elasticity, end edges, and an anchoring system including one or more tension carrying load distribution elements that are bonded to the absorbent core such that they collect loads from the absorbent core and transfer them to the hip region of the article to anchor the absorbent core to a wearer, wherein the outer cover includes a first portion, in which substantially all of the anchoring system is integral with the outer cover, and a second portion, outside of the first portion, and wherein the anchoring system is spaced apart from the end edges, and wherein the anchoring system at least partially overlaps a portion of the absorbent core, and wherein the anchoring system comprises a circumferential anchoring member, at least a portion of which traverses the hip region of the article, and that has an anchoring member modulus of elasticity that is greater than the outer cover modulus of elasticity;

and wherein the outer cover is bonded to the absorbent core where the load distribution elements are bonded to the absorbent core; and wherein the load distribution elements comprise a nonwoven and have been incrementally stretched.

2. The disposable wearable absorbent article of claim 1, wherein the first portion of the outer cover is incrementally stretched to a first degree, and the second portion of the outer cover is incrementally stretched to a second degree that is less than the first degree.

3. The disposable wearable absorbent article of claim 1, wherein the first portion of the outer cover is configured to have a first modulus of elasticity, and the second portion of the outer cover is configured to have a second modulus of elasticity that is less than the first modulus of elasticity.

4. The disposable wearable absorbent article of claim 1, wherein the first portion of the outer cover is printed with a higher caliper elastomer, and the second portion of the outer cover is printed with a lower caliper elastomer.

5. The disposable wearable absorbent article of claim 1, wherein the first portion of the outer cover is printed with a higher performance elastomer, and the second portion of the outer cover is printed with a lower performance elastomer.

6. The disposable wearable absorbent article of claim 1, wherein the first portion of the outer cover is unstretched, and the second portion of the outer cover is incrementally stretched.

7. The disposable wearable absorbent article of claim 1, wherein the first portion of the outer cover is over-bonded.

8. The disposable wearable absorbent article of claim 1, wherein the first portion of the outer cover is configured to have a first force per unit width at a particular strain, and the second portion of the outer cover is configured to have a second force per unit width at the particular strain, wherein the second force per unit width is less than the first force per unit width.

9. The disposable wearable absorbent article of claim 8, wherein a ratio of the first force per unit width to the second force per unit width is 1.5-10.

10. The disposable wearable absorbent article of claim 1, including an absorbent core assembly, which includes the absorbent core, wherein the anchoring system is configured to anchor the absorbent core assembly to a wearer.

11. The disposable wearable absorbent article of claim 1, wherein at least the second portion of the outer cover is uniaxially stretchable.

12. The disposable wearable absorbent article of claim 1, wherein at least the second portion of the outer cover is biaxially stretchable.

13. The disposable wearable absorbent article of claim 1, wherein at least the second portion of the outer cover is a zero-strain laminate.

14. The disposable wearable absorbent article of claim 1, wherein the article is a fastenable disposable wearable absorbent article.

15. The disposable wearable absorbent article of claim 1, wherein the article is a pant-type disposable wearable absorbent article.

16. The disposable wearable absorbent article of claim 10, wherein the absorbent core assembly is bucket-shaped.

* * * * *